United States Patent
Remuiñan et al.

(10) Patent No.: US 7,495,000 B2
(45) Date of Patent: Feb. 24, 2009

(54) VARIOLIN DERIVATIVES AND THEIR USE AS ANTITUMOR AGENTS

(75) Inventors: Modesto Remuiñan, Madrid (ES); Juan Jose Gonzalez, Madrid (ES); Carlos Del Pozo, Madrid (ES); Carmen Cuevas, Madrid (ES); Simon Munt, Madrid (ES); Regan James Anderson, Meylan (FR); Andres Francesh, Madrid (ES); Jonathan Charles Morris, Brompton (AU); Ignacio Manzanares, Madrid (ES)

(73) Assignee: Pharma Mar, S.A., Madrid (ES)

( * ) Notice: Subject to any disclaimer, the term of this patent is extended or adjusted under 35 U.S.C. 154(b) by 606 days.

(21) Appl. No.: 10/483,525

(22) PCT Filed: Jul. 11, 2002
(Under 37 CFR 1.47)

(86) PCT No.: PCT/GB02/03197
§ 371 (c)(1),
(2), (4) Date: Mar. 7, 2005

(87) PCT Pub. No.: WO03/006457
PCT Pub. Date: Jan. 23, 2003

(65) Prior Publication Data
US 2006/0235223 A1    Oct. 19, 2006

(30) Foreign Application Priority Data
Jul. 11, 2001    (GB)    ................... 0116966.3

(51) Int. Cl.
A61K 31/506    (2006.01)
C07D 239/06    (2006.01)
(52) U.S. Cl. .................. 514/256; 514/293; 544/242
(58) Field of Classification Search ................. 514/256, 514/293; 544/242; 546/276
See application file for complete search history.

(56) References Cited

U.S. PATENT DOCUMENTS

| | | | |
|---|---|---|---|
| 2004/0058939 A1 | 3/2004 | Alvarez et al. | |
| 2005/0014778 A1 | 1/2005 | Morris et al. | ............... 514/292 |

FOREIGN PATENT DOCUMENTS

| | | |
|---|---|---|
| WO | WO 02/04447 | 1/2002 |
| WO | WO 02/12240 | 2/2002 |
| WO | WO 03/006457 | 1/2003 |

OTHER PUBLICATIONS

Alvarez et al., "Synthesis of Deoxyvariolin B", Tetrahedron Letters, vol. 42, No. 8, Jan. 2001, pp. 315-317.
Alvarez et al., "Synthesis of 1, 2-dihydropyrrolo[1,2-c]primidin-1-ones", J. Chem. Soc. Perkins Trans. I, pp. 249-255 (1999).
Alvarez et al., "Synthesis of 3-Aryl- and 3-Heteroaryl-7-azaindoles", Synthesis, pp. 615-620 (1999).
Anderson et al., Studies toward the total synthesis of the variolins: rapid entry to the core structure: Tetrahedron Letters, vol. 42, No. 8, Jan. 2001, pp. 311-313.
Anderson et al., "Total Synthesis of Variolin B", Tetrahedron Letters, vo. 42, No. 3, Dec. 2001, pp. 8697-8699.
Calabresi et al., "Chemotherapy of Neoplastic Diseases", Goodman & Gilman's The Pharmacological Basis of Therapeutics, 9th ed., New York: McGraw-Hill, 1996, , pp. 1225-1229.
Capuano, Lilly et al., "(Heterocyclizations, XIII) New Polycyclic Pyrimidines with Bridge-Head Nitrogen", Chem. Ber., 107, pp. 929-936 (1974).
Charya et al., "Wynthesis and Evaluation of Sulphonylhydrazones of Phthalimido Acetaldehyde as Anticancer Agents", J. Indian Chem Soc., vol. 75, Jan. 1998, pp. 46-48.
Desarbre et al., "Synthesis of 2-Substituted-1H-Pyrrolo[2,3-b] Pyridines: Preparation of 7-Azaolivacine Analogue and 7-Azaindolopyridopyrimidine Derivatives", Tetrahedron, 53(10), pp. 3637-3648 (1997).
Erba et al., "Cell cycle phase perturbation and apoptosis induced by Variolin B, a novel antitumor agent of marine origin", Proc. Am. Assoc. Can. Res. Annual Meeting, vol. 27, #198 pp. 28-29 (1996).

(Continued)

*Primary Examiner*—Taofiq A Solola
(74) *Attorney, Agent, or Firm*—Fish & Richardson P.C.

(57) ABSTRACT

Variolin derivatives of formula (5) are provided, wherein the substituent groups defined by $X_2$, $R_1$, $R_2$, $R_3$, $R_6$, $R_7$ and $R_{12}$ are each independently selected from the group consisting of H, OH, OR', SH, SR', SOR', $SO_2R'$, $NO_2$, $NH_2$, NHR', $N(R')_2$, NHCOR', $NHSO_2R'$, CN, halogen, =O, C(=O)H, C(=O)R', $CO_2H$, $CO_2R'$, carboxyalkyl, $C_1$-$C_{12}$ alkyl, $C_2$-$C_{12}$ alkenyl, $C_2$-$C_{12}$ alkynyl, substituted or unsubstituted aryl, substituted or unsubstituted aralkyl and substituted or unsubstituted heteroaromatic; wherein each of the R' groups is independently selected from the group consisting of H, OH, SH, $NO_2$, $NH_2$, CN, halogen, =O, C(=O)H, C(=O)$CH_3$, $CO_2H$, $CO_2CH_3$, $C_1$-$C_{12}$ alkyl, $C_2$-$C_{12}$ alkenyl, $C_2$-$C_{12}$ alkynyl, aryl, aralkyl and heteroaromatic; wherein the pairs of groups $R_1$ and $R_2$, $R_2$ and $R_3$, $R_3$ and $R_{12}$, $R_{12}$ and $R_6$, or $R_6$ and $R_7$ may be joined into a carbocyclic or heterocyclic ring system.

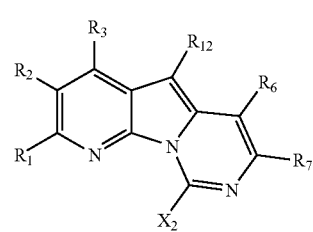

(5)

36 Claims, No Drawings

OTHER PUBLICATIONS

Fresenda et al., "Synthetic studies towards the 2-aminopyrimidine alkaloids variolins and meridianins from marine origin", Tetrahedron Letters, vol. 41, 2000, pp. 4777-4780.

Girgis et al., "The Synthesis of 5-Azaindoles by Substitution-Rearrangement of 7-Azaindoles upon Treatment with Certain Primary Amines", J. Heterocyclic Chem., vol. 26, No. 2, pp. 317-325 (1989).

Katritzky et al., Comprehensive Heterocyclic Chemistry, Pergamon Press, Oxford, vol. 3, p. 111 (1984).

Katritzky, Alan R. et al., "Activation of the 2-Alkyl Group of a 2-Alkylindole toward Proton Loss and Subsequent Electrophilic Substitution", J. Am. Chem. Soc., vol. 108, No. 21, pp. 6808-6809 (1986).

Lorenz et al. "A New Indole Synthesis", J. Org. Chem., vol. 30, pp. 2531-2533 (1965).

Majeed et al., "Stannylation Reactions and Cross-Couplings in Pyrimidines", Tetrahedron, vol. 45, No. 4, pp. 993-1006 (1989).

Mendiola et al., "Reaction of 2-Bromomethylazoles and TosMIC: A Domino Process to Azolopyrimidines. Synthesis of Core Tricycle of the Variolins Alkaloids", Organic Letters, vol. 2, No. 21, pp. 3253-3256 (2000).

Molina et al., "Synthesis of the potent antitumoral marine alkaloid variolin B", Tetrahedron Letters, vol. 43, Feb. 2002, pp. 1005-1007.

Perry et al., "Alkaloids from the Antarctic sponge Kirkpatrickia Varialosa—Part 1: Variolin B, A New Antitumour and Antiviral Compound", Tetrahedron, vol. 50, No. 13, 1994, pp. 3987-3992.

Sawayama et al., "Displacement Reactions of 2-Alkylsulfonyl-4-Chloropyrimidine Derivatives with Nucleophiles", Heterocycles, vol. 8, pp. 299-305 (1977).

Simone, "Oncology: Introduction", Cecil Textbook of Medicine, 20th Edition, vol. 1, pp. 1004-1010, 1996.

Trimurtulu et al., "Alkaloids from the Antarctic Sponge Kirkpatrickia varialosa—Part 2: Variolin A and N(3?) methyl tratrhydrovariolin B" Tetrahedron, vol. 50, No. 13, 1994, pp. 3993-4000.

Vorbrüggen et al., Syntheses of Nucleosides—Amination of Heterocycles—A New Simple Synthesis of Cytidines, Liebigs Annalen Der Chemie, pp. 988-1002 (1975).

VARIOLIN DERIVATIVES AND THEIR USE AS ANTITUMOR AGENTS

The present invention relates to antitumoral compounds, and in particular to new antitumoral analogs of variolin compounds including variolin B and deoxyvariolin B.

BACKGROUND OF THE INVENTION

The variolins are a class of marine alkaloids isolated from the rare, difficult to access Antarctic sponge *Kirkpatrickia varialosa*, with variolin B (1) being a typical example. The variolins all contain a fused pyrido[3'.2':4.5]pyrrolo[1.2-c]pyrimidine core (2), with either a heterocyclic aromatic ring or an ester group attached at $C_5$, as in variolin B (1), variolin D (3) and deoxyvariolin B (4).

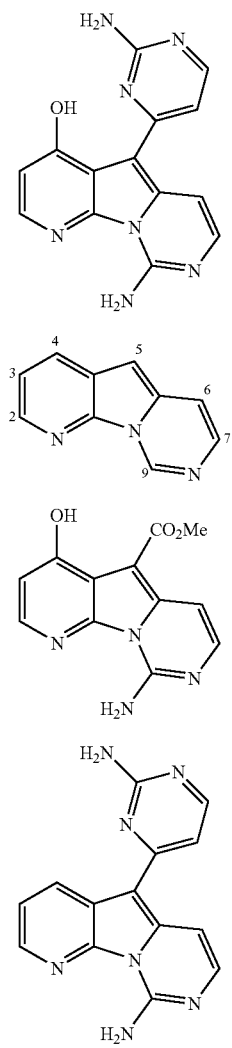

The variolins are disclosed to have antitumor activity and other useful properties. The complete structure for these and related compounds is given by N. B. Perry et al., *Tetrahedron* 1994, 50, 3987-3992 and G. Trimurtulu et al., *Tetrahedron* 1994, 50, 3993-4000.

Synthetic studies towards the 2-aminopyrimidine alkaloids variolins and meridianins are the subject of *Tetrahedron Lett.* 2000, 41, 4777-4780. M. Alvarez et al., *Tetrahedron Lett.* 2001, 42, 315-317 describe a synthesis to deoxyvariolin B starting from 7-azaindole. Studies towards the total synthesis of the variolins are decribed in *Tetrahedron Lett.* 2001, 42, 311-313. The first total synthesis of variolin B was described by R. J. Anderson et al. *Tetrahedron Lett.* 2001, 42, 8697-8699. Later, P. Molina et al. *Tetrahedron Lett.* 2002, 43, 1005-1007 also described the synthesis of variolin B achieved by tandem aza-Wittig/carbodiimide cyclisation.

WO 0204447 published 17 Jan. 2002 describes a method for preparation of variolin B (1) and deoxyvariolin B (4) from simple monoheteroaromatic starting materials, along with providing new variolin derivatives.

WO 0212240 published 14 Feb. 2002 relates to derivatives of variolin B.

SUMMARY OF THE INVENTION

The present invention is directed to compounds of general formula (5) that have the fused pyrido pyrrolo pyrimidime ring system of the variolin compounds:

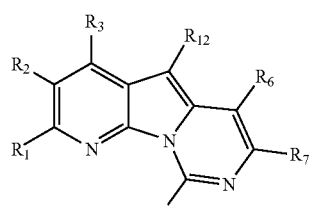

wherein the substituent groups defined by $X_2$, $R_1$, $R_2$, $R_3$, $R_6$, $R_7$ and $R_{12}$ are each independently selected from the group consisting of H, OH, OR', SH, SR', SOR', $SO_2R'$, $NO_2$, $NH_2$, NHR', $N(R')_2$, NHCOR', $NHSO_2R'$, CN, halogen, =O, C(=O)H, C(=O)R', $CO_2H$, $CO_2R'$, carboxyalkyl, $C_1$-$C_{12}$ alkyl, $C_2$-$C_{12}$ alkenyl, $C_2$-$C_{12}$ alkynyl, substituted or unsubstituted aryl, substituted or unsubstituted aralkyl and substituted or unsubstituted heteroaromatic;

wherein each of the R' groups is independently selected from the group consisting of H, OH, SH, $NO_2$, $NH_2$, CN, halogen, =O, C(=O)H, C(=O)$CH_3$, $CO_2H$, $CO_2CH_3$, $C_1$-$C_{12}$ alkyl, $C_2$-$C_{12}$ alkenyl, $C_2$-$C_{12}$ alkynyl, aryl, aralkyl and heteroaromatic;

wherein the pairs of groups $R_1$ and $R_2$, $R_2$ and $R_3$, $R_3$ and $R_{12}$, $R_{12}$ and $R_6$, or $R_6$ and $R_7$ may be joined into a carbocyclic or heterocyclic ring system.

In a related aspect, the invention provides compounds of the formula (5a):

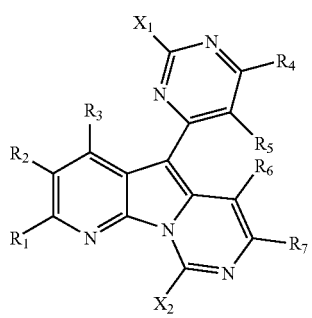

wherein the substituent groups defined by $X_1$, $X_2$, $R_1$, $R_2$, $R_3$, $R_4$, $R_5$, $R_6$ and $R_7$ are each independently selected from the group consisting of H, OH, OR', SH, SR', SOR', $SO_2R'$, $NO_2$, $NH_2$, NHR', $N(R')_2$, NHCOR', $NHSO_2R'$, CN, halogen, =O, C(=O)H, C(=O)R', $CO_2H$, $CO_2R'$, carboxyalkyl; $C_1$-$C_{12}$ alkyl, $C_2$-$C_{12}$ alkenyl, $C_2$-$C_{12}$ alkynyl, substituted or unsubstituted aryl, substituted or unsubstituted aralkyl and substituted or unsubstituted heteroaromatic;

wherein each of the R' groups is independently selected from the group consisting of H, OH, SH, $NO_2$, $NH_2$, CN, halogen, =O, C(=O)H, C(=O)$CH_3$, $CO_2H$, $CO_2CH_3$, $C_1$-$C_{12}$ alkyl, $C_2$-$C_{12}$ alkenyl, $C_2$-$C_{12}$ alkynyl, aryl, aralkyl and heteroaromatic;

wherein the pairs of groups $R_1$ and $R_2$, $R_4$ and $R_5$, or $R_6$ and $R_7$ may be joined into a carbocyclic or heterocyclic ring system.

Suitable halogen substituents in the compounds of the present invention include F, Cl, Br and I.

Alkyl groups preferably have from 1 to about 12 carbon atoms, more preferably 1 to about 8 carbon atoms, still more preferably 1 to about 6 carbon atoms, and most preferably 1, 2, 3 or 4 carbon atoms. Methyl, ethyl and propyl including isopropyl are particularly preferred alkyl groups in the compounds of the present invention. As used herein, the term alkyl, unless otherwise modified, refers to both cyclic and noncyclic groups, although cyclic groups will comprise at least three carbon ring members.

Preferred alkenyl and alkynyl groups in the compounds of the present invention have one or more unsaturated linkages and from 2 to about 12 carbon atoms, more preferably 2 to about 8 carbon atoms, still more preferably 2 to about 6 carbon atoms, even more preferably 2, 3 or 4 carbon atoms.

The terms alkenyl and alkynyl as used herein refer to both cyclic and noncyclic groups, although straight or branched noncyclic groups are generally more preferred.

Preferred alkoxy groups in the compounds of the present invention include groups having one or more oxygen linkages and from 1 to about 12 carbon atoms, more preferably from 1 to about 8 carbon atoms, and still more preferably 1 to about 6 carbon atoms, and most preferably 1, 2, 3 or 4 carbon atoms.

Preferred alkylthio groups in the compounds of the present invention have one or more thioether linkages and from 1 to about 12 carbon atoms, more preferably from 1 to about 8 carbon atoms, and still more preferably 1 to about 6 carbon atoms. Alkylthio groups having 1, 2, 3 or 4 carbon atoms are particularly preferred.

Preferred alkylsulphinyl groups in the compounds of the present invention include those groups having one or more sulphoxide (SO) groups and from 1 to about 12 carbon atoms, more preferably from 1 to about 8 carbon atoms, and still more preferebly 1 to about 6 carbon atoms. Alkylsulphinyl groups having 1, 2, 3 or 4 carbon atoms are particularly preferred.

Preferred alkylsulphonyl groups in the compounds of the present invention include those groups having one or more sulphonyl (SO2) groups and from 1 to about 12 carbon atoms, more preferably from 1 to about 8 carbon atoms, and still more preferably 1 to about 6 carbon atoms. Alkylsulphonyl groups having 1, 2, 3 or 4 carbon atoms are particularly preferred.

Preferred aminoalkyl groups include those groups having one or more primary, secondary and/or tertiary amine groups, and from 1 to about 12 carbon atoms, more preferably 1 to about 8 carbon atoms, still more preferably 1 to about 6 carbon atoms, even more preferably 1, 2, 3 or 4 carbon atoms. Secondary and tertiary amine groups are generally more preferred than primary amine moieties.

Suitable carboxyalkyl groups include mono- and di-carboxy substituted alkyl groups. The carboxy groups typically take the form COOR', especially where R' is hydrogen or alkyl, preferably hydrogen or methyl.

Suitable heterocyclic groups comprise heteroaromatic and heteroalicyclic groups. Suitable heteroaromatic groups in the compounds of the present invention contain one, two or three heteroatoms selected from N, O or S atoms and include, e.g., coumarinyl including 8-coumarinyl, quinolinyl including 8-quinolinyl, pyridyl, pyrazinyl, pyrimidyl, furyl, pyrrolyl, thienyl, thiazolyl, oxazolyl, imidazolyl, indolyl, benzofuranyl and benzothiazol. Suitable heteroalicyclic groups in the compounds of the present invention contain one, two or three heteroatoms selected from N, O or S atoms and include, e.g., tetrahydrofuranyl, tetrahydropyranyl, piperidinyl, morpholino and pyrrolindinyl groups.

Suitable carbocyclic aryl groups in the compounds of the present invention include single and multiple ring compounds, including multiple ring compounds that contain separate and/or fused aryl groups. Typical carbocyclic aryl groups contain 1 to 3 separate or fused rings and from 6 to about 18 carbon ring atoms. Specifically preferred carbocyclic aryl groups include phenyl including substituted phenyl such as 2-substituted phenyl, 3-substituted phenyl, 4-substituted phenyl, 2.3-substituted phenyl, 2.4-substituted phenyl, 2.5-substituted phenyl, 2.6-substituted phenyl, 3.4-substituted phenyl, 3.5-substituted phenyl, 3.6-substituted phenyl, 2.3.4-substituted, 2.3.5-substituted, 2.3.6-substituted, 2.4.5-substituted, 2.4.6-substituted, and 3.4.5-substituted phenyl, including where one or more or the phenyl substituents is a group such as halogen, cyano, nitro, alkanoyl, sulphinyl, sulphonyl and the like; naphthyl including 1-naphthyl and 2-naphthyl; biphenyl; phenanthryl; and anthracyl.

References herein to substituted R' groups in the compounds of the present invention refer to the specified moiety that may be substituted at one or more available positions by one or more suitable groups, e.g., halogen such as fluoro, chloro, bromo and yodo; cyano; hydroxyl; nitro; azido; alkanoyl such as a C1-6 alkanoyl group such as acyl and the like; carboxamido; alkyl groups including those groups having 1 to about 12 carbon atoms or from 1 to about 6 carbon atoms and more preferably 1-3 carbon atoms; alkenyl and alkynyl groups including groups having one or more unsaturated linkages and from 2 to about 12 carbon or from 2 to about 6 carbon atoms; alkoxy groups having those having one or more oxygen linkages and from 1 to about 12 carbon atoms or 1 to about 6 carbon atoms; aryloxy such as phenoxy; alkylthio groups including those moieties having one or more thioether linkages and from 1 to about 12 carbon atoms or from 1 to about 6 carbon atoms; alkylsulphinyl groups including those moieties having one or more sulphinyl linkages and from 1 to about 12 carbon atoms or from 1 to about 6 carbon atoms; alkylsulphonyl groups including those moieties having one or more sulphonyl linkages and from 1 to about 12 carbon atoms or from 1 to about 6 carbon atoms; aminoalkyl groups such as groups having one or more N atoms and from 1 to about 12 carbon atoms or from 1 to about 6 carbon atoms; carbocylic aryl having 6 or more carbons, particularly phenyl (e.g., R being a substituted or unsubstituted biphenyl moiety); and aralkyl such as benzyl.

Preferably excluded from the scope of the present invention are the known compounds Variolin A, Variolin B, Variolin D, N(3') methyl tetrahydrovariolin B, and deoxyvariolin B.

The compounds of the present invention can be prepared synthetically using the methodology described in WO 0204447 in which the core variolin skeleton is constructed from simple monoheteroaromatic starting materials, based on the following retrosynthesis.

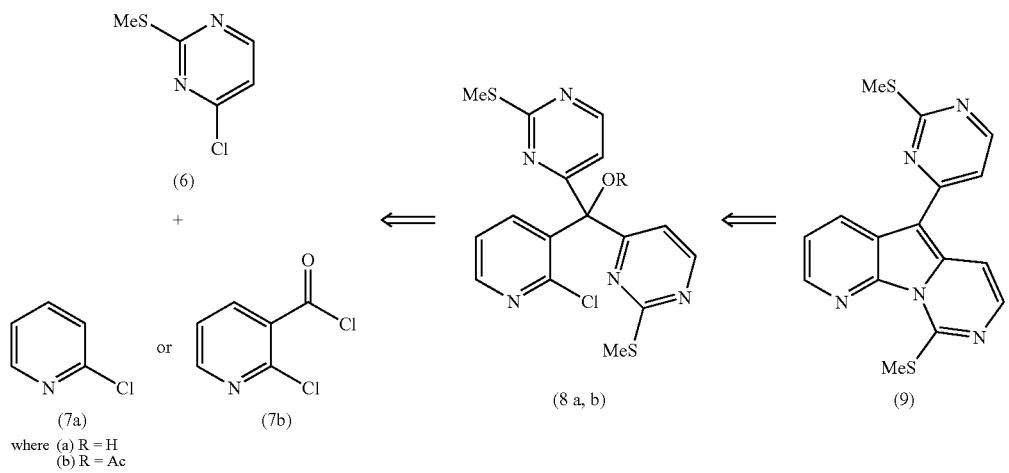

where (a) R = H
(b) R = Ac

Dependent on the choice of the mono heteroaromatic starting materials (6) and (7), the methodology can be readily broadened to provide access to a wide range of variolin analogs as exemplified herein.

WO 0212240 also provides guidance on the synthesis of variolin compounds.

Thus the present invention also provides synthetic routes to the compounds of this invention.

Antitumoral activities of these compounds include leukaemia, lung cancer, colon cancer, kidney cancer, cancer of the cervix, prostate cancer, ovarian cancer, pancreatic cancer, endothelial cancer, breast cancer, sarcoma and melanoma.

Thus, the present invention provides a method of treating any mammal, notably a human, affected by cancer which comprises administering to the affected individual a therapeutically effective amount of a compound of the invention, or a pharmaceutical composition thereof.

Another especially preferred embodiment of the present invention is pharmaceutical compositions useful as antitumor agents which contain as active ingredient a compound or compounds of the invention, as well as the processes for their preparation.

Examples of pharmaceutical compositions include any solid (tablets, pills, capsules, granules etc) or liquid (solutions, suspensions or emulsions) with suitable composition or oral, topical or parenteral administration.

Administration of the compounds or compositions of the present invention may be any suitable method, such as intravenous infusion, oral preparation, intraperitonal and intravenous preparation.

DETAILED DESCRIPTION OF THE PREFERRED EMBODIMENTS $R_1$ is preferably hydrogen, alkyl or halogen; more preferably hydrogen, methyl or chloro. Alternatively $R_1$ with $R_2$ preferably form a fused ring, more preferably a fused aromatic ring, and most preferably a fused benzene ring. Such a ring can have substituents, for example OR', NR'$_2$ or halogen; more preferably hydroxy, alkoxy, amino, or halogen; most preferably hydroxy, methoxy, amino, fluoro or chloro.

$R_2$ is preferably hydrogen or halogen; more preferably hydrogen, fluoro or chloro. As mentioned, alternatively $R_1$ with $R_2$ preferably form a fused ring.

$R_3$ is preferably hydrogen, OR', NR'$_2$ or halogen; more preferably hydrogen, hydroxy, alkoxy, protected hydroxy, amino, protected amino or halogen; most preferably hydrogen, hydroxy, methoxy, benzyloxy, amino, methoxybenylamino or chloro.

It seems that higher activity is obtained when $R_3$ is hydrogen, followed by hydroxy, halogen (chloro), methoxy, amino.

$R_4$ is preferably hydrogen.

$R_5$ is preferably hydrogen.

$R_6$ is preferably hydrogen.

$R_7$ is preferably hydrogen.

$R_{12}$ is preferably alkyl, aryl or heteroaryl; more preferably alkyl, phenyl or heteroaryl with 5 or 6 ring atoms and 1 or 2 heteratoms; most preferably isopropyl, phenyl, pyrimidinyl, thiophenyl or pyridinyl. The aryl or heteroaryl groups are unsubstituted or have preferred substituents chosen from OR', especially alkoxy such as methoxy, or nitro, and when pyrimidinyl may have the indicated substituent $X_1$.

It seems that higher activity is obtained when $R_{12}$ is 4-pyrimidinyl, as in the formula (5a).

$X_1$ is preferably hydrogen, alkyl, OR', NR'$_2$, SR', SOR', SO$_2$R', carboxyalkyl or aralkyl; more preferably hydrogen, alkyl, hydroxy, alkoxy, aryloxy, amino, protected amino, thioalkyl, alkylsulphinyl, alkylsulphonyl, or dicarboxyalkyl; most preferably hydrogen, methyl, hydroxy, methoxy, ethoxy, benzyloxy, phenoxy, amino, methoxybenzylamino, thiomethyl, methylsulphinyl, methylsulphonyl or dimethylcarboxyethyl.

It seems that when $X_1$ is SR', SOR', SO$_2$R', there is high selectivity for cancer of the cervix. In tests against the Hela cell line, the activity was increased by 2 or 3 orders of magnitude. In particular, $X_1$ is preferably Salkyl, SOalkyl or SO$_2$alkyl, where alkyl is usually methyl.

$X_2$ is preferably NR'$_2$ or SR'; more preferably NH$_2$ or thioalkyl; most preferably NH$_2$ or thiomethyl.

Thus, preferred compounds of this invention are of formula (5) where the substituents conform with one or more, preferably all of these preferred, more preferred or most preferred definitions.

Especially preferred embodiments of the present invention are the variolin-like compounds with the general structures (10), (11) and (29).

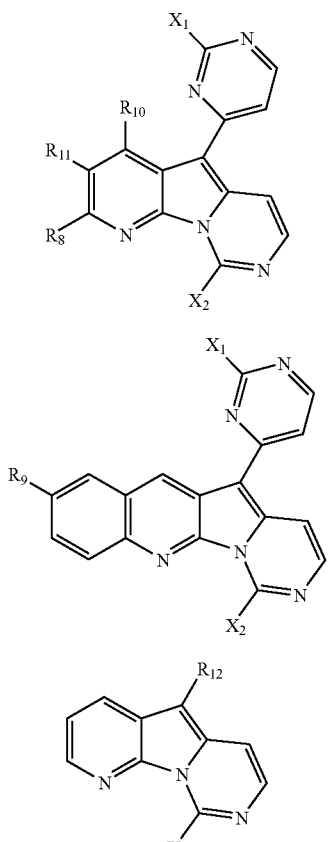

(10)

(11)

(29)

wherein the substituent groups defined by $X_1$, and $X_2$ are each independently selected from the group consisting of H, OH, OR', SH, SR', SOR', SO$_2$R', NO$_2$, NH$_2$, NHR', N(R')$_2$, NHCOR', NHSO$_2$R', CN, halogen, =O, C(=O)H, C(=O)R', CO$_2$H, CO$_2$R', carboxyalkyl, $C_1$-$C_{12}$ alkyl, $C_2$-$C_{12}$ alkenyl, $C_2$-$C_{12}$ alkynyl, substituted or unsubstituted aryl, substituted or unsubstituted aralkyl and substituted or unsubstituted heteroaromatic; but are most preferably NH$_2$, SMe, SOMe, or SO$_2$Me.

wherein $R_8$ is selected from the group consisting of H, OH, OR', SH, SR', SOR', SO$_2$R', NO$_2$, NH$_2$, NHR', N(R')$_2$, NHCOR', NHSO$_2$R', CN, halogen, =O, C(=O)H, C(=O)R', CO$_2$H, CO$_2$R', $C_1$-$C_{12}$ alkyl, $C_2$-$C_{12}$ alkenyl, $C_2$-$C_{12}$ alkynyl, substituted or unsubstituted aryl, substituted or unsubstituted aralkyl and substituted or unsubstituted heteroaromatic; but is most preferably H, methyl or Cl.

wherein $R_9$ is selected from the group consisting of H, OH, OR', SH, SR', SOR', SO$_2$R', NO$_2$, NH$_2$, NHR', N(R')$_2$, NHCOR', NHSO$_2$R', CN, halogen, =O, C(=O)H, C(=O)R', CO$_2$H, CO$_2$R', $C_1$-$C_{12}$ alkyl, $C_2$-$C_{12}$ alkenyl, $C_2$-$C_{12}$ alkynyl, substituted or unsubstituted aryl, substituted or unsubstituted aralkyl and substituted or unsubstituted heteroaromatic; but is most preferably H or OMe.

wherein $R_{10}$ is selected from the group consisting of H, OH, OR', SH, SR', SOR', SO$_2$R', NO$_2$, NH$_2$, NHR', N(R')$_2$, NHCOR', NHSO$_2$R', CN, halogen, =O, C(=O)H, C(=O)R', CO$_2$H, CO$_2$R', $C_1$-$C_{12}$ alkyl, $C_2$-$C_{12}$ alkenyl, $C_2$-$C_{12}$ alkynyl, substituted or unsubstituted aryl, substituted or unsubstituted aralkyl and substituted or unsubstituted heteroaromatic; but is most preferably H, OH, Cl, F, NH$_2$ or OMe.

wherein $R_{11}$ is selected from the group consisting of H, OH, OR', SH, SR', SOR', SO$_2$R', NO$_2$, NH$_2$, NHR', N(R')$_2$, NHCOR', NHSO$_2$R', CN, halogen, =O, C(=O)H, C(=O)R', CO$_2$H, CO$_2$R', $C_1$-$C_{12}$ alkyl, $C_2$-$C_{12}$ alkenyl, $C_2$-$C_{12}$ alkynyl, substituted or unsubstituted aryl, substituted or unsubstituted aralkyl and substituted or unsubstituted heteroaromatic; but is most preferably H, Cl or F.

wherein $R_{12}$ is selected from the group consisting of H, OH, OR', SH, SR', SOR', SO$_2$R', NO$_2$, NH$_2$, NHR', N(R')$_2$, NHCOR', NHSO$_2$R', CN, halogen, =O, C(=O)H, C(=O)R', CO$_2$H, CO$_2$R', $C_1$-$C_{12}$ alkyl, $C_2$-$C_{12}$ alkenyl, $C_2$-$C_{12}$ alkynyl, substituted or unsubstituted aryl, substituted or unsubstituted aralkyl and substituted or unsubstituted heteroaromatic; but is most preferably alkyl, substituted or unsubstituted aryl, or substituted or unsubstituted heteroaromatic; and is yet more preferably alkyl, substituted or unsubstituted phenyl, or substituted or unsubstituted thiophenyl, pyidinyl or pyrimidinyl, with preferred substituents including alkoxy or nitro, especially methoxy or nitro, together with the permitted defintions for the group $X_1$.

wherein each of the R' groups is independently selected from the group consisting of H, OH, SH, NO$_2$, NH$_2$, CN, halogen, =O, C(=O)H, C(=O)CH$_3$, CO$_2$H, CO$_2$CH$_3$, $C_1$-$C_{12}$ alkyl, $C_2$-$C_{12}$ alkenyl, $C_2$-$C_{12}$ alkynyl, aryl, aralkyl and heteroaromatic.

Particular embodiments of the compounds of formula (10) include those wherein one or more of the subsitutents are as follows:

$X_1$ is as defined, including preferred, more preferred and most preferred options;

$X_2$ is as defined, including preferred, more preferred and most preferred options;

$R_8$ is as defined for $R_1$, including preferred, more preferred and most preferred options;

$R_{10}$ is as defined for $R_3$, including preferred, more preferred and most preferred options;

$R_{11}$ is as defined for $R_2$, including preferred, more preferred and most preferred options.

Particular embodiments of the compounds of formula (11) include those wherein one or more of the substituents are as follows:

$X_1$ is as defined, including preferred, more preferred and most preferred options;

$X_2$ is as defined, including preferred, more preferred and most preferred options;

$R_9$ is one of the permittted substituents for an aryl ring, such as hydrogen or alkoxy, preferably hydrogen or methoxy.

Particular embodiments of the compounds of formula (29) include those wherein one or more of the subsitutents are as follows:

$X_2$ is as defined;

$R_{12}$ is not pyrimidinyl and is preferably alkyl, aryl or heteroaryl except for pyrimidinyl; more preferably alkyl, phenyl or heteroaryl with 5 or 6 ring atoms and 1 or 2 heteratoms; most preferably isopropyl, phenyl, thiophenyl or pyridinyl. The aryl or heteroaryl groups are unsubstituted or have preferred substituents chosen from OR', especially alkoxy such as methoxy, or nitro.

Compounds of the general formulae (10), (11) and (29) can be prepared synthetically using modifications of the methodology described in WO 0204447 and WO 0212240.

Some of the preferred methods of producing the compounds of this invention are described below in the following reaction schemes with examples of typical substituent groups. These typical substituents are not limiting of the invention and the process is to be understood in the more general sense, without special regard to the identities indicated by the code letters.

Many active antitumoral compounds have been prepared from these compounds and it is believed that many more compounds can be formed in accordance with the teachings of the present disclosure.
The preparation of compounds of general formula (11) is illustrated below for $R_9$ as H or OMe.
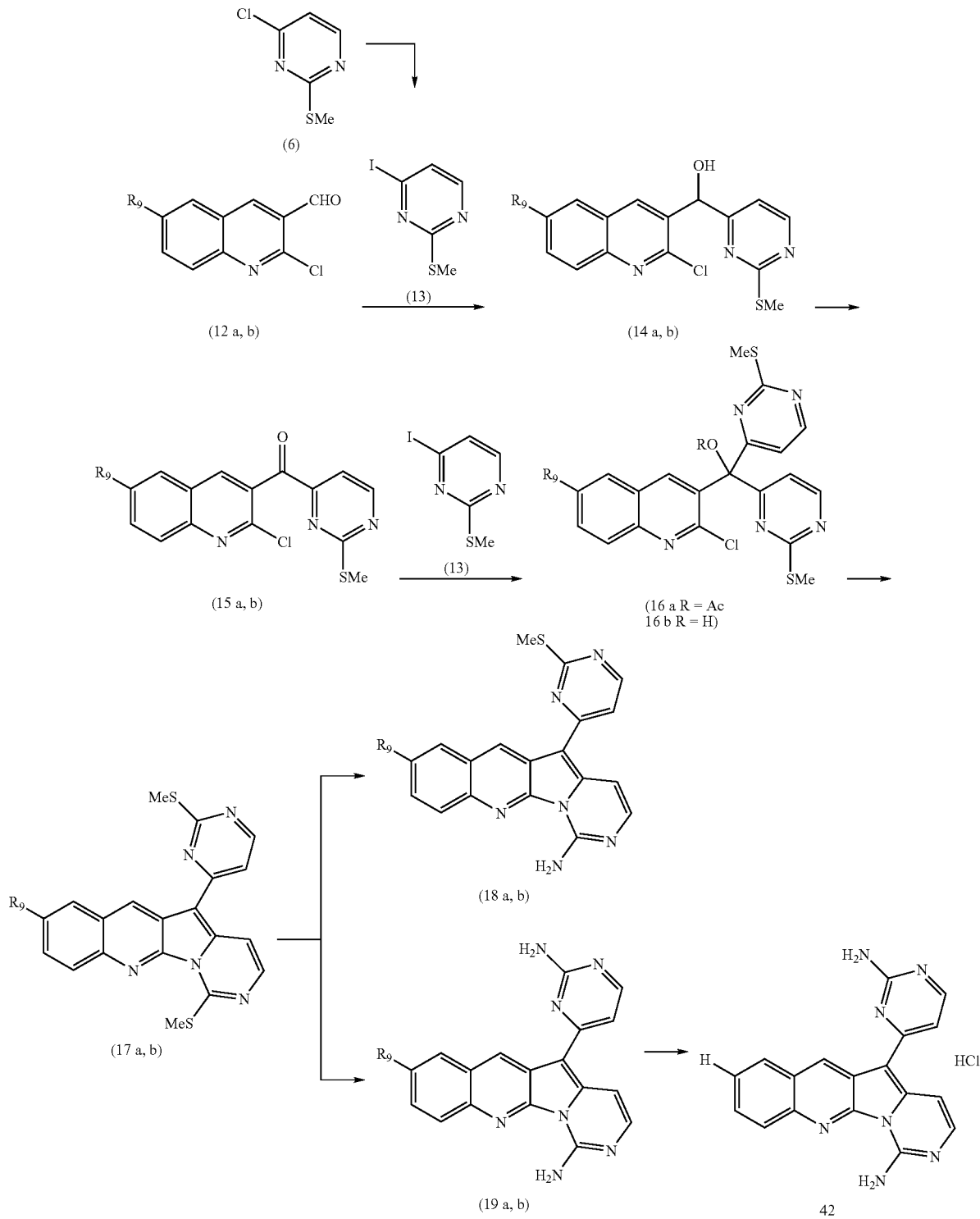
where (a) $R_9$ = H
(b) $R_9$ = OMe The preparation of compounds of general formula (10) is illustrated for the case where $R_8$ is methyl, and $R_{10}$ and $R_{11}$ are H.
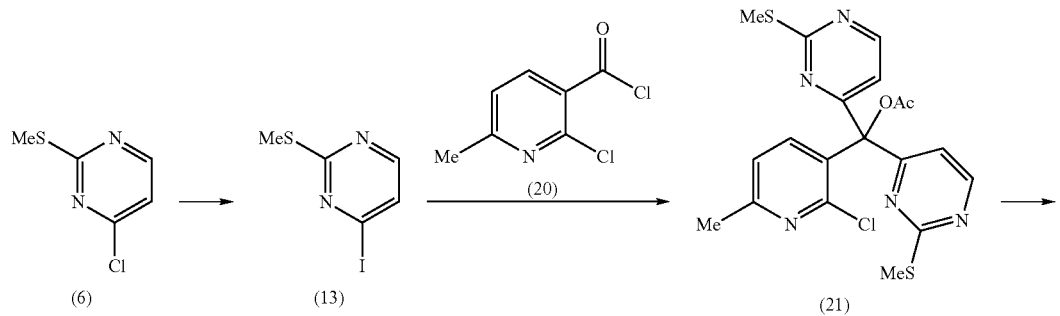
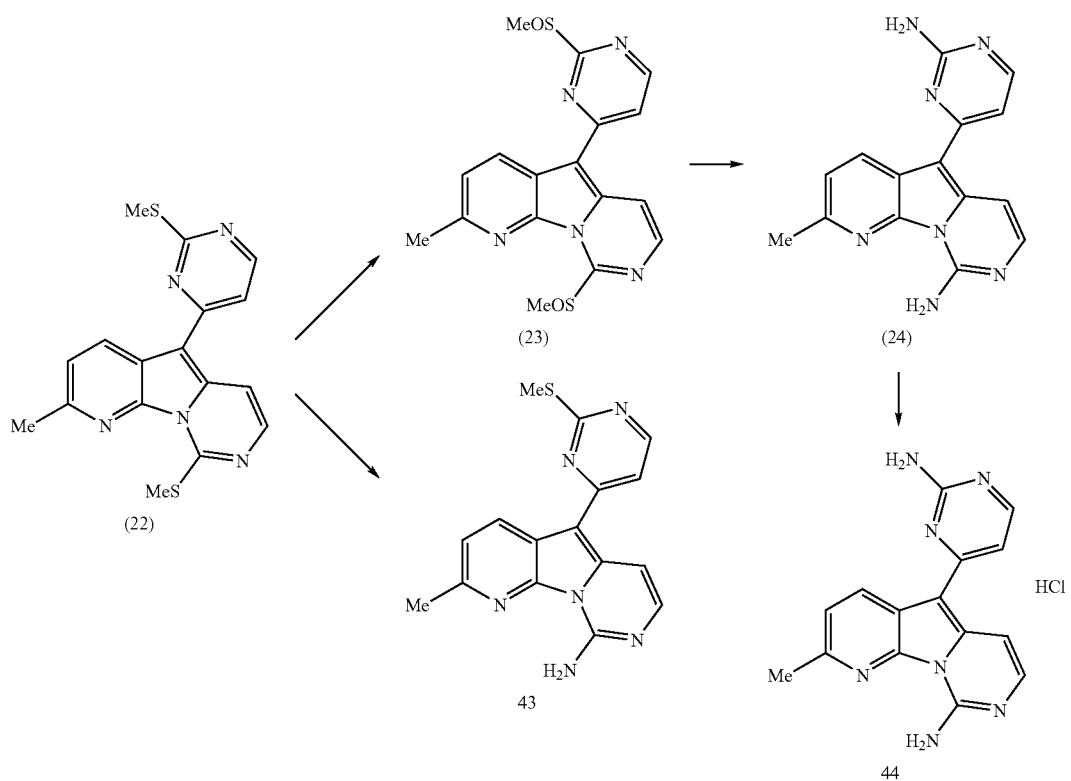

The preparation of compounds of general formula (10) is illustrated for the case where $R_8$ is H or Cl, $R_{10}$ is H and $R_{11}$ is F or Cl.

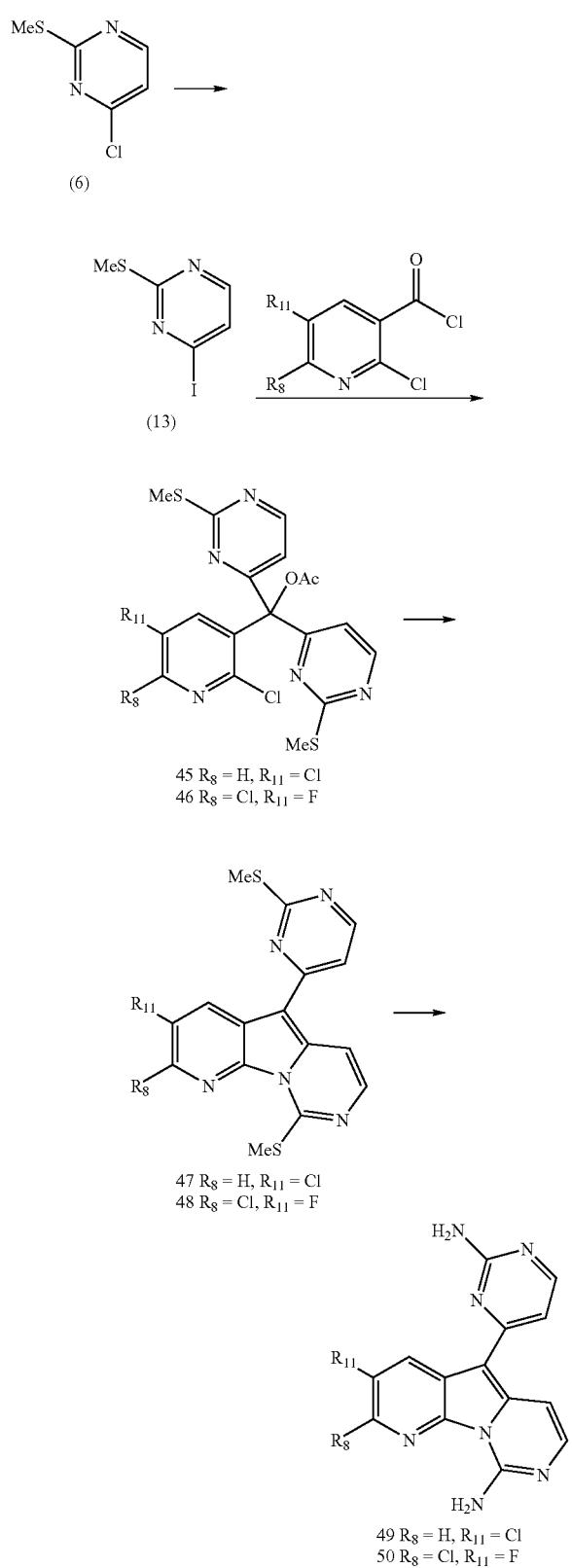

45 $R_8$ = H, $R_{11}$ = Cl
46 $R_8$ = Cl, $R_{11}$ = F

47 $R_8$ = H, $R_{11}$ = Cl
48 $R_8$ = Cl, $R_{11}$ = F

49 $R_8$ = H, $R_{11}$ = Cl
50 $R_8$ = Cl, $R_{11}$ = F

The preparation of compounds of general formula (10) is illustrated for the case where $R_8$, $R_{10}$ and $R_{11}$ are H.

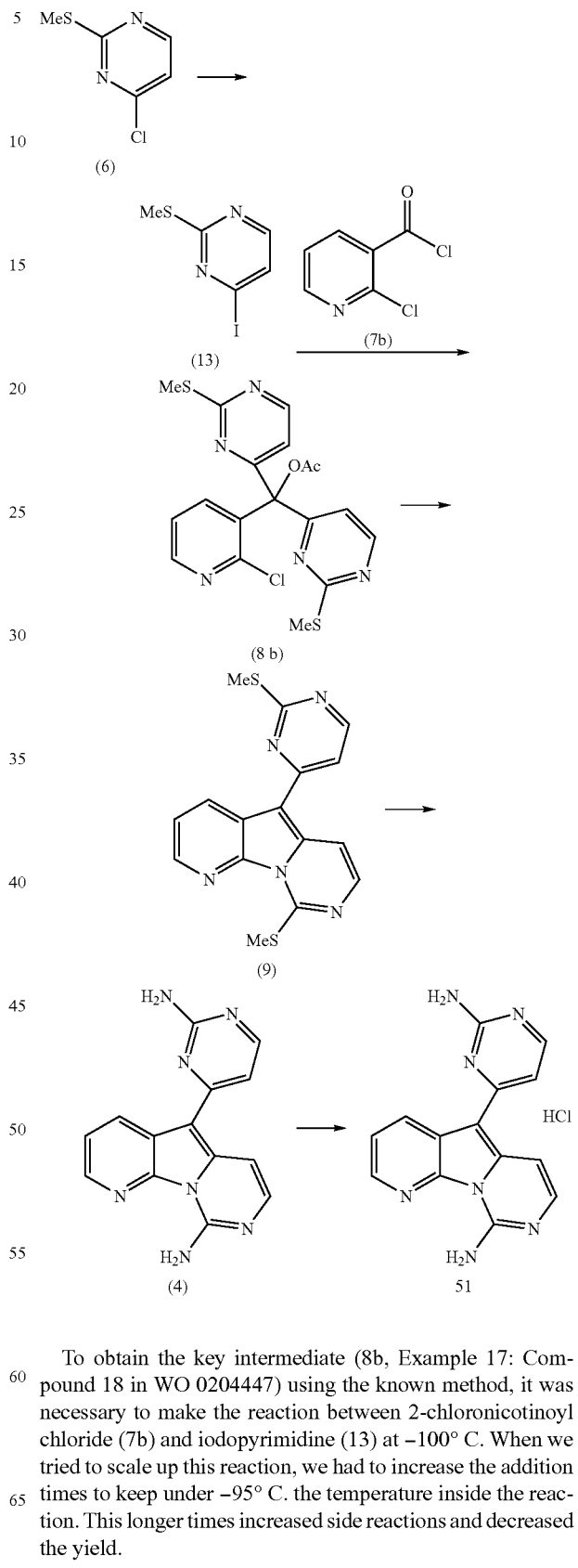

To obtain the key intermediate (8b, Example 17: Compound 18 in WO 0204447) using the known method, it was necessary to make the reaction between 2-chloronicotinoyl chloride (7b) and iodopyrimidine (13) at −100° C. When we tried to scale up this reaction, we had to increase the addition times to keep under −95° C. the temperature inside the reaction. This longer times increased side reactions and decreased the yield.

In order to avoid this extremely low temperature in the formation of (8b) we developed a new route to obtain (8b). Thus (7b) was converted into the correspond Weinreb amide (30) which reacted with the magnesium derivative of (13) at −5° C. to afford the ketone (31). Transformation of (30) into (8b) was done with two methods: a) with the magnesium derivative of (13) at 0° C. or b) with lithium derivative of (13) into Barbier's conditions at −78° C. In both methods, the reaction is easily scaled up and the yields are better than the original method.

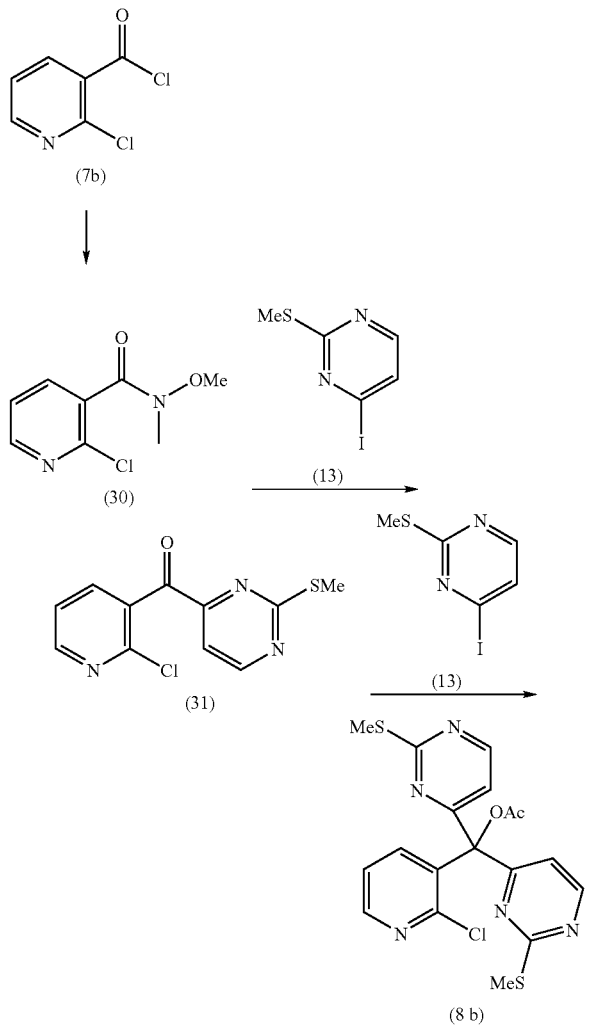

Reflecting this discovery, the present invention provides a process for preparing a variolin intermediate of formula (8z):

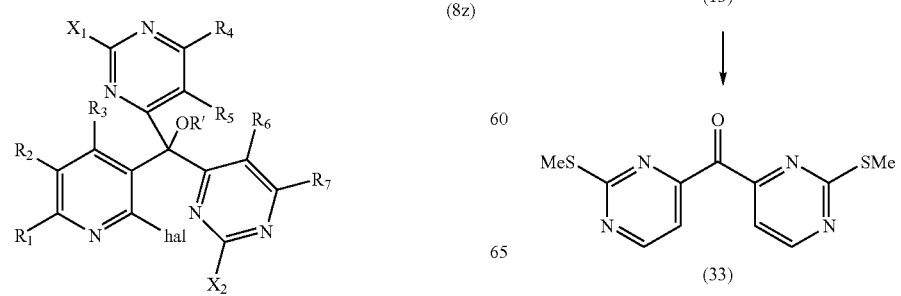

where hal is a halogen, and the remaining substituents are as previously defined; which comprises reacting a compound of formula (31z):

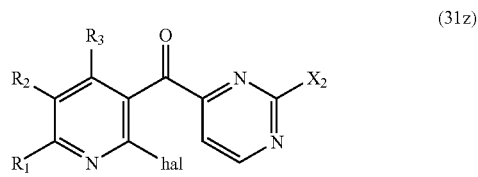

where the substituents are as previously defined, with a compound of formula (13z):

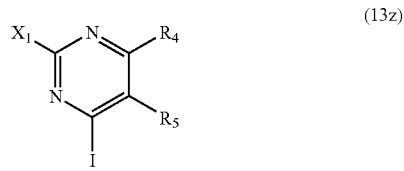

where the substituents are as previously defined.

In this reaction, $X_1$ and $X_2$ can be the same or different and are preferably both —SMe; hal is usually Cl; R' is typically H or Ac, and the remaining substituents are ordinarily H or as for preferred compounds of this invention.

The compound of formula (31z) is suitably made by reacting a compound of formula (30z):

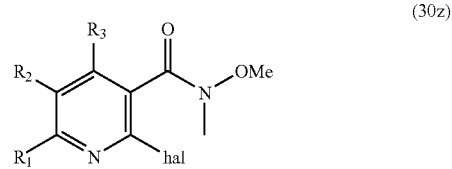

where the substituents are as previously defined, with a compound of the formula (13z). The compound of formula (13z) employed to react with the compound of formula (30z) may be the same as or different to the compound of formula (13z) employed to react with the compound of formula (31 z).

The preparation of compounds of general formula (10) is illustrated for the case where $R_8$ and $R_{11}$ are H and $R_{10}$ is OBn.

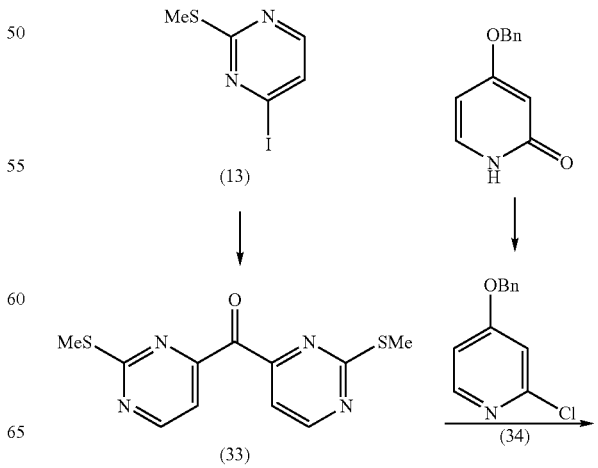

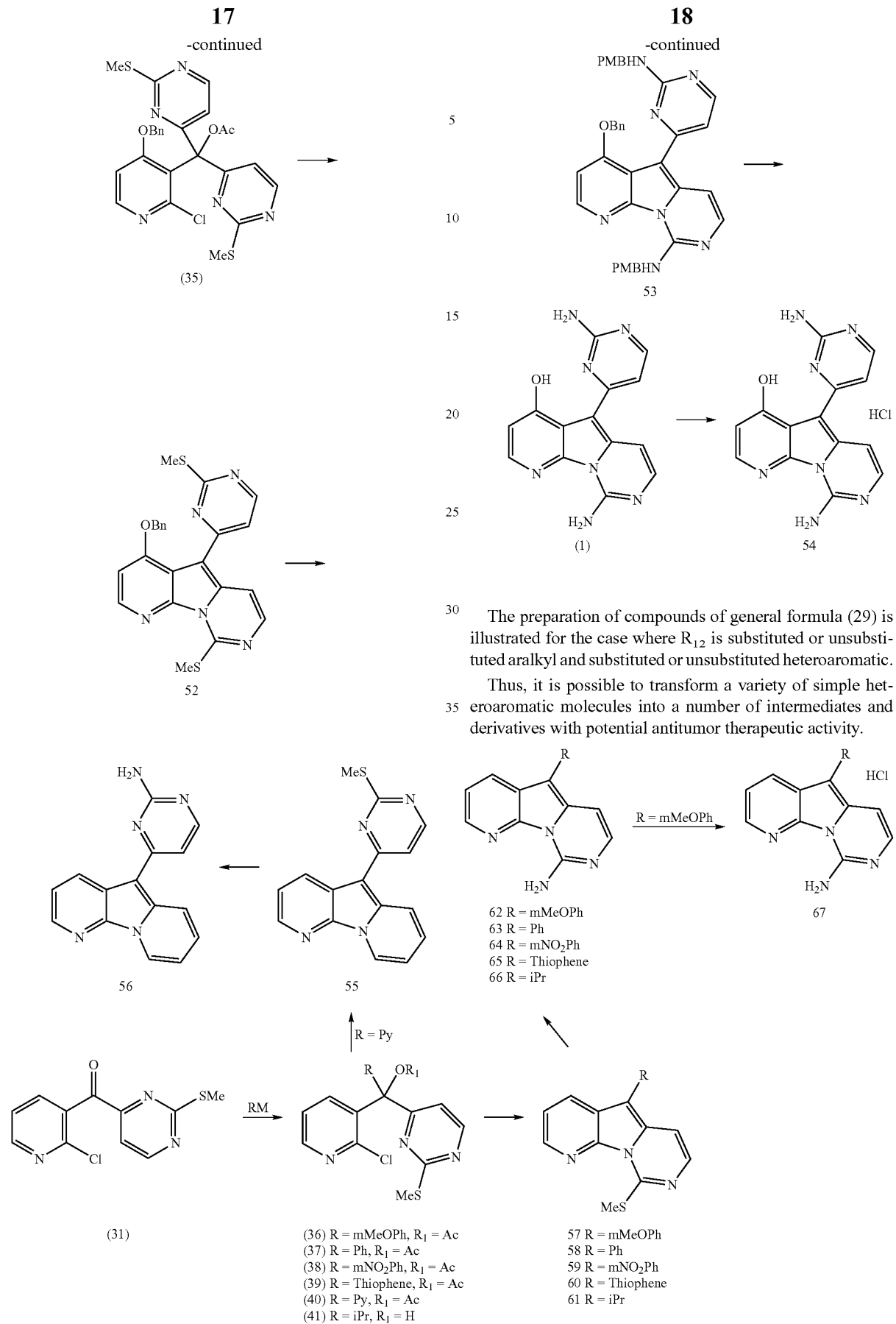
The preparation of compounds of general formula (29) is illustrated for the case where $R_{12}$ is substituted or unsubstituted aralkyl and substituted or unsubstituted heteroaromatic.
Thus, it is possible to transform a variety of simple heteroaromatic molecules into a number of intermediates and derivatives with potential antitumor therapeutic activity.

For compounds of general formula (10) and (11), a variety of simple functional group interconversions gives access to a wide variety of further derivatives with different substituents $X_1$, $X_2$ and $R_{10}$ as illustrated below.
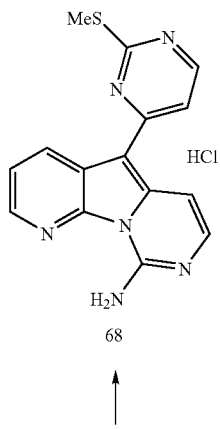
68
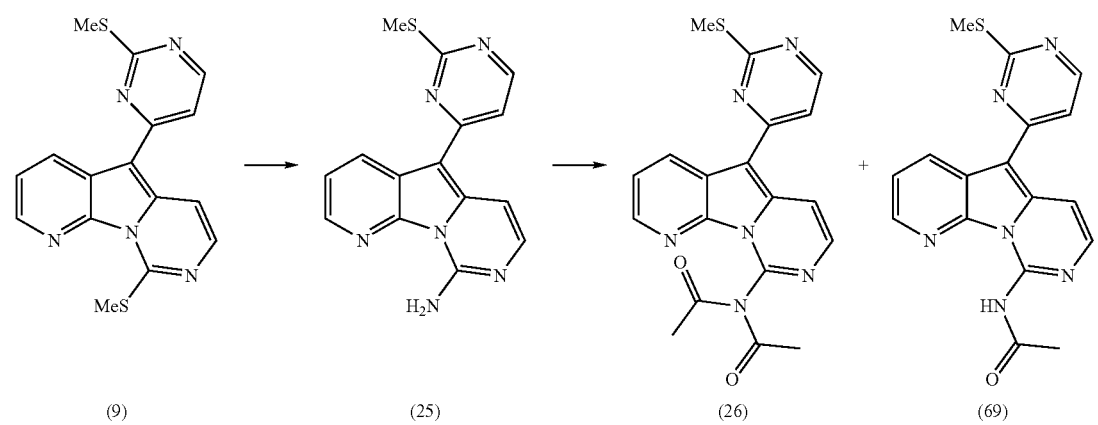
(9)  (25)  (26)  (69)
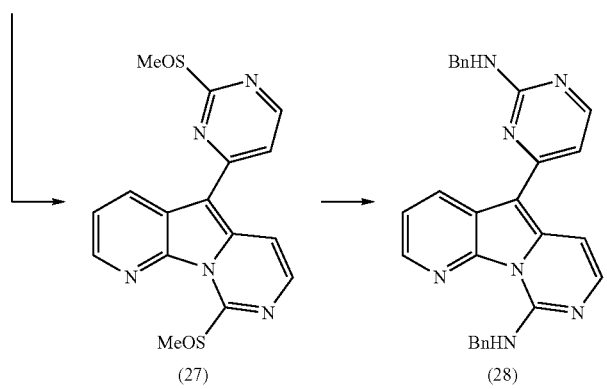
(27)  (28)

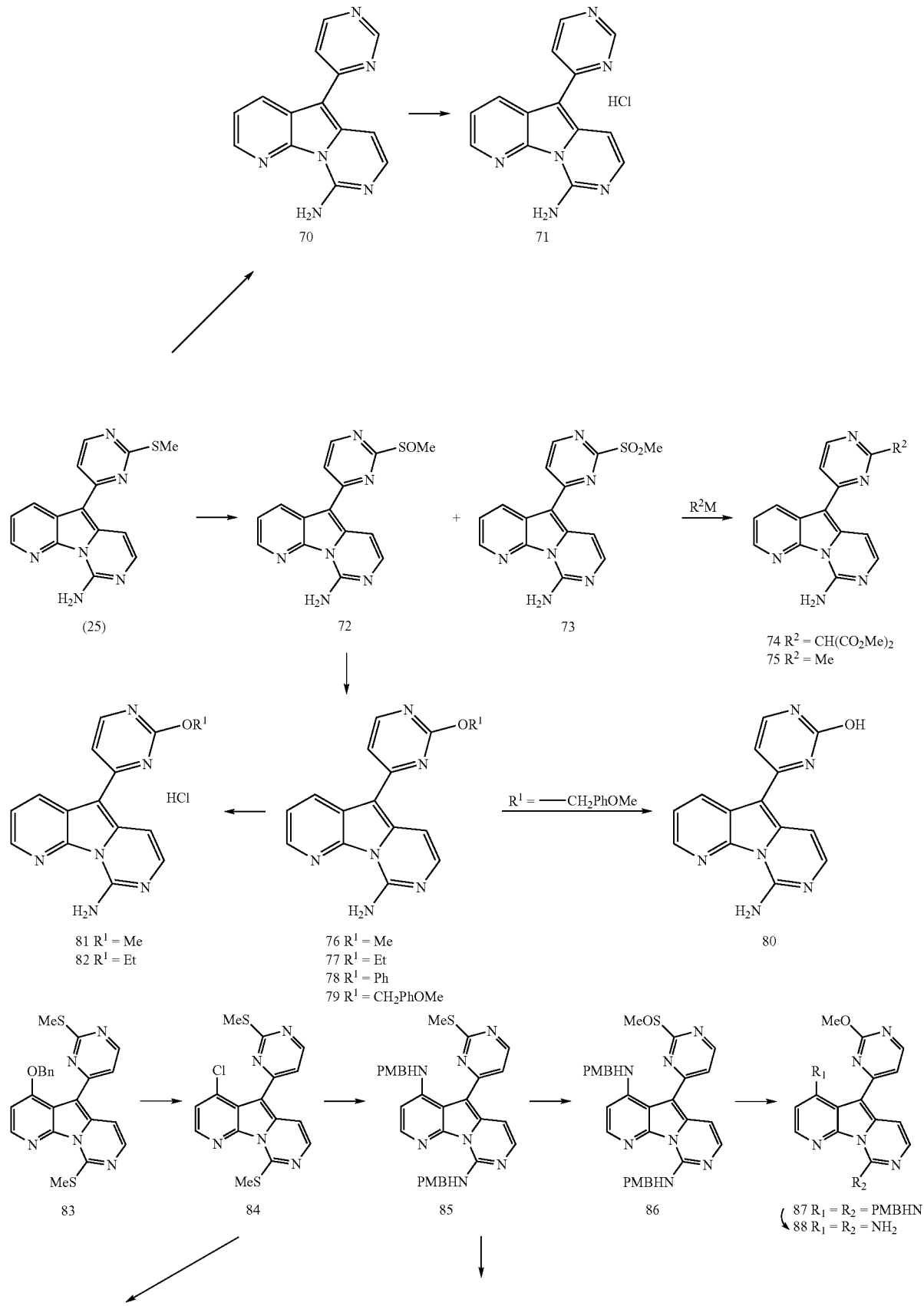

-continued
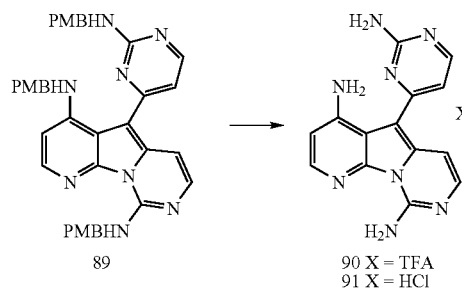
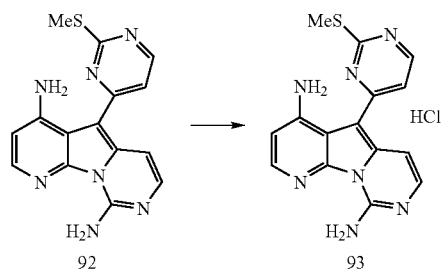
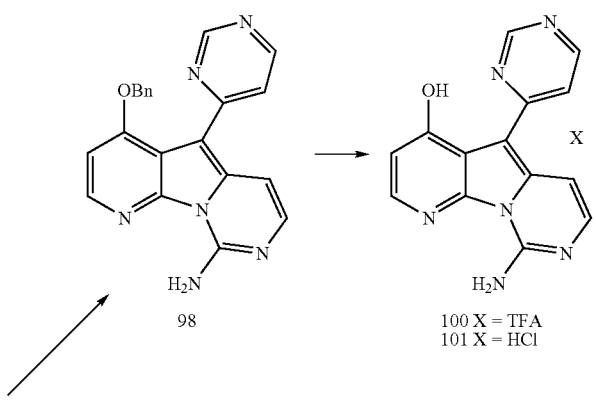
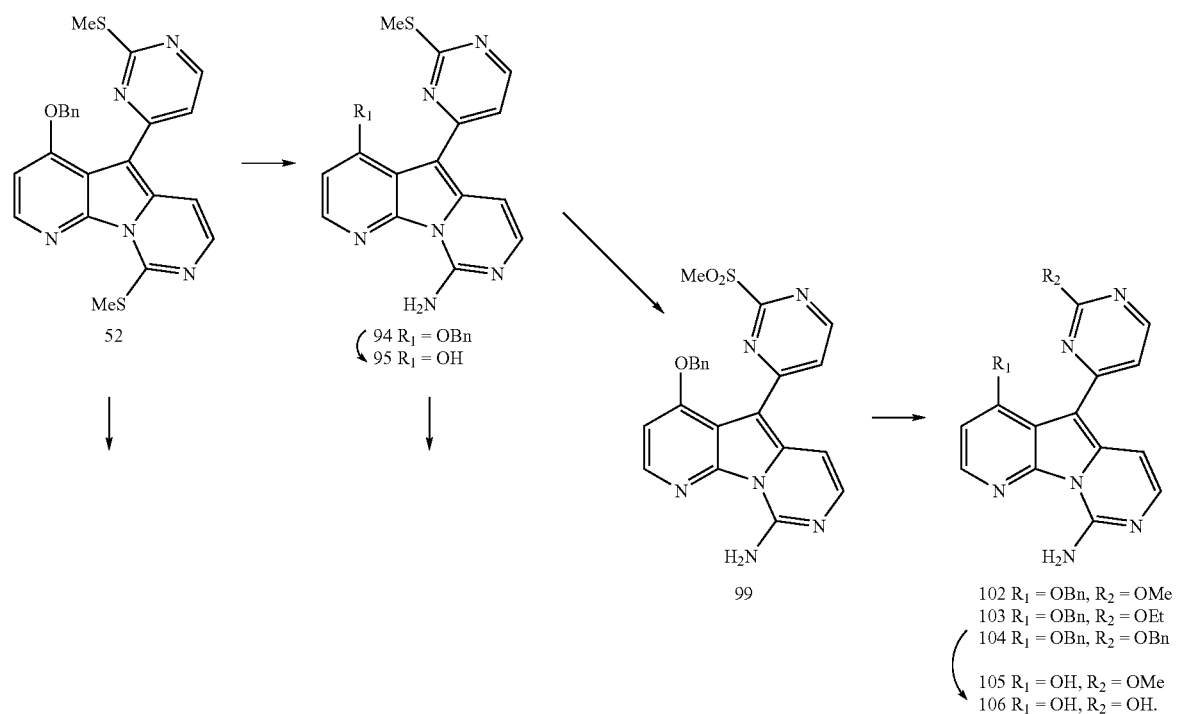

-continued
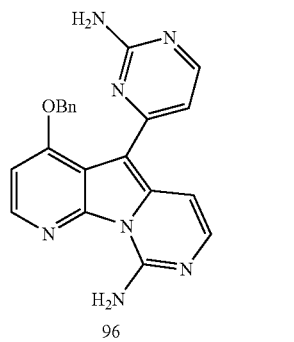
96
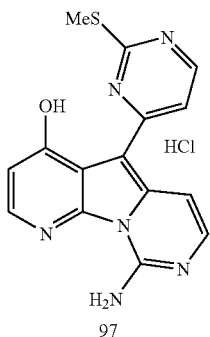
97
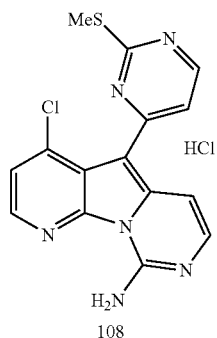
108
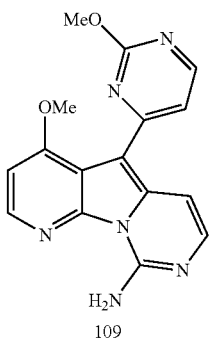
109
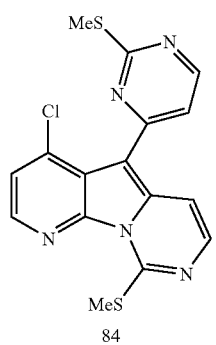
84
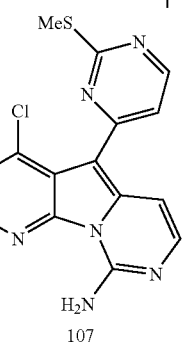
107
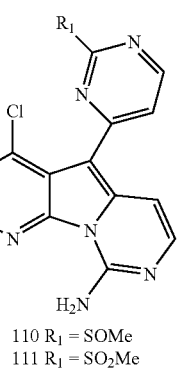
110 R₁ = SOMe
111 R₁ = SO₂Me
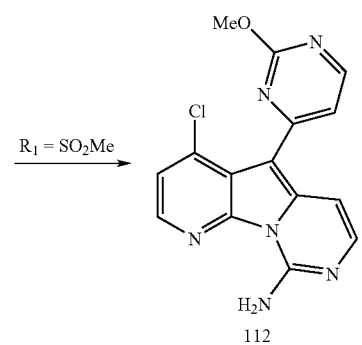
112
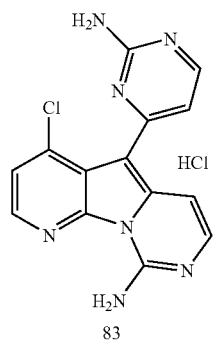
83
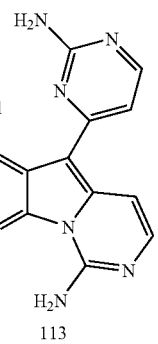
113
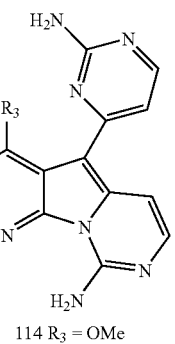
114 R₃ = OMe
115 R₃ = F
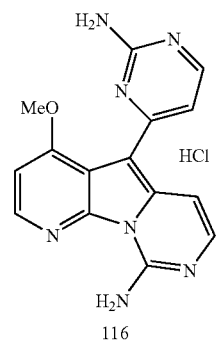
116

Examples of biological activities of the compounds of the present invention are included in table I at the end of the document.

The present application claims priority of a GB patent application. We expressly incorporate herein by reference any disclosure in the specification of that GB patent application which is not contained in the present specification.

The experimental procedures and the physicochemical characteristics of the compounds are the following:

General Experimental Details

Unless otherwise stated, all reactions were performed under an argon atmosphere in pre-dried glassware.

EXAMPLE 1

Compound 13

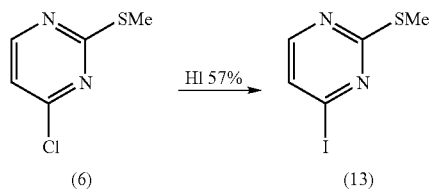

Iodopyrimidine (13) was prepared following the experimental procedure described in the literature by A. J. Majeed et al. *Tetrahedron* 1989, 45, 993.

EXAMPLE 2

Compound 14a

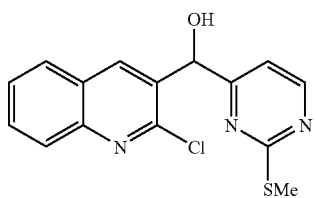

Method A

A solution of 4-iodo-2-methylthiopyrimidine 13 (5.13 g, 20.3 mmol) in tetrahydrofuran (75 mL) was treated at −100° C. with n-BuLi (8.1 mL, 20.3 mmol, 2.5 M in hexanes). The reaction mixture was stirred at −100° C. for 45 min and treated with a solution of 2-chloro-3-quinolinecarboxaldehyde 12a (3.0 g, 15.7 mmol) in tetrahydrofuran (60 mL) at −100° C. for 2.5 h. The reaction was quenched with a saturated aqueous solution of ammonium chloride, warmed to 23° C. and partitioned between ethyl acetate and saturated aqueous solution of ammonium chloride. The organic layer was dried over sodium sulphate, filtered, and evaporated. The crude was chromatographed (hexane:ethyl acetate, from 4:1 to 1:1) to give 14a as a yellow solid (4.0 g, 81%).

$^1$H NMR (CDCl$_3$, 300 MHz) δ 8.45 (d, J=7.8 Hz, 1H), 8.25 (s, 1H), 8.02 (d, J=8.3 Hz, 1H), 7.81 (d, J=8.0 Hz, 1H), 7.74 (t, J=7.3 Hz, 1H), 7.56 (t, J=7.0 Hz, 1H), 7.02 (d, J=7.8 Hz, 1H), 6.24 (d, J=4.1 Hz, 1H), 4.91 (d, J=4.2 Hz, 1H, OH), 2.58 (s, 3H).

$^{13}$C NMR (CDCl$_3$, 75 MHz) δ 172.4, 169.5, 157.9, 149.4, 147.0, 138.0, 133.9, 130.9, 127.9, 127.9, 127.4, 127.2, 113.5, 71.7, 14.2.

MS (ESI) m/z: 318 (M+1)$^+$.

Rf: 0.12 (hexane:ethyl acetate, 4:1).

Method B

A solution of 4-iodo-2-methylthiopyrimidine 13 (5.1 g, 20.3 mmol) in toluene (40 mL) was treated at 0° C. with i-PrMgCl (10 mL, 20.0 mmol, 2 M in tetrahydrofuran) for 1 h and added via canula to a solution of 2-chloro-3-quinolinecarboxaldehyde 12a (3.0 g, 15.7 mmol) in toluene (150 mL) at 0° C. The reaction mixture was stirred at 0° C. for 16 h, quenched with a saturated aqueous solution of ammonium chloride, warmed to 23° C. and partitioned between saturated aqueous solution of ammonium chloride and ethyl acetate. The organic layer was dried over sodium sulphate, filtered, and evaporated. The residue was chromatographed (hexane:ethyl acetate, from 4:1 to 1:1) to give 14a as a yellow solid (3.5 g, 70%).

EXAMPLE 3

Compound 14b

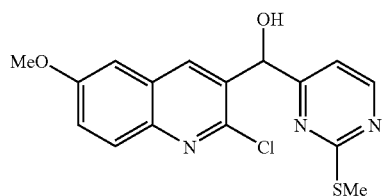

A solution of 4-iodo-2-methylthiopyrimidine 13 (3.4 g, 13.5 mmol) in tetrahydrofuran (60 mL) was treated at −100° C. with n-BuLi (5.4 mL, 2.5 M in hexane, 13.5 mmol) and stirred at −100° C. for 45 min. Afterwards, a solution of 2-chloro-6-methoxy-3-quinoline-carboxaldehyde 12b (1.7 g, 7.9 mmol) in tetrahydrofuran (35 mL) was added at −100° C. and stirred for 2.5 h. The reaction was quenched with a saturated aqueous solution of ammonium chloride, warmed to 23° C. and partitioned between ethyl acetate and saturated aqueous solution of ammonium chloride. The organic layer was dried over sodium sulphate, filtered, and evaporated. The residue was chromatographed (hexane:ethyl acetate, from 4:1 to 3:1) to give 14b as a yellow solid (1.8 g, 67%).

$^1$H NMR (CDCl$_3$, 300 MHz) δ 8.42 (dd, J=5.1, 1.0 Hz, 1H), 8.11 (s, 1H), 7.86 (d, J=9.3 Hz, 1H), 7.34 (dd, J=9.3, 2.7 Hz, 1H), 7.03 (d, J=5.1 Hz, 1H), 7.00 (d, J=2.7 Hz, 1H), 6.20 (br s, 1H), 5.09 (br s, 1H), 3.87 (s, 3H), 2.53 (br s, 3H).

$^{13}$C NMR (CDCl$_3$, 75 MHz) δ 172.7, 168.4, 158.6, 157.9, 146.6, 143.5, 136.8, 133.6, 129.7, 128.6, 123.9, 113.5, 105.3, 71.2, 55.8, 14.4.

MS (ESI) m/z: 370 (M+23)$^+$.

Rf: 0.37 (hexane:ethyl acetate, 1:1).

EXAMPLE 4

Compound 15a

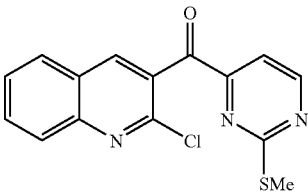

A solution of 14a (4.0 g, 12.6 mmol) with PDC (7.1 g, 18.9 mmol) in CH$_2$Cl$_2$ (50 mL) was stirred at 23° C. for 24 h. The reaction mixture was filtered through Celite, evaporated and chromatographed (hexane:ethyl acetate, 4:1) to give 15a as a white solid (3.0 g, 75%).

$^1$H NMR (CDCl$_3$, 300 MHz) δ 8.85 (d, J=4.9 Hz, 1H), 8.42 (s, 1H), 8.11 (d, J=8.5 Hz, 1H), 7.93 (d, J=8.1 Hz, 1H), 7.88 (t, J=7.1 Hz, 1H), 7.69 (d, J=4.9 Hz, 1H), 7.66 (t, J=7.1 Hz, 1H), 2.35 (s, 3H).

$^{13}$C NMR (CDCl$_3$, 75 MHz) δ 192.7, 173.7, 159.7, 159.3, 148.3, 146.8, 140.6, 132.6, 131.2, 128.8, 128.6, 128.1, 126.1, 113.7, 14.3.

MS (ESI) m/z: 280 (M−35)$^+$.

Rf: 0.23 (hexane:ethyl acetate, 4:1).

EXAMPLE 5

Compound 15b

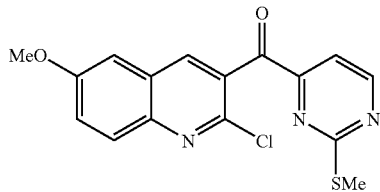

A solution of 14b (1.8 g, 5.2 mmol) in CH$_2$Cl$_2$ (50 mL) was treated with PDC (2.9 g, 7.8 mmol) at 23° C. for 48 h. The reaction mixture was filtered through Celite, concentrated and chromatographed (hexane:ethyl acetate, 3:1) to give 15b as a white solid (1.5 g, 82%).

$^1$H NMR (CDCl$_3$, 300 MHz) δ 8.82 (d, J=4.9 Hz, 1H), 8.27 (s, 1H), 7.97 (d, J=9.3 Hz, 1H), 7.66 (d, J=4.9 Hz, 1H), 7.47 (dd, J=9.3, 2.9 Hz, 1H), 7.13 (d, J=2.7 Hz, 1H), 3.93 (s, 3H), 2.34 (s, 3H).

$^{13}$C NMR (CDCl$_3$, 75 MHz) δ 193.0, 173.7, 159.6, 159.4, 158.9, 144.4, 144.2, 139.2, 131.3, 130.1, 127.3, 125.2, 113.7, 105.9, 55.9, 14.3.

MS (ESI) m/z: 368 (M+23)$^+$.

Rf: 0.26 (hexane:ethyl acetate, 3:1).

EXAMPLE 6

Compound 16a

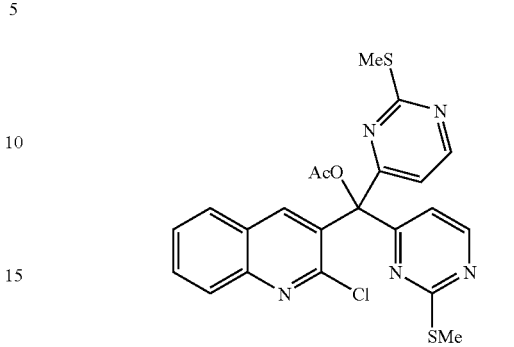

A solution of 4-iodo-2-methylthiopyrimidine 13 (0.50 g, 2.0 mmol) in dry toluene (12 mL) was treated at 0° C. with i-PrMgCl (1.0 mL, 2 M in tetrahydrofuran, 2 mmol) for 1 h. The arylmagnesium formed was transferred via canula to a solution of 15a (0.32 g, 1.0 mmol) in dry toluene (30 mL) at 0° C., stirred for 25 min, treated with excess of acetyl chloride (2.0 mL), and stirred overnight at 23° C. The reaction mixture was partitioned between ethyl acetate and saturated aqueous solution of sodium bicarbonate. The organic layer was dried over sodium sulphate, filtered, and evaporated. The residue was chromatographed (hexane:ethyl acetate, from 4:1 to 1:1) to give 16a as a yellow solid (150 mg, 15%).

$^1$H NMR (CDCl$_3$, 300 MHz) δ 8.53 (d, J=5.1 Hz, 2H), 8.32 (s, 1H), 8.01 (d, J=8.5 Hz, 1H), 7.81-7.77 (m, 2H), 7.58 (t, J=7.6 Hz, 1H), 7.35 (d, J=5.1 Hz, 2H), 2.36 (s, 6H), 2.30 (s, 3H).

EXAMPLE 7

Compound 16b

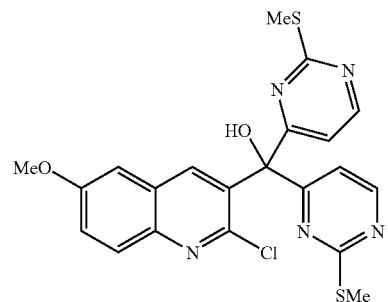

A solution of 4-iodo-2-methylthiopyrimidine 13 (2.1 g, 8.3 mmol, 2.0 equiv) in tetrahydrofuran (50 mL) was treated at −100° C. with n-BuLi (3.3 mL, 2.5 M in hexanes, 8.3 mmol) and stirred at −100° C. for 45 min. Afterwards, a solution of 15b (1.4 g, 4.1 mmol) in tetrahydrofuran (20 mL) at −78° C. was slowly added via canula maintaining −100° C. The reaction mixture was stirred at −100° C. for 3 h. The reaction was quenched with a saturated aqueous solution of ammonium chloride, warmed to 23° C. and partitioned between ethyl acetate and saturated aqueous solution of ammonium chloride. The organic layer was dried over sodium sulphate, filtered, and evaporated. The crude was chromatographed (hexane:ethyl acetate, from 4:1 to 2:1) to give 16b as a white solid (1.48 g, 76%).

$^1$H NMR (CDCl$_3$, 300 MHz) δ 8.57 (d, J=5.1 Hz, 2H), 7.87 (d, J=9.3 Hz, 1H), 7.47 (s, 1H), 7.43 (d, J=5.1 Hz, 2H), 7.36 (dd, J=9.3, 2.7 Hz, 1H), 6.92 (d, J=2.7 Hz, 1H), 6.34 (s, 1H), 3.87 (s, 3H), 2.47 (s, 6H).

$^{13}$C NMR (CDCl$_3$, 75 MHz) δ 172.1, 169.4, 158.7, 158.2, 147.5, 143.1, 138.1, 134.4, 129.7, 127.4, 124.2, 115.3, 105.7, 80.0, 55.9, 14.5.

MS (ESI) m/z: 494 (M+23)$^+$.

Rf: 0.06 (hexane:ethyl acetate, 4:1).

EXAMPLE 8

Compound 17a

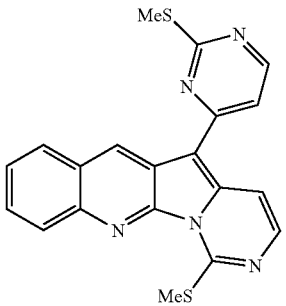

A mixture of 16a (680 g, 1.40 mmol), triethylsilane (2.70 mL, 16.9 mmol) and trifluoroacetic acid (0.23 mL, 2.95 mmol) was refluxed in dichloroethane (3 mL) in a sealed tube at 80° C. for 32 h. After cooling, the red residue was diluted with CH$_2$Cl$_2$ (50 mL) and washed with a saturated aqueous solution of sodium bicarbonate (50 mL) and a saturated aqueous solution of NaCl (50 mL). The combined organic layer was dried over sodium sulphate, filtered, evaporated and chromatographed (CH$_2$Cl$_2$:ethyl acetate, from 100:0 to 30:1) to give 17a as an orange solid (226 mg, 41%).

$^1$H NMR (CDCl$_3$, 300 MHz) δ 8.95 (s, 1H), 8.53 (d, J=5.4 Hz, 1H), 8.26 (d, J=8.2 Hz, 1H), 8.09-8.03 (m, 2H), 7.89 (d, J=6.6 Hz, 1H), 7.75 (t, J=7.2 Hz, 1H), 7.60 (t, J=7.9 Hz, 1H), 7.41 (d, J=5.3 Hz, 1H), 2.76 (s, 3H), 2.71 (s, 3H).

$^{13}$C NMR (CDCl$_3$, 75 MHz) δ 173.5, 161.0, 157.3, 156.3, 144.8, 143.1, 141.8, 141.0, 128.7, 128.4, 128.0, 126.3, 125.9, 120.0, 112.7, 108.4, 100.1, 15.1, 14.4.

MS (ESI) m/z: 392 (M+1)$^+$.

Rf: 0.83 (CH$_2$Cl$_2$:MeOH, 96:4).

EXAMPLE 9

Compound 17b

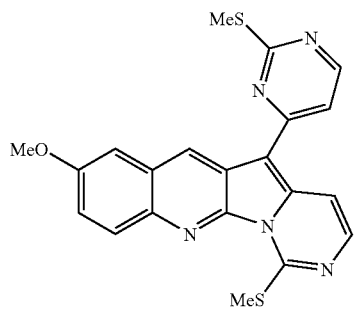

A suspension of 16b (113 mg, 0.24 mmol) and TFA (37 μL, 0.48 mmol) in 1.2-dichloroethane (0.5 mL) was treated with Et$_3$SiH (0.3 mL, 1.9 mmol) in a sealed tube at 100° C. for 43 h. The reaction mixture was cooled, and partitioned between CH$_2$Cl$_2$ and saturated aqueous solution of sodium bicarbonate. The organic layer was dried over sodium sulphate, filtered, and evaporated. The crude was chromatographed (hexane:ethyl acetate, from 4:1 to 2:1) to give 17b as a yellow solid (34 mg, 34%).

$^1$H NMR (CDCl$_3$, 300 MHz) δ 8.87 (s, 1H), 8.54 (d, J=5.4 Hz, 1H), 8.18 (d, J=9.0 Hz, 1H), 8.11 (d, J=6.6 Hz, 1H), 7.83 (d, J=6.6 Hz, 1H), 7.46 (d, J=5.4 Hz, 1H), 7.42 (dd, J=9.0, 2.7 Hz, 1H), 7.27 (d, J=2.7 Hz, 1H), 4.00 (s, 3H), 2.76 (s, 3H), 2.72 (s, 3H).

MS (APCI) m/z: 420 (M+1)$^+$.

Rf: 0.27 (hexane:ethyl acetate, 4:1).

EXAMPLE 10

Compound 18a

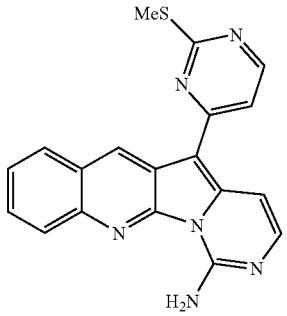

A solution of 17a (15.3 mg, 0.039 mmol) in a mixture of 1.4-dioxane (5 mL) and NH$_4$OH (8 mL, 32%) was heated in a sealed tube at 85° C. for 16 h. The reaction mixture was evaporated and chromatographed (CH$_2$Cl$_2$:MeOH, 98:2) to give 18a as a yellow solid (9.3 mg, 67%).

$^1$H NMR (CDCl$_3$, 300 MHz) δ 9.02 (s, 1H), 8.49 (d, J=5.4 Hz, 1H), 8.11 (d, J=8.5 Hz, 1H), 8.02 (d, J=8.3 Hz, 1H), 7.72-7.68 (m, 2H), 7.59 (t, J=8.1 Hz, 1H), 7.54 (d, J=6.8 Hz, 1H), 7.35 (d, J=5.4 Hz, 1H), 2.71 (s, 3H).

MS (ESI) m/z: 359 (M+1)$^+$.

Rf: 0.64 (CH$_2$Cl$_2$:MeOH, 6:1).

EXAMPLE 11

Compound 18b

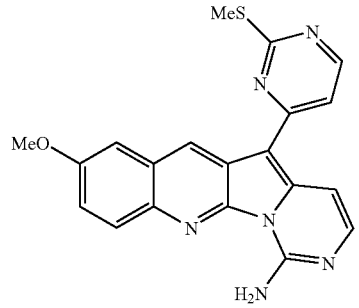

A solution of 17b (21.0 mg, 0.05 mmol) in 1.4-dioxane: NH₄OH 32%, 2:3 (25 mL) was heated at 90° C. in a sealed tube for 16 h. The reaction mixture was evaporated and chromatographed (CH₂Cl₂:MeOH, 98:2) to give 18b as a yellow solid (10 mg, 52%).

¹H NMR (CDCl₃, 300 MHz) δ 8.80 (s, 1H), 8.30 (d, J=5.3 Hz, 1H), 7.91 (d, J=8.7 Hz, 1H), 7.52-7.47 (m, 2H), 7.32 (d, J=5.3 Hz, 1H), 7.27-7.25 (dd, J=8.7, 2.7 Hz, 1H), 7.16 (d, J=3.0 Hz, 1H), 3.85 (s, 3H), 2.58 (s, 3H).

MS (ESI) m/z: 389 (M)⁺.

EXAMPLE 12

Compound 19a

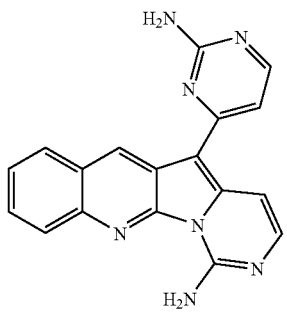

A solution of 17a (26.7 mg, 0.068 mmol) in CH₂Cl₂ (3 mL) at −30° C. was treated dropwise with a solution of mCPBA (12.5 mg, 0.051 mmol, 2.4 equiv, 77%) in CH₂Cl₂ (1 mL) and warmed to 0° C. for 30 min. The reaction mixture was treated with a saturated aqueous solution of Na₂S₂O₃ and washed with a saturated aqueous solution of sodium bicarbonate. The organic layer was dried over sodium sulphate, filtered, and evaporated. The reaction crude was disolved in 1.4-dioxane: NH₄OH (32%) and heated at 80° C. in a sealed tube for 16 h. The reaction mixture was evaporated and chromatographed (CH₂Cl₂:CH₃OH, from 98:2 to 94:6) to give 19a as a yellow solid (4.5 mg, 20%).

¹H NMR (CDCl₃, 300 MHz) δ 8.90 (s, 1H), 8.17 (d, J=5.5 Hz, 1H), 8.07 (d, J=8.6 Hz, 1H), 8.00 (d, J=7.8 Hz, 1H), 7.64 (t, J=7.2 Hz, 1H), 7.52 (t, J=7.4 Hz, 1H), 7.48 (d, J=6.7 Hz, 1H), 7.40 (d, J=6.7 Hz, 1H), 7.04 (d, J=5.5 Hz, 1H).

MS (ESI) m/z: 328 (M+1).

Rf: 0.79 (CH₂Cl₂:MeOH, 6:1).

EXAMPLE 13

Compound 42

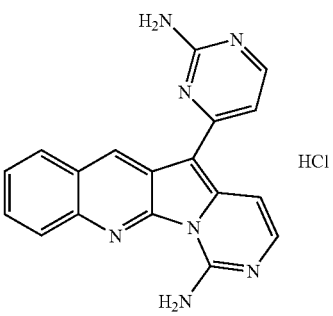

19a (2.1 mg, 0.006 mmol) was treated with HCl in 1.4-dioxane (0.5 mL, 3.8 M) at 23° C. for 5 min. The reaction mixture was evaporated to give 42 as a yellow solid (2.5 mg, 100%).

¹H NMR (CD₃OD, 300 MHz) δ 9.47 (s, 1H), 8.30 (d, J=8.5 Hz, 1H), 8.23 (d, J=6.9 Hz, 1H), 8.20 (d, J=6.6 Hz, 1H), 7.97 (d, J=7.2 Hz, 1H), 7.89 (t, J=6.9 Hz, 1H), 7.79 (d, J=7.5 Hz, 1H), 7.74 (t, J=8.4 Hz, 1H), 7.59 (d, J=6.9 Hz, 1H).

MS (ESI) m/z: 328 (M)⁺.

EXAMPLE 14

Compund 19b

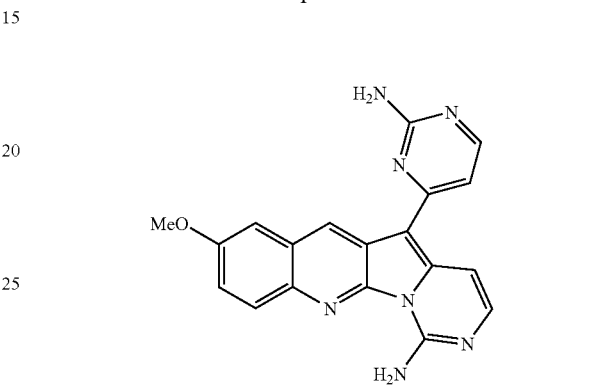

A solution of 17b (18.0 mg, 0.04 mmol) in CH₂Cl₂ (5 mL) was treated at −30° C. with a solution of mCPBA (24.7 mg, 0.11 mmol, 77%) in CH₂Cl₂ (3 mL). The reaction mixture was warmed up to 0° C. for 30 min and treated with a saturated aqueous solution of Na₂S₂O₃. The reaction mixture was partitioned between CH₂Cl₂ and saturated aqueous solution of sodium bicarbonate, dried over sodium sulphate, filtered, and evaporated. The residue was chromatographed (CH₂Cl₂: MeOH, 95:5) to give 19b as a yellow solid (2.8 mg, 20%).

¹H NMR (CDCl₃, 300 MHz) δ 8.81 (s, 1H), 8.13 (d, J=5.6 Hz, 1H), 7.91 (d, J=9.3 Hz, 1H), 7.45 (d, J=6.8 Hz, 1H), 7.37 (d, J=6.8 Hz, 1H), 7.27 (dd, J=9.3, 2.7 Hz, 1H), 7.20 (d, J=2.7 Hz, 1H), 6.99 (d, J=5.6 Hz, 1H), 3.89 (s, 3H).

EXAMPLE 15

Compound 20

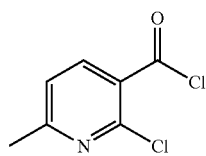

DMF (2 drops) was added to a suspension of oxalyl chloride (5.4 mL, 10.6 mmol) and 2-chloro-6-methylnicotinic acid (1.69 g, 9.8 mmol) in CH₂Cl₂ (45 mL). The mixture was stirred for 3 h at 23° C. and the solvent was evaporated under reduced pressure to give a brown oil (1.8 g, 97%) which was used without further purification.

¹H NMR (CDCl₃, 330 MHz) δ 8.35 (d, J=8.2 Hz, 1H), 7.28 (d, J=8.0 Hz, 1H), 2.61 (s, 3H).

EXAMPLE 16

Compound 21

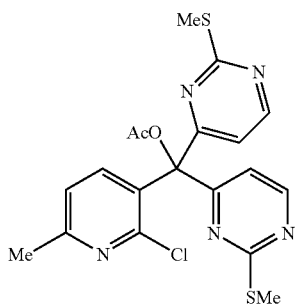

n-BuLi (11.6 mL, 2.5 M in hexane, 28.8 mmol) was added dropwise to a solution of 4-iodo-2-methylthiopyrimidine 13 (7.16 g, 28.4 mmol) in tetrahydrofuran (60 mL) at −100° C. The black solution was stirred for 15 min at −100° C. A solution of 2-chloro-6-methylnicotinoyl chloride 20 (1.8 g, 9.47 mmol) in tetrahydrofuran (10 mL) was added via cannula at −100° C. The intense red mixture was stirred for 1 h at −95° C. and acetyl chloride (3.4 mL, 47.3 mmol) was added carefully. The red mixture was stirred for 4 h at 23° C. and a saturated aqueous solution of sodium bicarbonate (100 mL) was added. The layers were separated and the aqueous layer was extracted with diethyl ether (3×150 mL). The combined organic layers were dried over sodium sulphate, filtered, and concentrated under reduced pressure. The red residue was chromatographed (hexane:ethyl acetate, from 1:5 to 1:1.5) to afford 21 (2.3 g, 54%) as a pale red solid.

$^1$H NMR (300 MHz, CDCl$_3$) δ 8.54 (d, J=5.2 Hz, 2H), 7.79 (d, J=8.0 Hz, 1H), 7.31 (d, J=5.3 Hz, 2H), 7.05 (d, J=7.7 Hz, 1H), 2.56 (s, 3H), 2.49 (s, 6H), 2.27 (s, 3H).

EXAMPLE 17

Compound 22

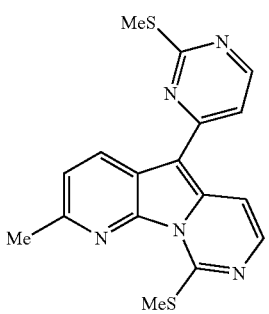

A mixture of 21 (2.3 g, 5.1 mmol), Et$_3$SiH (6.6 mL, 41.1 mmol) and trifluoroacetic acid (0.83 mL, 10.7 mmol) was refluxed in dichloroethane (10 mL) in a sealed tube for 3 h. After cooling, the red residue was filtered, washed with diethyl ether and poured in a mixture of CH$_2$Cl$_2$ (300 mL) and a saturated aqueous solution of sodium bicarbonate (300 mL). The brown mixture was stirred for 1 h at 23° C. and the layers were separated. The aqueous layer was extracted with CH$_2$Cl$_2$ (3×200 mL) and the combined organic layers were dried over sodium sulphate, filtered and concentrated under reduced pressure to afford 22 (1.1 g, 61%) as a yellow solid.

$^1$H NMR (300 MHz, CDCl$_3$) δ 8.51 (d, J=8.4 Hz, 1H), 8.50 (d, J=5.5 Hz, 1H), 8.07 (d, J=6.5 Hz, 1H), 7.78 (d, J=6.5 Hz, 1H), 7.37 (d, J=8.4 Hz, 1H), 7.34 (d, J=5.5 Hz, 1H), 2.79 (s, 3H), 2.79 (s, 3H), 2.71 (s, 3H).

EXAMPLE 18

Compound 24

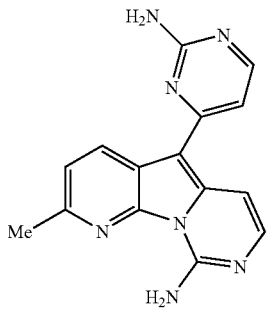

A solution of mCPBA (45 mg, 0.18 mmol, 77%) in CH$_2$Cl$_2$ (2 mL), previously dried over sodium sulphate, was added dropwise to a cooled (−30° C.) solution of 22 (29.5 mg, 0.083 mmol) in CH$_2$Cl$_2$ (4 mL). The yellow solution was stirred for 15 min at 0° C. A saturated aqueous solution of Na$_2$S$_2$O$_3$ (5 mL) was added and washed with a saturated aqueous solution of sodium bicarbonate (5 mL). The combined aqueous layers were extracted with CH$_2$Cl$_2$ (3×10 mL). The combined organic layers were dried over sodium sulphate, filtered, and concentrated. The intermediate 23 was poured in a sealed tube with 1.4-dioxane (4 mL) and ammonia solution 32% (14 mL) was added. The brown mixture was heated for 14 h at 85° C. The resulting brown mixture was evaporated in vacuo and CH$_2$Cl$_2$:MeOH (10:1, 11 mL) was added, dried over sodium sulphate, filtered, and the solvent evaporated at reduced pressure. The yellow solid was purified by flash chromatography using CH$_2$Cl$_2$:MeOH (2%) to CH$_2$Cl$_2$:MeOH (5%) as eluent to afford 24 (4 mg, 17%, 2 steps) as a yellow solid.

$^1$H NMR (CDCl$_3$, 300 MHz) δ 8.50 (d, J=8.3 Hz, 1H), 8.19 (d, J=5.4 Hz, 1H), 7.46-7.73 (m, 2H), 7.29 (d, J=8.3 Hz, 1H), 6.97 (d, J=5.4 Hz, 1H), 2.68 (s, 3H).

MS (ES) m/z: 292 (M+1)$^+$.

EXAMPLE 19

Compound 44

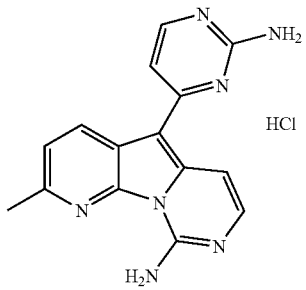

Compound 24 (30 mg) was suspended in a HCl solution in 1.4-dioxane (6 mL, 3.8 N) at 0° C. The pale brown mixture was stirred at 0° C. for 15 min and evaporated in vacuo. CH$_2$Cl$_2$ (5 mL) was added, stirred for 1 min and evaporated again. 1.4-dioxane (5 mL) was added and the pale brown solid was filtered and washed with more 1.4-dioxane (3 mL) to afford 30 mg of 44.

$^1$H NMR (CD$_3$OD, 300 MHz) δ 8.84 (d, J=8.3 Hz, 1H), 8.21 (d, J=6.8 Hz, 1H), 8.00 (d, J=7.3 Hz, 1H), 7.66 (d, J=7.6 Hz, 1H), 7.61 (d, J=8.3 Hz, 1H), 7.30 (d, J=6.8 Hz, 1H), 2.79 (s, 3H).

EXAMPLE 20

Compound 43

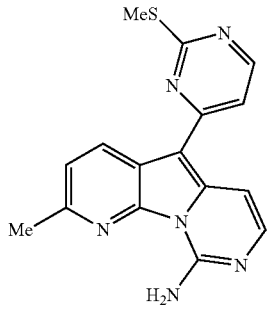

Ammonia solution 32% (4 mL) was added to a solution of 22 (11 mg, 0.031 mmol) in 1.4-dioxane (2 mL). The brown mixture was heated for 14 h at 85° C. in a sealed tube. The resulting yellow mixture was evaporated in vacuo, CH$_2$Cl$_2$ (5 mL) was added, and dried over sodium sulphate, filtered, and the solvent evaporated at reduced pressure. The yellow solid was purified by flash chromatography using (CH$_2$Cl$_2$:MeOH, from 1% to 3%) as eluent to afford 43 (3 mg, 67% BRSM) as a yellow solid.

$^1$H NMR (CDCl$_3$, 300 MHz) δ 8.60 (d, J=8.3 Hz, 1H), 8.47 (d, J=5.4 Hz, 1H), 7.63 (d, J=6.6 Hz, 1H), 7.57 (d, J=6.6 Hz, 1H), 7.35 (d, J=8.5 Hz, 1H), 7.31 (d, J=5.4 Hz, 1H), 2.73 (s, 3H), 2.69 (s, 3H).

MS (ESI) m/z: 323 (M+1)$^+$.

EXAMPLE 21

Compound 45

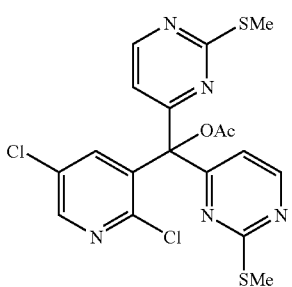

A solution of 4-iodo-2-methylthiopyrimidine 13 (0.76 g, 3.0 mmol) in dry tetrahydrofuran (10 mL) was treated at −100° C. with nBuLi (1.2 mL, 2.5 M in hexanes, 3.0 mmol) and the orange solution was stirred at −100° C. for 20 min. A solution of 2.5-dichloronicotinoyl chloride (0.21 g, 1.0 mmol) in tetrahydrofuran (5 mL) was added dropwise to the previously prepared solution of the organolithium derivative and the reaction mixture was stirred for 3 h at −100° C. After this, the crude reaction was quenched with a saturated aqueous solution of ammonium chloride (20 mL) and extracted with ethyl acetate (3×20 mL). The combined organic layers were dried over sodium sulphate, filtered, and concentrated. Flash chromatography of the residue (ethyl acetate:hexane, 50:50) afforded the corresponding carbinol (0.11 g, 26%).

A solution of this carbinol (0.11 g, 0.26 mmol) in tetrahydrofuran (10 mL) was added to a suspension of NaH (16 mg, 0.4 mmol, 60%) in tetrahydrofuran (5 mL). The dark red mixture was stirred at 23° C. for 10 min. Acetyl chloride (0.071 mL, 1.0 mmol) was then added dropwise and the resulting yellow slurry was stirred for 5 h at 23° C. Saturated aqueous solution of sodium bicarbonate (20 mL) was added and the aqueous layer was extracted with CH$_2$Cl$_2$ (3×20 mL). The combined organic layers were dried over sodium sulphate, filtered, and concentrated to afford 45 (0.11 g, 90%, overall yield 24%) as a brown oil which was used without further purification.

$^1$H NMR (CDCl$_3$, 300 MHz) δ 2.30 (s, 3H), 2.40 (s, 6H), 7.28 (d, J=5.3 Hz, 2H), 7.91 (d, J=2.4 Hz, 1H), 8.34 (d, J=2.4 Hz, 1H), 8.52 (d, J=5.3 Hz, 2H).

MS (ESI) m/z: 468 (M)$^+$.

EXAMPLE 22

Compound 46

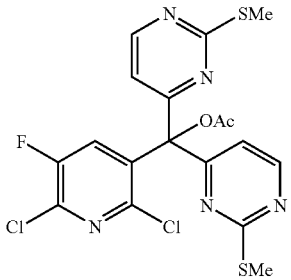

A solution of 4-iodo-2-methylthiopyrimidine 13 (2.3 g, 9.0 mmol) in dry tetrahydrofuran (10 mL) was treated at −100° C. with nBuLi (3.6 mL, 2.5 M in hexanes, 9.1 mmol) and the orange solution was stirred at this temperature for 20 min. A solution of 2.6-dichloro-5-fluoronicotinoyl chloride (0.69 g, 3 mmol) in tetrahydrofuran (5 mL) was added dropwise to the previously prepared solution of the organolithium derivative and the reaction mixture was stirred for 3 h at −100° C. After this, the crude reaction was quenched with a saturated aqueous solution of ammonium chloride (20 mL) and extracted with ethyl acetate (3×20 mL). The combined organic layers were dried over sodium sulphate, filtered, and concentrated. Flash chromatography of the residue (ethyl acetate:hexane, 50:50) to afford the corresponding carbinol (0.15 g, 11%).

A solution of this carbinol (0.15 g, 0.3 mmol) in tetrahydrofuran (3 mL) was added to a suspension of NaH (20 mg, 0.5 mmol, 60%) in tetrahydrofuran (2 mL). The dark red mixture was stirred at 23° C. for 10 min. Acetyl chloride (0.10 mL, 1.3 mmol) was then added dropwise and the resulting yellow slurry was stirred for 5 h at 23° C. Saturated aqueous solution of sodium bicarbonate (20 mL) was added and the aqueous layer was extracted with $CH_2Cl_2$ (3×20 mL). The combined organic layers were dried over sodium sulphate, filtered, and concentrated to afford 46 (0.13 g, 83%, overall yield 9%) as a brown oil which was used without further purification.

$^1$H NMR ($CDCl_3$, 300 MHz) δ 2.31 (s, 3H), 2.42 (s, 6H), 7.27 (d, J=5.3 Hz, 2H), 7.81 (d, $J_{H-F}$=8.6 Hz, 1H), 8.52 (d, J=5.3 Hz, 2H).

MS (ESI) m/z 486 (M)$^+$.

EXAMPLE 23

Compound 47

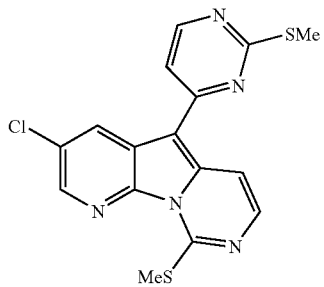

A solution of 45 (110 mg, 0.23 mmol) and trifluoroacetic acid (0.04 mL, 0.52 mmol) in 1.2-dichloroethane (2 mL) was transferred to a Young tube fitted with a rubber septum, containing triethylsilane (0.33 mL, 2.08 mmol). Under a strong flow of Argon, the septum was replaced with a Teflon screw cap, and sealed reaction vessel was heated at 100° C. for 48 h. After cooling, the vessel was opened and the contents diluted with $CH_2Cl_2$ (10 mL). The solution was neutralized with a saturated aqueous solution of sodium bicarbonate (10 mL) and the layers separated. The aqueous layer was repeatedly extracted with $CH_2Cl_2$ and the combined organic layers were dried over sodium sulphate, filtered, and concentrated. Purification of the crude material was achieved by flash chromatography (ethyl acetate:Hexane, 33%) to afford a mixture of two products with the same Rf. 47 was obtained by addition of diethyl ether (15 mL) and filtration as a yellow solid (20 mg, 20%).

$^1$H NMR ($CDCl_3$, 300 MHz) δ 2.68 (s, 3H), 2.73 (s, 3H), 7.31 (d, J=5.4 Hz, 1H), 7.86 (d, J=6.5 Hz, 1H), 8.00 (d, J=6.5 Hz, 1H), 8.51 (d, J=2.1 Hz, 1H), 8.54 (d, J=5.4 Hz, 1H), 8.66 (d, J=2.1 Hz, 1H).

MS (ESI) m/z: 374 (M+1)$^+$.

EXAMPLE 24

Compound 48

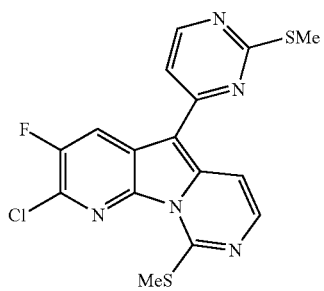

A solution of 46 (200 mg, 0.42 mmol) and trifluoroacetic acid (64 μL, 0.82 mmol) in 1.2-dichloroethane (2 mL) was transferred to a Young tube fitted with with a rubber septum, containing triethylsilane (0.52 mL, 3.28 mmol). Under a strong flow of Argon, the septum was replaced with a Teflon screw cap, and sealed reaction vessel was heated at 140° C. for 96 h. After cooling, the vessel was opened and the contents diluted with $CH_2Cl_2$ (10 mL). The solution was neutralized with a saturated aqueous solution of sodium bicarbonate (10 mL) and the layers separated. The aqueous layer was repeatedly extracted with $CH_2Cl_2$ and the combined organic layers were dried over sodium sulphate, filtered, and concentrated. Purification of the crude material was achieved by flash chromatography (ethyl acetate:Hexane, 33%) to afford a mixture of two product with the same Rf. 48 was obtained by addition of diethyl ether (15 mL) and filtration as a yellow solid (26 mg, 16%).

$^1$H NMR ($CDCl_3$, 300 MHz) δ 2.67 (s, 3H), 2.74 (s, 3H), 7.25 (d, J=5.4 Hz, 1H), 7.85 (d, J=6.5 Hz, 1H), 7.91 (d, J=6.5 Hz, 1H), 8.47 (d, $J_{H-F}$=8.8 Hz, 1H), 8.53 (d, J=5.4 Hz, 1H).

MS (ESI) m/z: 392 (M+1)$^+$.

EXAMPLE 25

Compound 49

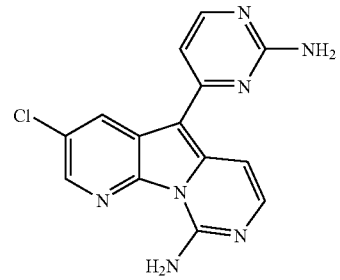

Compound 47 (20 mg, 0.054 mmol) was dissolved in chloroform (5 mL) cooled at −30° C. A precooled solution (−30° C.) of m-chloroperbenzoic acid (19 mg, 0.11 mmol, 77%) in $CH_2Cl_2$ (5 mL) was added dropwise and stirred at 0° C. for 15 min. The solution was warmed up to 23° C., neutralized with a saturated aqueous solution of sodium bicarbonate and repeatedly extracted with $CH_2Cl_2$. The combined organic layers were dried over sodium sulphate, filtered, and concentrated to obtain after the sulphoxide as a yellow solid, which was used without further purification. The crude oxidized material was heated with an excess of p-methoxybenzylamine (1 mL) at 85° C. for 15 h. The reaction mixture was purified by flash chromatography (ethyl acetate:Hexane, 50:50). This product was treated with triflic acid (0.5 mL) at 23° C. for 3 h. The reaction mixture was cooled to 0° C. and treated successively with MeOH (1 mL) and aqueous $NH_4OH$ (1 mL, 32%).

The precipitate was filtered off, washed with MeOH (5 mL) and diethyl ether (5 mL) and dried to afford 49 as a yellow solid (10 mg, overall yield 60%).

$^1$H-NMR ($CDCl_3$, 300 MHz) δ 6.92 (d, J=5.5 Hz, 1H), 7.34 (d, J=6.6 Hz, 1H), 7.51 (d, J=6.6 Hz, 1H), 8.17 (d, J=5.5 Hz, 1H), 8.25 (d, J=2.2 Hz, 1H), 8.64 (d, J=2.2 Hz, 1H).

MS (ESI) m/z: 312 (M+1)$^+$.

EXAMPLE 26

Compund 50

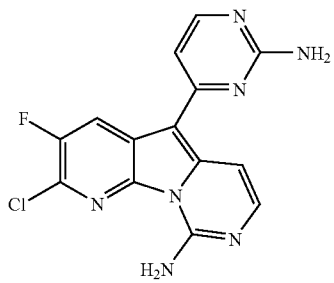

Compound 48 (26 mg, 0.066 mmol) was dissolved in chloroform (5 mL) and cooled at −30° C. A precooled solution (−30° C.) of m-chloroperbenzoic acid (23 mg, 0.132 mmol) in CH$_2$Cl$_2$ (5 mL) was added dropwise, and stirred at 0° C. for 15 min. The solution was warmed up to 23° C., neutralized with a saturated aqueous solution of sodium bicarbonate and repeatedly extracted with CH$_2$Cl$_2$. The combined organic layers were dried over sodium sulphate, filtered, and concentrated to afford the sulphoxide as a yellow solid, which was used without further purification. The crude oxidized material was heated with an excess of p-methoxybenzylamine (1 mL) at 85° C. for 15 h. The reaction mixture was purified by flash chromatography (ethyl acetate:Hexane, 50:50). This product was treated with triflic acid (0.5 mL) at 23° C. for 3 h. The reaction mixture was cooled to 0° C. and treated successively with MeOH (1 mL) and aqueous NH$_4$OH (1 mL, 32%).

The precipitate was filtered, washed with MeOH (5 mL) and diethyl ether (5 mL) and dried to afford 50 as a yellow solid (3 mg, overall yield 14%).

$^1$H NMR (CDCl$_3$, 300 MHz) δ 6.86 (d, J=5.4 Hz, 1H), 7.28 (d, J=6.6 Hz, 1H), 7.48 (d, J=6.6 Hz, 1H), 8.12 (d, J=5.4 Hz, 1H), 8.50 (d, J$_{H-F}$=9.3 Hz, 1H).

MS (ESI) m/z: 329 (M)$^+$.

EXAMPLE 27

Compound 8b

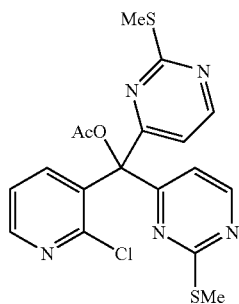

Method A

A solution of i-propylmagnesium bromide (5.0 mL, 10.0 mmol, 2.0 M in tetrahydrofuran) was added dropwise to a solution of 4-iodo-2-methylthiopyrimidine 13 (2.52 g, 10.0 mmol) in toluene (60 mL) at 0° C. The brown solution was stirred for 1 h at 0° C. This solution was added dropwise to a solution 31 (1.06 g, 4 mmol) in toluene (40 mL) via canula over a 20 min period. When the addition was complete, the reaction mixture was stirred for 15 additional minutes at 0° C. and then quenched with acetyl chloride (0.99 mL, 14.0 mmol). The ice bath was removed and the resulting brown slurry was stirred for 3 h at 23° C. Saturated aqueous solution of sodium bicarbonate (100 mL) was added and the aqueous layer was extracted with ethyl acetate (3×50 mL). The combined organic layers were dried over sodium sulphate, filtered, and concentrated. Flash chromatography of the crude residue (ethyl acetate:Hexane:, 50:50) afforded 8b (1.28 g, 74%) as a pale orange foamy solid. The product was isolated together with a small amount of 32 that is formed as a side product in the reaction. The mixture of both compounds was used in the next step.

8b:

$^1$H NMR (CDCl$_3$, 300 MHz) δ 8.48 (d, J=5.1 Hz, 2H), 8.36 (dd, J=4.9, 1.9 Hz, 1H), 7.86 (dd, J=7.8, 1.7 Hz, 1H), 7.28 (d, J=5.1 Hz, 2H), 7.24 (dd, J=7.8, 4.6 Hz, 1H), 2.36 (s, 6H), 2.28 (s, 3H).

MS (ESI) m/z: 456 (M+23)$^+$, 434 (M+1)$^+$.

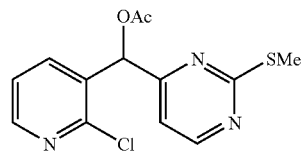

32

$^1$H NMR (CDCl$_3$, 300 MHz) δ 8.47 (d, J=5.1 Hz, 1H), 8.37 (dd, J=4.9, 1.9 Hz, 1H), 7.82 (dd, J=7.8, 1.6 Hz, 1H), 7.30 (dd, J=7.8, 4.6 Hz, 1H), 7.10 (d, J=5.1 Hz, 1H), 7.01 (s, 1H), 2.36 (s, 3H), 2.28 (s, 3H).

Method B n-BuLi (9 mL, 22.6 mmol, 2.5 M in hexane) previously cooled at −78° C., was added dropwise to a solution of 31 (3 g, 11.3 mmol) and 4-iodo-2-methylthiopyrimidine 13 (5.71 g, 22.6 mmol) in tetrahydrofuran (75 mL) at −78° C. The dark brown mixture was stirred for 15 min at −78° C. and acetyl chloride (3.2 mL, 45.3 mmol) was added carefully. The dark green slurry was stirred at 23° C. for 3.5 h, quenched with a saturated aqueous solution of sodium bicarbonate (150 mL), and extracted with diethyl ether (2×150 mL). The combined organic layers were dried over MgSO$_4$, filtered, and concentrated. The red residue was purified by flash chromatography (ethyl acetate:hexane, from 1:4 to 100:0) to afford 8b (3 g, 61%) as a pale red solid.

EXAMPLE 28

Compound 9

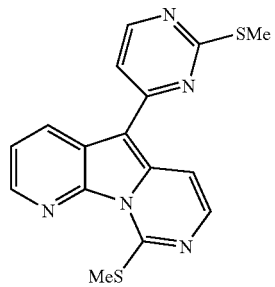

A mixture of 8b (1.6 g, 3.7 mmol), trifluoroacetic acid (0.6 mL, 7.74 mmol) and Et₃SiH (4.7 mL, 29.5 mmol) were poured in a Young tube containing 1.2-dichloroethane (8 mL). The sealed reaction vessel was heated at 90° C. for 24 h. After cooling, the vessel was opened and the contents diluted with chloroform (100 mL). The solution was neutralised with a saturated aqueous solution of sodium bicarbonate (100 mL) and the layers separated. The aqueous layer was repeatedly extracted with chloroform and the combined organic layers were dried over sodium sulphate, filtered, and concentrated. The dark red residue was purified by addition of diethyl ether (100 mL) and filtration of the bright red precipitate to obtain 9 (0.85 g, 68%).

¹H NMR (CDCl₃, 300 MHz) δ 8.64 (dd, J=8.1, 1.7 Hz, 1H), 8.60 (dd, J=4.6, 1.7 Hz, 1H), 8.51 (d, J=5.4 Hz, 1H), 8.06 (d, J=6.4 Hz, 1H), 7.82 (d, J=6.6 Hz, 1H), 7.51 (dd, J=8.5, 4.6 Hz, 1H), 7.34 (d, J=5.4 Hz, 1H), 2.73 (s, 3H), 2.68 (s, 3H).

EXAMPLE 29

Deoxyvariolin 4

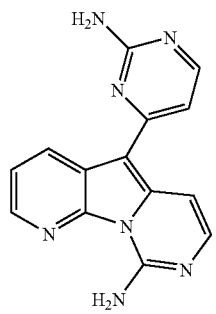

A solution of mCPBA (98 mg, 0.39 mmol, 77%) in CH₂Cl₂ (4 mL), previously dried over sodium sulphate, was added dropwise to a cooled (−30° C.) solution of 9 (61 mg, 0.18 mmol) in CH₂Cl₂ (5 mL). The yellow solution was stirred for 15 min at 0° C. A saturated aqueous solution of Na₂S₂O₃ (5 mL) was added and the organic layer was washed with a saturated aqueous solution of sodium bicarbonate (5 mL). The combined aqueous layers were extracted with CH₂Cl₂ (3×10 mL). The combined organic layers were dried over sodium sulphate, filtered, and concentrated. 28 was poured in a sealed tube with 1.4-dioxane (4 mL) and ammonia solution 32% (8 mL) was added. The brown mixture was heated for 14 h at 85° C. The resulting yellow mixture was evaporated in vacuo and CH₂Cl₂:MeOH (10:1, 11 mL) was added, dried over sodium sulphate, filtered, and the solvent evaporated at reduced pressure. The yellow solid was purified by flash chromatography from CH₂Cl₂:MeOH (2%) to CH₂Cl₂:MeOH (5%) as eluent to afford deoxyvariolin 4 (14 mg, 29%, 2 steps) as a yellow solid.

¹H NMR (DMSO-d₆, 300 MHz) δ 8.92 (dd, J=8.1, 1.5 Hz, 1H), 8.45 (dd, J=4.6, 1.4 Hz, 1H), 8.22 (d, J=5.5 Hz, 1H), 7.68 (d, J=6.6 Hz, 1H), 7.63 (d, J=6.6 Hz, 1H), 7.58 (dd, J=8.1, 4.6 Hz, 1H), 7.06 (d, J=5.4 Hz, 1H).

MS (ESI) m/z: 278 (M+1)⁺.

EXAMPLE 30

Compound 51

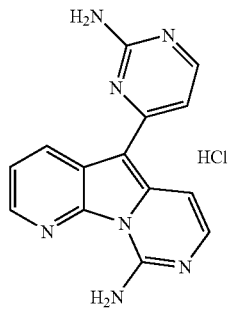

Deoxyvariolin 4 (6 mg, 0.024 mmol) was treated with HCl solution in 1.4-dioxane (2 mL, 5.3 M) and stirred for 2 h at 23° C. The suspension was filtered to afford 51 (3 mg) as a yellow solid.

¹H NMR (CD₃OD, 300 MHz) δ 8.99 (dd, J=8.2, 1.2 Hz, 1H), 8.67 (dd, J=4.9, 1.2 Hz, 1H), 8.30 (d, J=6.8 Hz, 1H), 8.05 (d, J=7.5 Hz, 1H), 7.77 (dd, J=8.3, 4.9 Hz, 1H), 7.67 (1H, J=6.9 Hz, 1H), 7.57 (d, J=7.1 Hz, 1H).

EXAMPLE 31

Compound 30

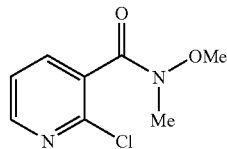

To a vigorously stirred suspension of N,O-dimethylhydroxylamine hydrochloride (33.2 g, 0.34 mol) in tetrahydrofuran (1.2 L), triethylamine (59 mL, 0.426 mol) was added and the reaction mixture was stirred for 20 min at 23° C. After this, 2-chloronicotinoyl chloride 7b (50 g, 0.284 mol) was added neat and the reaction stirred overnight at 23° C. The crude mixture was quenched with a saturated aqueous solution of sodium bicarbonate and extracted with CH₂Cl₂ (3×750 mL). The combined organic layers were dried over sodium sulphate, filtered, and concentrated to afford 30 (49.4 g, 87%) as a yellow solid, which was used without further purification.

¹H NMR (CDCl₃, 300 MHz) δ 3.39 (s, 3H), 3.48 (s, 3H), 7.29 (dd, J=7.5, 4.6 Hz, 1H), 7.68 (d, J=7.5 Hz, 1H), 8.43 (dd, J=4.6, 1.5 Hz, 1H).

MS (ESI) m/z: 201 (M+1)⁺.

EXAMPLE 32

Compound 31

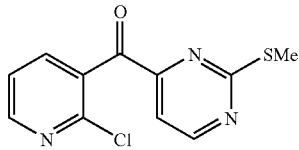

To a solution of 4-iodo-2-methylthiopyrimidine 13 (20.3 g, 80.5 mmol) in dry toluene was added dropwise at −4° C. i-PrMgCl (40.2 mL, 80.5 mmol, 2.0 M in tetrahydrofuran). The pale brown suspension formed was stirred at −4° C. for 45 min. A solution of 30 (12.9 g, 64.4 mmol) in tetrahydrofuran (50 mL) was added via canula for 15 min and the resulting dark brown mixture was stirred at 0° C. for 1 h. The reaction mixture was stopped by addition of a saturated solution of ammonium chloride (200 mL) and extracted with ethyl acetate (2×200 mL). The combined organic layers was dried over sodium sulphate, filtered, and evaporated to give a brown solid (18 g). The residue was triturated with a mixture of diethyl ether and hexane (3:1, 40 mL) and filtered to give 31 as a pale brown solid (13.6 g, 80%).

$^1$H NMR (CDCl$_3$, 300 MHz) δ 8.82 (d, J=4.9 Hz, 1H), 8.57 (dd, J=4.2, 1.9 Hz, 1H), 7.89 (dd, J=7.5, 1.8 Hz, 1H), 7.64 (d, J=5.1 Hz, 1H).7.41 (dd, J=7.6, 4.8 Hz, 1H), 2.38 (s, 3H).

$^{13}$C NMR (CDCl$_3$, 300 MHz) δ 198.2, 173.6, 159.6, 158.7, 151.6, 148.5, 139.4, 133.3, 122.3, 113.6, 14.2.

MS (ESI) m/z: 288 (M+23)$^+$, 266 (M+1)$^+$.

EXAMPLE 33

Compound 33

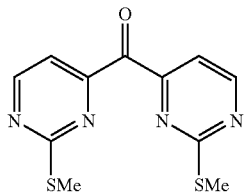

Method A

A solution of 4-iodo-2-methylthiopyrimidine 13 (15.6 g, 62 mmol) in tetrahydrofuran (200 mL) was treated with n-BuLi (24.8 mL, 2.5 M in hexanes, 62 mmol) at −100° C. After the addition the reaction mixture was stirred at −100° C. for 30 min and treated at −110° C. with a solution of diethyl carbonate (3.8 mL, 31 mmol) in tetrahydrofuran (6 mL) for 30 min. The reaction mixture was warmed up to −80° C., quenched with a saturated aqueous solution of ammonium chloride and partitioned between ethyl acetate and saturated aqueous solution of ammonium chloride. The organic layer was dried over sodium sulphate, filtered, and evaporated. The residue was chromatographed (hexane:ethyl acetate, from 4:1 to 3:1) to give 33 as a yellow solid. (5.3 g, 61%).

$^1$H NMR (CDCl$_3$, 300 MHz) δ 8.78 (d, J=4.9 Hz, 2H), 7.53 (d, J=4.9 Hz, 2H), 2.50 (s, 6H).

$^{13}$C NMR (CDCl$_3$, 75 MHz) δ 190.9, 173.5, 159.5, 159.0, 115.2, 14.4.

MS (ESI) m/z: 279 (M+1)$^+$.

Method B

A solution of 4-iodo-2-methylthiopyrimidine 13 (50.4 g, 200 mmol) in toluene (420 mL) was treated with i-PrMgCl (100 mL, 2 M in tetrahydrofuran, 200 mmol) at −10° C. for 2 h. The pyrimidine magnesium was transferred via canula to EtOCOOEt (72 mL, 594.4 mmol) at −10° C. and stirred at 0° C. for 2.5 h. The reaction mixture was quenched with a saturated aqueous solution of ammonium chloride, warmed to 23° C. and partitioned between ethyl acetate and saturated aqueous solution of ammonium chloride. The organic layer was dried over sodium sulphate, filtered, and evaporated. The residue was triturated with CH$_2$Cl$_2$, and filtered. The filtrate was evaporated and chromatographed (hexane:ethyl acetate, from 4:1 to 3:1) to give 33 as a yellow solid (13.3 g, 48%).

EXAMPLE 34

Compound 34

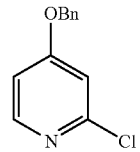

A suspension of 4-benzyloxy-2-(1)pyridone (3.0 g, 5.0 mmol) in freshly distilled POCl$_3$ (18 mL) was heated at 90° C. for 15 h. The reaction mixture was cooled and evaporated. The residue was poured on ice, treated with a saturated aqueous solution of sodium bicarbonate and extracted with CH$_2$Cl$_2$. The organic phase was dried over sodium sulphate, filtered and concentrated. The residue obtained was chromatographed (CH$_2$Cl$_2$:MeOH, 100:1) to give 34 as a white solid (2.5 g, 75%).

$^1$H NMR (CDCl$_3$, 300 MHz) δ 8.19 (d, J=5.7 Hz, 1H), 7.40 (m, 5H), 6.90 (d, J=2.1 Hz, 1H), 6.80 (dd, J=5.7, 2.1 Hz, 1H), 5.10 (s, 2H).

$^{13}$C NMR (CDCl$_3$, 75 MHz) δ 166.6, 152.8, 150.6, 135.3, 129.0, 128.8, 127.8, 110.6, 110.5, 70.6.

MS (ESI) m/z: 219 (M)$^+$.

Rf: 0.4 (hexane:ethyl acetate, 4:1).

EXAMPLE 35

Compound 35

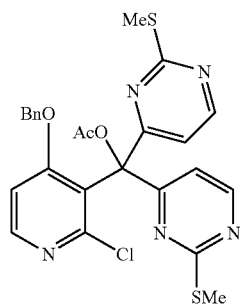

A solution of 34 (1.5 g, 6.8 mmol) in tetrahydrofuran (20 mL) was treated at −100° C. with n-BuLi (2.7 mL, 6.8 mmol, 2.5 M in hexanes), allowed to warm to −78° C. and maintained at this temperature for 4 h. The reaction mixture was cooled to −100° C. and treated via canula with a solution of 33 (1.9 g, 6.8 mmol) in tetrahydrofuran (15 mL) previously cooled at −78° C. The reaction mixture was stirred at −78° C. for 3 h and warmed to −50° C. for 30 min, recooled to −78° C. and treated with acetyl chloride previously distilled under quinoline (2.0 mL, 28 mmol), warmed to 23° C., and stirred overnight. The reaction mixture was partitioned between ethyl acetate and saturated aqueous solution of sodium bicarbonate. The organic layer was dried over sodium sulphate, filtered, and evaporated. The residue was chromatographed (hexane:ethyl acetate, from 2:1 to 1:1) to give 35 as a white solid (2.9 g, 78%).

$^1$H NMR (CDCl$_3$, 300 MHz) δ 8.26 (d, J=5.6 Hz, 1H), 8.11 (d, J=5.4 Hz, 2H), 7.32-7.26 (m, 4H), 7.08 (d, J=5.4 Hz, 2H), 7.02 (dd, J=6.0, 2.4 Hz, 1H), 6.87 (d, J=5.6 Hz, 1H), 4.80 (s, 2H), 2.37 (s, 6H), 2.32 (s, 3H).

$^{13}$C NMR (CDCl$_3$, 75 MHz) δ 171.5, 168.3, 168.1, 165.8, 156.5, 152.5, 149.9, 133.9, 128.7, 128.7, 128.0, 122.5, 115.1, 107.8, 84.7, 71.7, 21.7, 14.2.

EXAMPLE 36

Compound 52

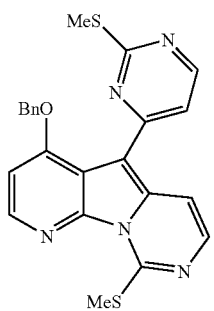

A solution of 35 (740 mg, 1.37 mmol) and TFA (221 μL, 2.86 mmol) in 1.2-dichloroethane (3.0 mL) was added under Ar to a Young tube with Et$_3$SiH (1.8 mL, 11 mmol). The Young tube was closed and heated at 80° C. for 24 h. The reaction mixture was dissolved in chloroform and washed with a saturated aqueous solution of sodium bicarbonate. The organic layer was dried over sodium sulphate, filtered, and evaporated. The residue was chromatographed (hexane:ethyl acetate 4:1) to give 52 as a yellow solid (420 mg, 69%).

$^1$H NMR (CDCl$_3$, 300 MHz) δ 8.47 (d, J=5.4 Hz, 1H), 8.06 (d, J=5.4 Hz, 1H), 8.00 (d, J=6.6 Hz, 1H), 7.71 (d, J=6.6 Hz, 1H), 7.39 (m, 5H), 7.35 (d, J=5.4 Hz, 1H), 7.01 (d, J=5.4 Hz, 1H), 5.28 (s, 2H), 2.70 (s, 3H), 2.63 (s, 3H).

$^{13}$C NMR (CDCl$_3$, 75 MHz) δ 171.2, 160.9, 158.9, 155.8, 154.4, 144.7, 143.6, 138.9, 136.3, 135.1, 128.9, 128.9, 128.3, 118.3, 111.2, 108.9, 103.1, 71.2, 15.12, 14.3. One aromatic carbon overlaps.

MS (APCI) m/z: 446 (M+1)$^+$.

Rf: 0.37 (hexane:ethyl acetate, 2:1).

EXAMPLE 37

Compound 53

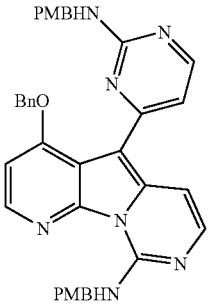

A solution of 52 (1.9 g, 4.3 mmol) in chloroform (50 mL) was treated at −30° C. with a solution of mCPBA (2.4 g, 10.9 mmol, 77%) in chloroform (20 mL). After the addition the reaction mixture was warmed up 0° C., stirred for 20 min and quenched with a saturated aqueous solution of Na$_2$S$_2$O$_3$. The organic layer was washed with a saturated aqueous solution of sodium bicarbonate, dried over sodium sulphate, filtered, and concentrated. The residue was treated with p methoxybenzylamine (10 mL, 76.5 mmol) at 90° C. for 24 h. Excess of p-methoxybenzylamine was removed by distillation in a Kugelrohr apparatus (140° C., 0.5 mm Hg) and the residue was chromatographed (hexane:ethyl acetate, from 1:1 to 0:100) to give 53 as a yellow solid (1.5 g, 55%).

$^1$H NMR (CDCl$_3$, 300 MHz) δ 10.39 (t, J=5.0 Hz, 1H), 8.13 (d, J=5.7 Hz, 1H), 7.95 (d, J=5.2 Hz, 1H), 7.44-7.25 (m, 11H), 6.98 (d, J=5.4 Hz, 1H), 6.91-6.89 (m, 5H), 5.47 (t, J=5.0 Hz, 1H), 5.25 (s, 2H), 4.85 (d, J=5.4 Hz, 2H), 4.62 (d, J=5.7 Hz, 2H), 3.80 (s, 3H), 3.79 (s, 3H).

MS (ESI) m/z: 624 (M)$^+$.

EXAMPLE 38

Variolin B 1

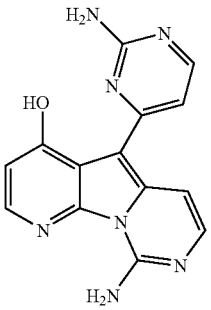

A solution of 53 (204 mg, 0.33 mmol) in TfOH (0.5 mL) was stirred at 23° C. for 4 h. The reaction mixture was cooled to 0° C. and treated dropwise with MeOH (3 mL) and a solution NH$_4$OH (4 mL, 32%). The reaction mixture was filtered and washed with H$_2$O, MeOH and diethyl ether. The solid obtained was chromatographed (CH$_2$Cl$_2$:MeOH, from 95:5 to 85:15) to give variolin B1 as a yellow solid (70 mg, 72%).

¹H NMR (CDCl₃, 300 MHz) δ 8.12 (d, J=5.9 Hz, 1H), 8.07 (d, J=5.4 Hz, 1H), 7.48 (d, J=6.8 Hz, 1H), 7.03-6.99 (m, 2H), 6.76 (d, J=5.4 Hz, 1H).

EXAMPLE 39

Compound 54

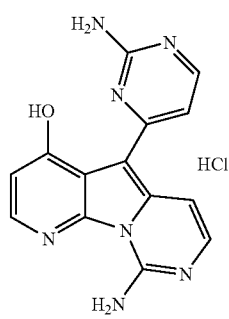

Variolin B (19 mg, 0.065 mmol) was treated with anhydrous HCl in 1.4-dioxane (3.0 mL, 3.8 M) for 5 h at 23° C. The reaction mixture was evaporated and washed with diethyl ether to give 54 as an orange solid.

¹H NMR (CD₃OD, 300 MHz) δ 8.37 (d, J=5.6 Hz, 1H), 8.26 (d, J=6.8 Hz, 1H), 7.78 (d, J=7.6 Hz, 1H), 7.68 (d, J=7.6 Hz, 1H), 7.57 (d, J=6.8 Hz, 1H), 7.07 (d, J=5.6 Hz, 1H).

MS (ESI) m/z: 294 (M+1)⁺.

EXAMPLE 40

Compound 36

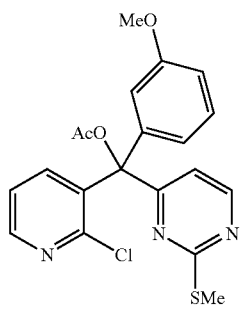

A solution of 3-methoxyphenylmagnesiumbromide (3.2 mL, 3.2 mmol, 1 M in tetrahydrofuran) was added dropwise to a solution of 31 (0.7 g, 2.65 mmol) in tetrahydrofuran (10 mL) at 0° C. The brown mixture was stirred at 0° C. for 2 h. Acetyl chloride (0.75 mL, 10.6 mmol) was added and the mixture was stirred 2 h at 23° C. Saturated aqueous solution of ammonium chloride (50 mL) was added and the aqueous layer was extracted with diethyl ether (3×40 mL). The combined organic layers were dried over MgSO₄, filtered, and evaporated. The orange residue was purified by flash chromatography (ethyl acetate:hexane, from 1:3 to 1:1.5) to afford 36 (0.6 g, 59%) as a colorless oil.

¹H NMR (300 MHz, CDCl₃) δ 8.48 (d, J=5.2 Hz, 1H), 8.37 (dd, J=4.6, 1.7 Hz, 1H), 7.99 (dd, J=7.8, 1.6 Hz, 1H), 7.28-7.20 (m, 3H), 6.95-6.91 (m, 2H), 6.85-6.81 (m, 1H), 3.77 (s, 3H), 2.33 (s, 3H), 2.31 (s, 3H).

EXAMPLE 41

Compound 57

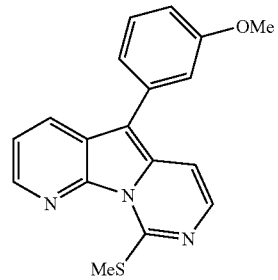

A mixture of 36 (0.38 g, 0.91 mmol), trifluoroacetic acid (0.15 mL, 1.9 mmol) and triethylsilane (1.17 mL, 7.3 mmol) were poured in a Young tube containing 1.2-dichloroethane (4 mL). The sealed reaction vessel was heated at 90° C. for 22 h. After cooling, the vessel was opened and the contents diluted with chloroform (50 mL). The solution was neutralised with a saturated aqueous solution of sodium bicarbonate (60 mL) and the layers separated. The aqueous layer was repeatedly extracted with chloroform and the combined organic layers were dried over sodium sulphate, filtered, and concentrated. The dark red residue was purified by flash chromatography (ethyl acetate:hexane, from 1:4 to 1:3) to afford 57 (20 mg, 54%) as a yellow solid.

¹H NMR (300 MHz, CDCl₃) δ 8.59 (dd, J=4.6, 1.7 Hz, 1H), 8.29 (dd, J=8.2, 1.5 Hz, 1H), 7.57 (d, J=6.6 Hz, 1H), 7.48-7.41 (m, 2H), 7.33 (d, J=6.6 Hz, 1H), 7.24-7.16 (m, 2H), 6.94-6.90 (m, 1H), 3.90 (s, 3H), 2.74 (s, 3H).

¹³C NMR (75 MHz, CDCl₃) δ 160.4, 141.7, 136.8, 134.9, 132.8, 130.3, 127.0, 126.5, 121.6, 120.2, 114.9, 112.1, 107.2, 55.6, 14.8.

MS (ESI) m/z: 344 (M+23)⁺, 322 (M+1)⁺.

EXAMPLE 42

Compound 62

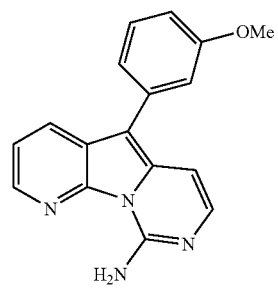

Aqueous NH₄OH (15 mL, 32%) was added to a solution of 57 (150 mg, 0.46 mmol) in 1.4-dioxane (10 mL). The yellow mixture was stirred for 30 h at 90° C. in a sealed tube. The resulting yellow mixture was evaporated at reduced pressure and the yellow residue was purified by flash chromatography using CH$_2$Cl$_2$:MeOH (2%) to CH$_2$Cl$_2$:MeOH (3%) as eluent to afford 62 (64 mg, 65% BRSM) as a yellow solid.

$^1$H NMR (300 MHz, CDCl$_3$) δ 8.38 (dd, J=4.6, 1.5 Hz, 1H), 8.27 (dd, J=8.1, 1.5 Hz, 1H), 7.47-7.38 (m, 3H), 7.27-7.19 (m, 2H), 7.00 (d, J=6.8 Hz, 1H), 6.90 (dd, J=8.3, 2.5 Hz, 1H), 3.90 (s, 3H).

$^{13}$C NMR (75 MHz, CDCl$_3$) δ 160.1, 149.3, 142.6, 139.7, 139.6, 135.1, 133.6, 130.0, 126.5, 122.3, 121.1, 119.7, 114.3, 111.5, 103.8, 100.8, 55.3.

MS (ESI) m/z: 291 (M+1)$^+$.

EXAMPLE 43

Compound 67

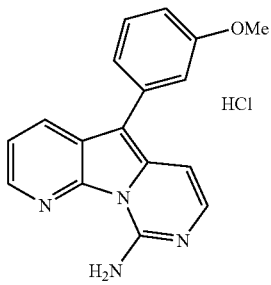

Compound 62 (10 mg, 0.03 mmol) was treated with HCl solution in 1.4-dioxane (3 ml, 3.5 M) and stirred for 2 h at 23° C. The colorless solution was evaporated, washed with diethyl ether and filtered to afford 67 (11 mg) as a yellow solid.

$^1$H NMR (300 MHz, CD$_3$OD) δ 8.65 (dd, J=4.9, 1.5 Hz, 1H), 8.41 (dd, J=8.1, 1.3 Hz, 1H), 7.69 (dd, J=8.1, 4.6 Hz, 1H), 7.52 (t, J=7.8 Hz, 1H), 7.24-7.18 (m, 3H), 7.09 (d, J=8.1 Hz, 1H), 7.06 (dd, J=8.3, 2.4 Hz, 1H), 3.90 (s, 3H).

EXAMPLE 44

Compound 37

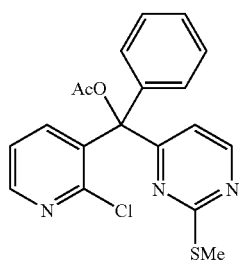

A solution of PhLi (0.58 mL, 1.04 mmol, 1.8 M in cyclohexane:ether) was added dropwise to a solution of 31 (190 mg, 0.73 mmol) in tetrahydrofuran (6 mL) at −78° C. The dark red mixture was stirred at −78° C. for 3 h. Saturated aqueous solution of ammonium chloride (25 mL) was added and the aqueous layer was extracted with diethyl ether (3×40 mL). The combined organic layers were dried over MgSO$_4$, filtered, and evaporated. The orange residue was purified by flash chromatography (ethyl acetate:Hexane from 25% to 35%) to afford the alcohol (0.11 g, 44%) as a pale yellow oil. A solution of alcohol (94 mg, 0.27 mmol) in tetrahydrofuran (2 mL) was added to a suspension of NaH 60% (22 mg, 0.54 mmol) in tetrahydrofuran (1 mL). The dark red mixture was stirred at 23° C. for 10 min. Acetyl chloride (0.6 mL, 8.5 mmol) was added dropwise and the resulting yellow slurry was stirred for 5 h at 23° C. Saturated aqueous solution of sodium bicarbonate (20 mL) was added and the aqueous layer was extracted with CH$_2$Cl$_2$ (3×25 mL). The combined organic layers were dried over sodium sulphate, filtered, and evaporated. The brown residue was purified by flash chromatography (ethyl acetate:Hexane, from 25% to 35%) to afford 37 (52 mg, 50%, 22% for two steps) as a colorless oil.

$^1$H NMR (300 MHz, CDCl$_3$) δ 8.49 (d, J=5.4 Hz, 1H), 8.36 (dd, J=4.6, 1.5 Hz, 1H), 7.97 (dd, J=7.9, 1.5 Hz, 1H), 7.35-7.10 (m, 7H), 2.31 (br s, 6H).

MS (ESI) m/z: 408 (M+23)$^+$, 386 (M+1)$^+$.

EXAMPLE 45

Compound 58

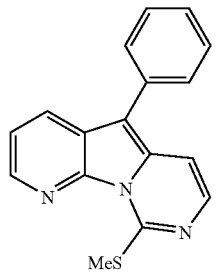

A mixture of 37 (51 mg, 0.13 mmol), trifluoroacetic acid (22 μL, 0.28 mmol) and triethylsilane (0.17 mL, 1.07 mmol) were poured in a Young tube containing 1.2-dichloroethane (0.5 mL). The sealed reaction vessel was heated at 85° C. for 22 h. After cooling, the vessel was opened and the contents diluted with chloroform (25 mL). The solution was neutralised with a saturated aqueous solution of sodium bicarbonate (30 mL) and the layers separated. The aqueous layer was repeatedly extracted with chloroform and the combined organic layers were dried over sodium sulphate, filtered, and concentrated. The dark red residue was purified by flash chromatography (ethyl acetate:hexane, from 1:4 to 1:3) to afford 58 (0.19 g, 66%) as a yellow solid.

$^1$H NMR (300 MHz, CDCl$_3$) δ 8.62 (dd, J=4.6, 1.5 Hz, 1H), 8.29 (dd, J=8.2, 1.6 Hz, 1H), 7.67-7.63 (m, 2H), 7.58 (d, J=6.5 Hz, 1H), 7.57-7.53 (m, 2H), 7.45 (dd, J=8.1, 4.6 Hz, 1H), 7.42-7.37 (m, 1H), 7.33 (d, J=6.6 Hz, 1H), 2.76 (s, 3H).

$^{13}$C NMR (75 MHz, CDCl$_3$) δ 154.3, 141.8, 136.5, 133.3, 129.0, 128.9, 126.6, 121.4, 119.9, 106.9, 14.5.

MS (ESI) m/z: 292 (M+1)$^+$.

EXAMPLE 46

Compound 63

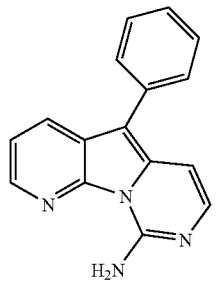

Aqueous NH₄OH (5 mL, 32%) was added to a solution of 58 (19 mg, 0.065 mmol) in 1.4-dioxane (2 mL). The yellow mixture was stirred for 24 h at 90° C. in a sealed tube. The resulting yellow mixture was evaporated at reduced pressure and the yellow residue was purified by flash chromatography using CH₂Cl₂:MeOH (1%) to CH₂Cl₂:MeOH (2%) as eluent to afford 63 (8 mg, 98% BRSM) as a yellow solid.

¹H NMR (300 MHz, CDCl₃) δ 8.35 (dd, J=4.3, 1.4 Hz, 1H), 8.23 (dd, J=7.9, 1.3 Hz, 1H), 7.62-7.58 (m, 2H), 7.54-7.37 (m, 2H), 7.39 (dd, J=8.1, 4.4 Hz, 1H), 7.38-7.31 (m, 2H), 6.92 (d, J=6.6 Hz, 1H).

MS (ESI) m/z: 261 (M+1)⁺.

EXAMPLE 47

Compound 38

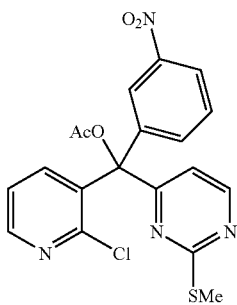

A solution of nBuLi (0.83 mL, 2.075 mmol, 2.5 M in hexane) was added dropwise to a solution of 1-Iodo-2-nitrobenzene (0.51 g, 2.0 mmol) in tetrahydrofuran (8 mL) at −78° C. The black mixture was stirred at −78° C. for 10 min and a solution of 31 (0.45 g, 1.7 mmol) in tetrahydrofuran (8 mL) was added via canula. The dark mixture was slowly warmed up until −40° C. for 2 h. Acetyl chloride (0.36 mL, 5.0 mmol) was added and the mixture was stirred for 2 h at 23° C. Saturated aqueous solution of sodium bicarbonate (50 mL) was added and the aqueous layer was extracted with diethyl ether (2×50 mL). The combined organic extracts were dried over MgSO₄, filtered, and evaporated. The brown residue was purified by flash chromatography (ethyl acetate:hexane, from 1:4 to 1:1) to afford 38 (0.14 g, 19%) as a pale brown oil.

¹H NMR (300 MHz, CDCl₃) δ 8.52 (d, J=5.9 Hz, 1H), 8.41 (dd, J=4.6, 1.7 Hz, 1H), 8.34 (t, J=1.9 Hz, 1H), 8.17-8.14 (m, 1H), 8.03 (dd, J=7.8, 1.7 Hz, 1H), 7.78-7.72 (m, 1H), 7.50 (t, J=8.1 Hz, 1H), 7.31 (dd, J=8.1, 4.6 Hz. 1H), 7.19 (d, J=5.2 Hz, 1H), 2.37 (s, 3H), 2.35 (s, 3H).

MS (ESI) m/z: 453 (M+23)⁺, 431 (M+1)⁺.

EXAMPLE 48

Compound 59

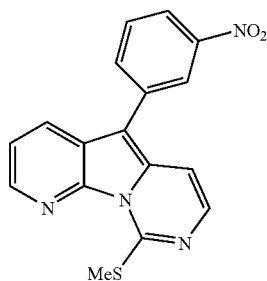

A mixture of 38 (140 mg, 0.32 mmol), trifluoroacetic acid (53 μL, 0.68 mmol) and triethylsilane (0.42 mL, 2.6 mmol) were poured in a Young tube containing 1.2-dichloroethane (2 mL). The reaction vessel was sealed and heated at 90° C. for 22 h. After cooling, the vessel was opened and the contents diluted with chloroform (100 mL). The solution was neutralised with a saturated aqueous solution of sodium bicarbonate (50 mL) and the layers separated. The aqueous layer was repeatedly extracted with chloroform and the combined organic layers were dried over sodium sulphate, filtered, and concentrated. The dark red residue was purified by flash chromatography (ethyl acetate:hexane, from 1:4 to 1:3) to afford 59 (72 mg, 23%) as an orange solid.

¹H NMR (300 MHz, CDCl₃) δ 8.65 (dd, J=4.6, 1.5 Hz, 1H), 8.50 (br t, J=2.0 Hz, 1H), 8.27 (dd, J=8.2, 1.5 Hz, 1H), 8.21 (ddd, J=8.3, 2.4, 1.0 Hz, 1H), 7.97 (dt, J=7.8, 1.7 Hz, 1H), 7.73-7.67 (m, 2H), 7.50 (dd, J=8.3, 4.6 Hz, 1H), 7.31 (d, J=6.8 Hz, 1H), 2.76 (s, 3H).

MS (ESI) m/z: 337 (M+1)⁺.

EXAMPLE 49

Compound 64

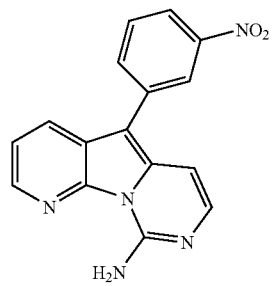

Aqueous NH₄OH (6 mL, 32%) was added to a solution of 59 (48 mg, 0.14 mmol) in 1.4-dioxane (5 mL). The yellow mixture was heated for 48 h at 105° C. in a sealed tube. The resulting brown mixture was evaporated at reduced pressure and the yellow residue was purified by flash chromatography (CH₂Cl₂:MeOH, from 1% to 3%) to afford 64 (5 mg, 12%) as a yellow solid.

¹H NMR (300 MHz, CDCl₃) δ 8.50 (br t, J=1.8 Hz, 1H), 8.39 (dd, J=4.6, 1.5 Hz, 1H), 8.22 (dd, J=8.1, 1.5 Hz, 1H), 8.19-8.12 (m, 1H), 7.92 (dt, J=7.6, 1.5 Hz, 1H), 7.69-7.61 (m, 1H), 7.48-7.41 (m, 2H), 6.91 (d, J=6.8 Hz, 1H).

MS (ESI) m/z: 306 (M+1)⁺.

EXAMPLE 50

Compound 39

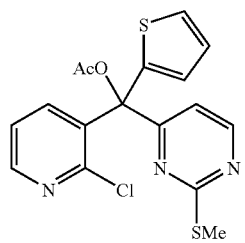

A solution of n-BuLi (1.4 mL, 3.50 mmol, 2.5 M in hexane) was added dropwise to a solution of 2-Iodothiophene (0.37 mL, 3.40 mmol) in tetrahydrofuran (12 mL) at −78° C. The brown red mixture was stirred at −78° C. for 15 min and a solution of 31 (0.75 g, 2.83 mmol) in tetrahydrofuran was added via canula. The brown mixture was stirred at −78° C. for 2 h. Acetyl chloride (0.6 mL, 17.0 mmol) was added and the mixture was stirred for 2 h at 23° C. Saturated aqueous solution of sodium bicarbonate (50 mL) was added and the aqueous layer was extracted with CH$_2$Cl$_2$ (2×50 mL). The combined organic layers were dried over sodium sulphate, filtered, and concentrated. The brown residue was purified by flash chromatography (ethyl acetate:hexane, from 1:3 to 1:2) to afford 39 (0.61 g) as a pale brown solid. 39 was found slightly unstable and it was used immediately for the next step.

MS (ESI) m/z: 392 (M+1)$^+$.

EXAMPLE 51

Compound 60

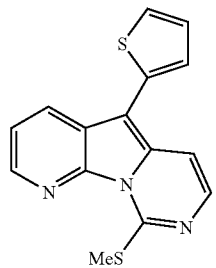

A mixture of 39 (610 mg, 1.56 mmol), trifluoroacetic acid (0.25 mL, 3.27 mmol) and triethylsilane (2 mL, 12.4 mmol) were poured in a Young tube containing 1.2-dichloroethane (2.5 mL). The reaction vessel was sealed and heated at 90° C. for 16 h. After cooling, the vessel was opened and the contents diluted with CH$_2$Cl$_2$ (250 mL). The solution was neutralised with a saturated aqueous solution of sodium bicarbonate (200 mL) and the layers separated. The aqueous layer was repeatedly extracted with CH$_2$Cl$_2$ and the combined organic layers were dried over sodium sulphate, filtered, and concentrated. The dark red residue was purified by flash chromatography (ethyl acetate:hexane, from 1:4 to 1:2) to afford 60 (72 mg, 23%) as a yellow solid.

$^1$H NMR (300 MHz, CDCl$_3$) δ 8.61 (dd, J=4.6, 1.7 Hz, 1H), 8.40 (dd, J=8.3, 1.7 Hz, 1H), 7.63 (d, J=6.7 Hz, 1H), 7.51-7.45 (m, 2H), 7.39 (d, J=5.4 Hz, 1H), 7.31-7.29 (m, 1H), 7.22 (dd, J=5.1, 3.6 Hz, 1H).

MS (ESI) m/z: 298 (M+1)$^+$.

EXAMPLE 52

Compound 65

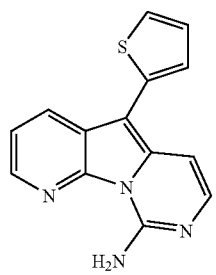

Aqueous NH$_4$OH (2.5 mL, 32%) was added to a solution of 60 (13.5 mg, 0.045 mmol) in 1.4-dioxane (1.5 mL). The yellow mixture was heated for 12 h at 90° C. in a sealed tube. The resulting yellow mixture was evaporated at reduced pressure and the yellow residue was purified by flash chromatography (CH$_2$Cl$_2$:MeOH, from 2% to 3%) to afford 65 (8 mg, 67%) as a yellow solid.

$^1$H NMR (300 MHz, CDCl$_3$) δ 8.39-8.32 (m, 2H), 7.42 (dd, J=7.8, 4.8 Hz, 1H), 7.38 (d, J=6.6 Hz, 1H), 7.34 (d, J=5.4 Hz, 1H), 7.29-7.26 (m, 1H), 7.19 (dd, J=5.1, 3.7 Hz, 1H), 7.08 (d, J=6.6 Hz, 1H).

MS (ESI) m/z: 267 (M+1)$^+$.

EXAMPLE 53

Compound 40

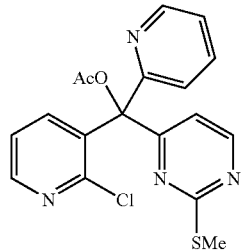

A solution of n-BuLi (0.94 mL, 2.36 mmol, 2.5 M in hexane) was added dropwise to a solution of 2-bromopyridine (0.21 mL, 2.27 mmol) in tetrahydrofuran (10 mL) at −78° C. The brown red mixture was stirred at −78° C. for 15 min and a solution of 31 (0.5 g, 1.89 mmol) in tetrahydrofuran was added via canula. The brown mixture was stirred at −78° C. for 1 h. Acetyl chloride (0.4 mL, 5.67 mmol) was added and the mixture was stirred for 2 h at 23° C. Saturated aqueous solution of sodium bicarbonate (50 mL) was added and the aqueous layer was extracted with CH$_2$Cl$_2$ (2×50 mL). The combined organic layers were dried over sodium sulphate, filtered, and concentrated. The orange residue was purified by flash chromatography (ethyl acetate:hexane, from 1:3 to 1:1) to afford 40 (0.25 g, 35%) as a colorless oil.

$^1$H NMR (300 MHz, CDCl$_3$) δ 8.49 (dt, J=4.6, 1.5 Hz, 1H), 8.44 (d, J=5.3, 1H), 8.35 (dd, J=4.9, 2.0 Hz, 1H), 7.91 (dd, J=8.1, 2.0 Hz, 1H), 7.71-7.61 (m, 2H), 7.30 (d, J=5.4 Hz, 1H), 7.26-7.15 (m, 3H), 2.40 (s, 3H), 2.29 (s, 3H).

MS (ESI) m/z: 387 (M+1)$^+$.

EXAMPLE 54

Compound 55

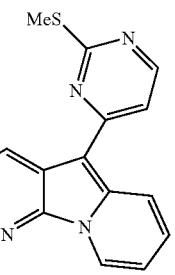

A mixture of 40 (250 mg, 0.65 mmol), trifluoroacetic acid (0.1 mL, 1.36 mmol) and triethylsilane (0.83 mL, 5.18 mmol) were poured in a Young tube containing 1.2-dichloroethane (2 mL). The reaction vessel was sealed and heated at 90° C. for 24 h. After cooling, the vessel was opened and the contents diluted with $CH_2Cl_2$ (150 mL). The solution was neutralised with a saturated aqueous solution of sodium bicarbonate (100 mL) and the layers separated. The aqueous layer was repeatedly extracted with $CH_2Cl_2$ and the combined organic layers were dried over sodium sulphate, filtered, and concentrated. The dark red residue was purified by flash chromatography (ethyl acetate:hexane, from 1:3 to 1:1) to afford 55 (34 mg, 19%) as a yellow solid.

$^1$H NMR (300 MHz, $CDCl_3$) δ 8.94 (dt, J=7.1, 1.2 Hz, 1H), 8.64-8.58 (m, 2H), 8.48 (dd, J=4.6, 1.4 Hz, 1H), 8.46 (d, J=5.4 Hz, 1H), 7.49 (dd, J=8.3, 4.6 Hz, 1H), 7.40 (m, 2H), 6.85 (td, J=7.1, 1.3 Hz, 1H), 2.70 (s, 3H).

MS (ESI) m/z: 293 (M+1)$^+$.

EXAMPLE 55

Compound 56

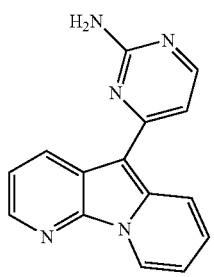

A solution of mCPBA (34 mg, 0.14 mmol, 70%) in $CH_2Cl_2$ (2 mL), previously dried over sodium sulphate, was dropwise added to a solution of 55 (34 mg, 0.12 mmol) in $CH_2Cl_2$ (3 mL) at 0° C. The yellow solution was stirred for 30 min at 0° C. A saturated aqueous solution of $Na_2S_2O_3$ (5 mL) was added and the organic layer was washed with a saturated aqueous solution of sodium bicarbonate (10 mL). The combined aqueous layers were extracted with $CH_2Cl_2$ (3×10 mL). The combined organic layers were dried over sodium sulphate, filtered and, concentrated. The yellow residue was poured in a sealed tube with 1.4-dioxane (4 mL) and a $NH_4OH$ solution (8 mL, 32%) was added. The brown mixture was heated for 14 h at 85° C. The resulting yellow mixture was evaporated in vacuo. The yellow solid was purified by flash chromatography ($CH_2Cl_2$:MeOH, from 1% to 3%) to afford 56 (6 mg, 20% for 2 steps) as a yellow solid.

$^1$H NMR (300 MHz, $CDCl_3$) δ 8.94 (d, J=6.8 Hz, 1H), 8.64 (dd, J=8.0, 1.4 Hz, 1H), 8.54 (d, J=9.3 Hz, 1H), 8.46 (dd, J=4.4, 1.5 Hz, 1H), 8.21 (d, J=5.6 Hz, 1H), 7.48 (dd, J=8.3, 4.6 Hz, 1H), 7.36 (ddd, J=9.3, 6.6, 1.3 Hz, 1H), 7.09 (d, J=5.6 Hz, 1H), 6.85 (td, J=6.8, 1.1 Hz, 1H).

MS (ESI) m/z 262 (M+1)$^+$.

EXAMPLE 56

Compound 41

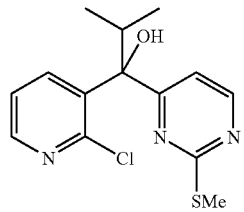

i-PrMgCl (0.75 mL 1.5 mmol, 2.0 M in tetrahydrofuran) was added dropwise to a solution of 31 (0.40 g, 1.5 mmol) in tetrahydrofuran (5 mL) at 0° C. and the mixture was stirred at 0° C. for 3 h. Saturated aqueous solution of ammonium chloride (25 mL) was added and the aqueous layer was extracted with ethyl acetate (3×25 mL). The combined organic layers were dried over sodium sulphate, filtered, and concentrated. The residue was purified by flash chromatography (ethyl acetate:Hexane, 33%) to afford 41 (0.28 g, 61%) as a transparent oil.

$^1$H NMR ($CDCl_3$, 300 MHz) δ 0.84 (d, J=6.6 Hz, 3H), 0.98 (d, J=6.6 Hz, 3H), 2.53 (s, 3H), 3.01 (sept, J=6.6 Hz, 1H), 5.17 (s, 1H), 7.18 (d, J=5.5 Hz, 1H), 7.30 (dd, J=7.8, 4.6 Hz, 1H), 8.24 (dd, J=7.8, 1.7 Hz, 1H), 8.30 (dd, J=4.6, 1.7 Hz, 1H), 8.47 (d, J=5.5 Hz, 1H).

MS (ESI) m/z: 258 (M+1)$^+$.

EXAMPLE 57

Compound 61

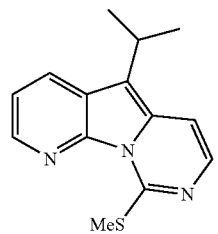

A solution of 41 (0.28 g, 0.91 mmol) and trifluoroacetic acid (0.15 mL, 2.0 mmol) in 1.2-dichloroethane (3 mL) was transferred to a Young tube fitted with a rubber septum, containing triethylsilane (1.28 mL, 8 mmol). Under a strong flow of Argon, the septum was replaced with a Teflon screw cap, sealed and the reaction vessel was heated at 100° C. for 48 h. After cooling, the vessel was opened and the contents diluted with $CH_2Cl_2$ (20 mL). The solution was neutralized with a saturated aqueous solution of sodium bicarbonate (20 mL) and the layers separated. The aqueous layer was repeatedly extracted with $CH_2Cl_2$ and the combined organic layers were dried over sodium sulphate, filtered, and concentrated. Purification of the crude material was achieved by flash chromatography (ethyl acetate:Hexane, 5%) to afford 61 as a yellow oil (176 mg, 75%).

$^1$H NMR ($CDCl_3$, 300 MHz) δ 1.47 (d, J=7.1 Hz, 6H), 2.69 (s, 3H), 3.44 (sept, J=7.1 Hz, 1H), 7.06 (d, J=6.6 Hz, 1H), 7.35

(dd, J=8.1, 4.6 Hz, 1H), 7.44 (d, J=6.6 Hz, 1H), 8.16 (dd, J=8.1, 1.5 Hz, 1H), 8.52 (dd, J=4.6, 1.5 Hz, 1H).

MS (ESI) m/z: 258, (M+1)⁺.

EXAMPLE 58

Compound 66

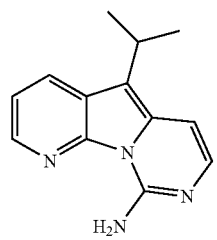

A solution of 61 (146 mg, 0.56 mmol) in 1.4-dioxane (15 mL) was treated with aqueous NH₄OH (30 mL, 32%) in a sealed tube at 90° C. for 24 h. The reaction mixture was evaporated and chromatographed (ethyl acetate:hexane, 33%) to give 66 (50 mg, 39%) as a yellow solid.

¹H NMR (CDCl₃, 300 MHz) δ 1.46 (d, J=7.1 Hz, 6H), 3.41 (sept, J=7.1 Hz, 1H), 6.70 (d, J=6.8 Hz, 1H), 7.27 (d, J=6.8 Hz, 1H), 7.31 (dd, J=8.1, 4.6 Hz, 1H), 8.11 (d, J=8.1 Hz, 1H), 8.29 (d, J=4.6, 1.5 Hz, 1H).

MS (ESI) m/z: 227, (M+1)⁺.

EXAMPLE 59

Compound 25

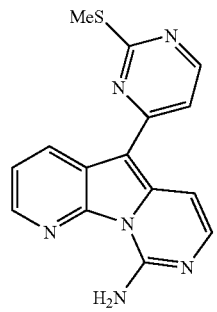

NH₄OH solution (3 mL, 32%) was added to a solution of 9 (12 mg, 0.035 mmol) in 1.4-dioxane (2 mL). The brown mixture was heated for 14 h at 85° C. in a sealed tube. The resulting yellow mixture was evaporated in vacuo, CH₂Cl₂ (5 mL) was added, dried over sodium sulphate, filtered, and the solvent evaporated at reduced pressure. The yellow solid was purified by flash chromatography (CH₂Cl₂:MeOH, from 2% to 3%) to afford 25 (8 mg, 73%) as a yellow solid.

¹H NMR (300 MHz, CDCl₃) δ 8.72 (dd, J=8.1, 1.5 Hz, 1H), 8.48 (d, J=5.4 Hz, 1H), 8.39 (dd, J=4.8, 1.6 Hz, 1H), 7.66 (d, J=6.8 Hz, 1H), 7.56 (d, J=6.7 Hz, 1H), 7.48 (dd, J=8.1, 4.6 Hz, 1H), 7.32 (d, J=5.3 Hz, 1H), 2.67 (s, 3H).

MS (ESI) m/z: 309 (M+1)⁺.

EXAMPLE 60

Compound 68

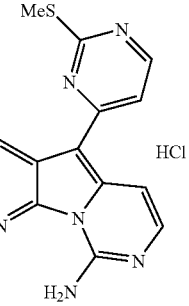

Compound 25 (0.6 g, 1.95 mmol) was treated with HCl solution in 1.4-dioxane (45 mL, 5.0 N) and stirred for 20 h at 23° C. The brown suspension was evaporated, washed with diethyl ether (30 mL), dioxane (30 mL) and filtered to afford 68 (0.65 g) as an orange solid.

¹H NMR (300 MHz, CD₃OD) δ 8.89 (dd, J=8.3, 1.3 Hz, 1H), 8.69 (d, J=5.4 Hz, 1H), 8.68 (m, 1H), 7.89 (d, J=7.5 Hz, 1H), 7.85 (d, J=5.9 Hz, 1H), 7.78 (dd, J=7.8, 4.9 Hz, 1H), 7.59 (d, J=7.9 Hz, 1H), 2.81 (s, 3H).

EXAMPLE 61

Compounds 69 and 26

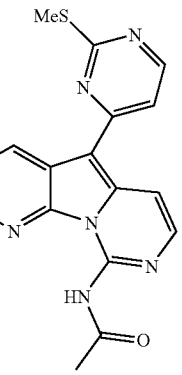

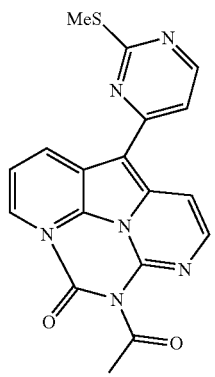

Acetyl chloride (1.5 mL, 0.019 mmol) was added to a solution of 25 (6 mg, 0.019 mmol) and Et$_3$N (3 mL, 0.029 mmol) in tetrahydrofuran (2 mL). The yellow solution was stirred at 23° C. overnight and evaporated at reduced pressure. The yellow residue was dissolved in CH$_2$Cl$_2$ (5 ml) and washed with a saturated aqueous solution of sodium bicarbonate (4 mL). The organic layer was dried over sodium sulphate, filtered and evaporated under reduced pressure. The yellow residue was purified by flash chromatography (CH$_2$Cl$_2$:MeOH, from 0.5% 1%) to afford 69 (2 mg, 39% BRSM) and 26 (2.5 mg, 47% BRSM) as a yellow oils.

69:

$^1$H NMR (300 MHz, CDCl$_3$) δ 8.77 (dd, J=8.2, 1.6 Hz, 1H), 8.54 (d, J=5.3 Hz, 1H), 8.52 (dd, J=4.9, 1.5 Hz, 1H), 7.93 (d, J=6.6 Hz, 1H), 7.83 (d, J=6.7 Hz, 1H), 7.58 (dd, J=8.2, 4.6 Hz, 1H), 7.37 (d, J=5.4 Hz, 1H), 2.69 (s, 3H), 2.67 (s, 3H).

26:

$^1$H NMR (300 MHz, CDCl$_3$) δ 8.65 (dd, J=8.3, 1.7 Hz, 1H), 8.58 (d, J=5.4 Hz, 1H), 8.54 (dd, J=6.1, 1.7 Hz, 1H), 8.39 (d, J=6.6 Hz, 1H), 7.92 (d, J=6.7 Hz, 1H), 7.56 (dd, J=8.2, 4.6 Hz, 1H), 7.38 (d, J=5.6 Hz, 1H), 2.69 (s, 3H), 2.42 (s, 6H).

MS (ESI) m/z: 415 (M+23)$^+$.

EXAMPLE 62

Compound 28

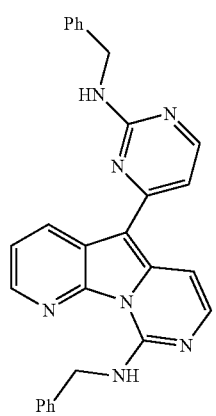

A mixture of benzylamine (0.5 mL, 4.5 mmol) and 27 (160 mg, 0.45 mmol) in tetrahydrofuran (2.5 mL) was refluxed for 14 h. Solvent was evaporated and the yellow residue was purified by flash chromatography (CH$_2$Cl$_2$:MeOH, from 99:1 to 97:3) to afford 28 (90 mg, 44%) as a yellow oil.

$^1$H NMR (300 MHz, CDCl$_3$) δ 10.44 (br s, 1H), 8.51 (d, J=6.0 Hz, 1H), 8.29 (d, J=6.2 Hz, 1H), 8.26 (d, J=1.1 Hz, 1H), 7.60 (d, J=6.6 Hz, 1H), 7.48-7.28 (m, 12H), 6.99 (d, J=5.5 Hz, 1H), 5.81 (br s, 1H), 4.97 (d, J=5.7 Hz, 2H), 4.76 (d, J=5.8 Hz, 2H).

EXAMPLE 63

Compounds 72 and 73

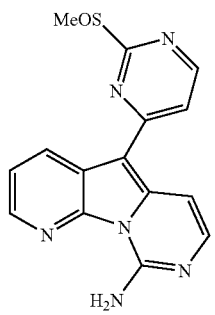

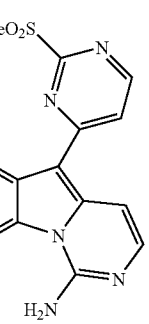

A solution of mCPBA (70 mg, 0.30 mmol, 70%) in CH$_2$Cl$_2$ (3 mL), previously dried over sodium sulphate, was added dropwise to a solution 25 (39 mg, 0.13 mmol) in CH$_2$Cl$_2$ (7 mL). The yellow solution was stirred for 2 h at 23° C. A saturated aqueous solution of Na$_2$S$_2$O$_3$ (5 mL) was added and the organic layer was washed with a saturated aqueous solution of sodium bicarbonate (5 mL). The combined aqueous layers were extracted with CH$_2$Cl$_2$ (3×20 mL). The combined organic layers were dried over sodium sulphate, filtered, and concentrated. The yellow residue was purified by flash chromatography (CH$_2$Cl$_2$:MeOH, from 2% to 5%) to afford 72 (15 mg, 35%) as a yellow oil and 73 (25 mg, 58%) as a yellow solid.

72:

$^1$H NMR (300 MHz, CDCl$_3$) δ 8.86 (dd, J=8.1, 1.5 Hz, 1H), 8.74 (d, J=5.6 Hz, 1H), 8.43 (dd, J=4.6, 1.3 Hz, 1H), 7.77 (d, J=6.8 Hz, 1H), 7.72 (d, J=6.6 Hz, 1H), 7.67 (d, J=5.8 Hz, 1H), 7.54 (dd, J=8.0, 4.6 Hz, 1H), 3.02 (s, 3H).

MS (ESI) m/z: 325 (M+1)$^+$.

73:

$^1$H NMR (300 MHz, CDCl$_3$) δ 8.80 (dd, J=8.1, 1.4 Hz, 1H), 8.71 (d, J=5.6 Hz, 1H), 8.41 (dd, J=4.8, 1.4 Hz, 1H), 7.76 (d,

J=5.6 Hz, 1H), 7.74 (d, J=6.4 Hz, 1H), 7.64 (d, J=6.4 Hz, 1H), 7.52 (dd, J=8.2, 4.8 Hz, 1H), 3.40 (s, 3H).

EXAMPLE 64

Compound 70

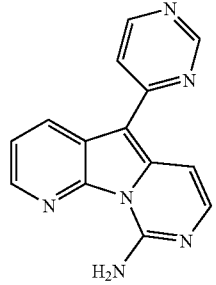

A suspension of 25 (29 mg, 0.09 mmol) in 1.2 dichloroethane (0.5 mL) was treated with Pd/C (3 mg, 10%), TFA (14 μL, 0.18 mmol) and Et$_3$SiH (110 μL, 0.7 mmol) in a sealed tube at 100° C. for 72 h. The reaction mixture was dissolved with CH$_2$Cl$_2$:MeOH (20:1) and washed with a saturated aqueous solution of sodium bicarbonate. The organic layer was dried over sodium sulphate, filtered, and evaporated. The residue was chromatographed (CH$_2$Cl$_2$:MeOH, from 50:1 to 95:5) to recover 25 (6.5 mg) and give 70 as a yellow solid (7.5 mg, 39% BRSM).

$^1$H NMR (CDCl$_3$:CD$_3$OD 9:1, 300 MHz) δ 9.02 (s, 1H), 8.60 (dd, J=8.3, 1.5 Hz, 1H), 8.50 (d, J=5.6 Hz, 1H), 8.29 (dd, J=4.9, 1.5 Hz, 1H), 7.59 (d, J=5.6 Hz, 1H), 7.49-7.43 (m, 2H), 7.38 (dd, J=8.3, 4.9 Hz, 1H).

MS (ESI) m/z: 263 (M+1)$^+$.

EXAMPLE 65

Compound 71

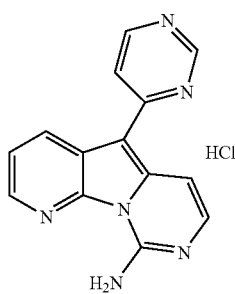

Compound 70 (6.5 mg, 0.025 mmol) was treated with HCl in 1.4-dioxane (1.0 mL, 3.8 M) for 15 min. The reaction mixture was evaporated and washed with diethyl ether, dissolved in MeOH and evaporated to give 71 as an orange solid (7.0 mg, 94%).

$^1$H NMR (CD$_3$OD, 300 MHz) δ 9.35 (s, 1H), 8.97 (dd, J=8.1, 1.5 Hz, 1H), 8.88 (d, J=6.1 Hz, 1H), 8.68 (dd, J=4.9, 1.5 Hz, 1H), 8.27 (dd, J=6.3, 1.2 Hz, 1H), 8.04 (d, J=7.6 Hz, 1H), 7.78 (dd, J=8.3, 5.1 Hz, 1H), 7.57 (d, J=7.3 Hz, 1H).

MS (ESI) m/z: 263 (M)$^+$.

EXAMPLE 66

Compound 74

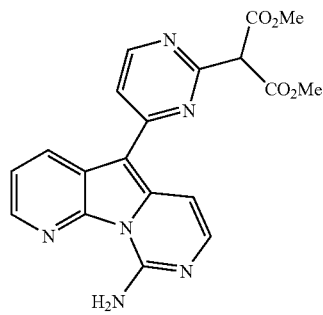

Dimethylmalonate (0.013 mL, 0.11 mmol) was added dropwise to a suspension of NaH (4.4 mg, 0.1 mmol, 60%) in tetrahydrofuran (2.5 mL) at 23° C. After 10 min, 73 (4 mg, 0.011 mmol) was added in one portion and the yellow slurry was stirred at 23° C. overnight. The reaction was followed by TLC and only starting material was observed. The mixture was refluxed for 3 h, cooled and quenched with an saturated aqueous solution of ammonium chloride. The aqueous layer was extracted with CH$_2$Cl$_2$ (3×10 mL) and the combined organic layers were dried over sodium sulphate, filtered, and evaporated. The yellow residue was purified by flash chromatography (CH$_2$Cl$_2$:MeOH, from 1% to 3%) to afford 74 (1.5 mg, 36%) as a yellow solid.

$^1$H NMR (300 MHz, CDCl$_3$) δ 8.72 (dd, J=8.2, 1.5 Hz, 1H), 8.69 (d, J=5.3 Hz, 1H), 8.39 (dd, J=4.6, 1.5 Hz, 1H), 7.69 (d, J=5.9 Hz, 1H), 7.59 (d, J=6.6 Hz, 1H), 7.58 (d, J=6.6 Hz, 1H), 7.50 (dd, J=8.2, 4.7 Hz, 1H), 4.23 (s, 1H), 3.85 (s, 6H).

MS (ESI) m/z: 415 (M+23)$^+$, 393 (M+1)$^+$.

EXAMPLE 67

Compound 75

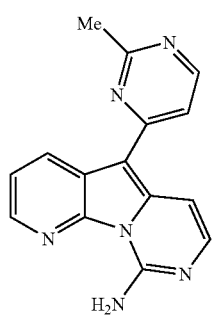

A solution of methylmagnesiumbromide (0.037 mL, 3 M in tetrahydrofuran) was added dropwise to a solution of 73 (25 mg, 0.073 mmol) in tetrahydrofuran (5 mL) at 0° C. The brown mixture was stirred at 0° C. for 2 h and 1 h at 23° C. Saturated aqueous solution of ammonium chloride (25 mL) was added and the aqueous layer was extracted with CH$_2$Cl$_2$ (3×20 mL). The combined organic layers were dried over sodium sulphate, filtered, and concentrated. The orange residue was purified by flash chromatography (CH$_2$Cl$_2$:MeOH, from 1% to 3%) to afford 75 (14 mg, 69%) as a yellow solid.

$^1$H NMR (300 MHz, CDCl$_3$) δ 8.75 (dd, J=8.1, 1.5 Hz, 1H), 8.60 (d, J=5.6 Hz, 1H), 8.39 (dd, J=4.6, 1.5 Hz, 1H), 7.67 (d, J=6.6 Hz, 1H), 7.60 (d, J=6.6 Hz, 1H), 7.49 (dd, J=8.1, 5.0 Hz, 1H), (d, J=5.6 Hz, 1H), 2.81 (s, 3H).

MS (ESI) m/z: 277 (M+1)$^+$.

EXAMPLE 68

Compound 76

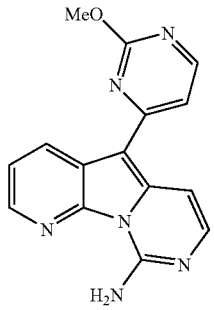

A solution of 72 (5.8 mg, 0.017 mmol) in MeOH (2 mL) was added to a solution of NaMeO in MeOH (2 mL) at 0° C. The yellow solution was stirred at 23° C. for 4 h, quenched with a saturated aqueous solution of ammonium chloride and extracted with ethyl acetate (3×10 mL). The combined organic layers were dried over sodium sulphate, filtered and evaporated under reduced pressure. The yellow residue was purified by flash chromatography (CH$_2$Cl$_2$:MeOH, from 1% to 3%) to afford 76 (2.6 mg, 53%) as a yellow solid.

$^1$H NMR (300 MHz, CDCl$_3$) δ 8.78 (dd, J=8.1, 1.5 Hz, 1H), 8.51 (d, J=5.4 Hz, 1H), 8.41 (dd, J=4.6, 1.5 Hz, 1H), 7.69 (d, J=6.6 Hz, 1H), 7.63 (d, J=6.6 Hz, 1H), 7.50 (dd, J=8.1, 4.6 Hz, 1H), 7.34 (d, J=5.4 Hz, 1H), 4.14 (s, 3H).

MS (ESI) m/z: 293 (M+1)$^+$.

EXAMPLE 69

Compound 81

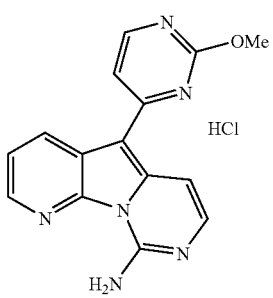

Compound 76 (30 mg) was suspended in a 5.3 N HCl solution in 1.4-dioxane (7 mL). The pale brown mixture was stirred at 23° C. for 2 h and evaporated in vacuo. CH$_2$Cl$_2$ (5 mL) was added, stirred for 1 min and evaporated again. 1.4-dioxane (5 mL) was added and the pale brown solid was filtered and washed with more 1.4-dioxane (3 mL) to afford 81 (30 mg).

$^1$H NMR (300 MHz, CD$_3$OD) δ 8.92 (dd, J=8.0, 1.1 Hz, 1H), 8.78-8.70 (m, 2H), 8.01 (d, J=7.8 Hz, 1H), 7.98 (d, J=6.3 Hz, 1H), 7.82 (dd, J=8.1, 4.6 Hz, 1H), 7.67 (d, J=5.4 Hz, 1H), 4.38 (s, 3H).

EXAMPLE 70

Compound 77

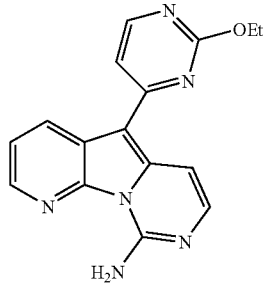

A solution of 72 (150 mg, 0.46 mmol) in EtOH (2 mL) was added to a solution of EtONa in EtOH (3 mL), freshly prepared by addition of an excess of Na in EtOH, at 0° C. The yellow solution was stirred at 23° C. for 5 h, quenched with a saturated aqueous solution of ammonium chloride and extracted with chloroform (3×10 mL). The combined organic layers were dried over sodium sulphate, filtered, and evaporated under reduced pressure. The yellow residue was purified by flash chromatography (CH$_2$Cl$_2$:MeOH, from 1% to 3%) to afford 77 (96 mg, 68%) as a yellow solid.

$^1$H NMR (300 MHz, CDCl$_3$) δ 8.74 (dd, J=8.2, 1.5 Hz, 1H), 8.47 (d, J=5.3 Hz, 1H), 8.39 (dd, J=4.6, 1.5 Hz, 1H), 7.67 (d, J=6.6 Hz, 1H), 7.59 (d, J=6.6 Hz, 1H), 7.48 (dd, J=8.2, 4.7 Hz, 1H), 7.29 (d, J=5.4 Hz, 1H), 4.55 (c, J=7.1 Hz, 2H), 1.52 (t, J=7.1 Hz, 3H).

MS (ESI) m/z: 329 (M+23)$^+$, 307 (M+1)$^+$.

EXAMPLE 71

Compound 82

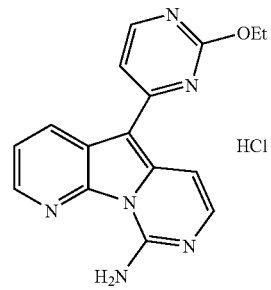

Compound 77 (35 mg, 0.11 mmol) was treated with HCl solution in 1.4-dioxane (4 mL, 5.3 M) and stirred for 3 h at 23° C. The suspension was evaporated, washed with diethyl ether and filtered to afford 82 (32 mg) as a yellow solid.

$^1$H NMR (300 MHz, CD$_3$OD) δ 8.91 (dd, J=8.2, 1.2 Hz, 1H), 8.77-8.63 (m, 2H), 7.98 (d, J=7.7 Hz, 1H), 7.98 (d, J=7.0

Hz, 1H), 7.81 (dd, J=7.9, 4.8 Hz, 1H), 7.64 (d, J=7.9 Hz, 1H), 4.69 (c, =7.0 Hz, 2H), 1.54 (t, J=7.0 Hz, 3H).

EXAMPLE 72

Compound 78

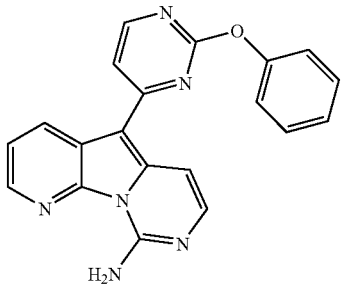

PhOH (116 mg, 1.2 mmol) was added to a suspension of NaH (50 mg, 1.2 mmol, 60%) in tetrahydrofuran (3 mL) at 0° C. A suspension of 72 (50 mg, 0.15 mmol) in tetrahydrofuran (5 mL) was added at 0° C. and the yellow solution was stirred at 23° C. for 24 h, quenched with a saturated aqueous solution of NaCl (50 mL) and extracted with chloroform (3×50 mL). The combined organic layers were dried over sodium sulphate, filtered, and evaporated under reduced pressure. The yellow residue was purified by flash chromatography (CH$_2$Cl$_2$: MeOH, from 0.5% to 1.5%) to afford 78 (20 mg, 53% BRSM) as a yellow solid.

$^1$H NMR (300 MHz, CDCl$_3$) δ 8.54 (d, J=5.4 Hz, 1H), 8.36 (dd, J=8.1, 1.3 Hz, 1H), 8.32 (dd, J=4.6, 1.2 Hz, 1H), 7.54-7.46 (m, 3H), 7.39 (d, J=5.4 Hz, 1H), 7.40-7.30 (m, 3H), 7.29-7.25 (m, 2H).

MS (ESI) m/z: 355 (M+1)$^+$.

EXAMPLE 73

Compound 79

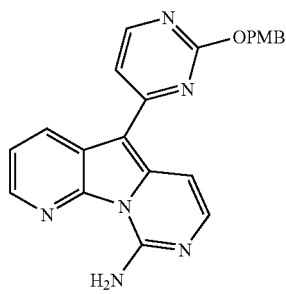

p-methoxybenzyl alcohol (0.085 mL, 0.67 mmol) was added to a suspension of NaH (27 mg, 0.67 mmol, 60%) in tetrahydrofuran (1 mL) at 0° C. A suspension of 72 (23 mg, 0.06 mmol) in tetrahydrofuran (2 mL) was added at 0° C. and the yellow solution was stirred at 23° C. for 5 h, quenched with a saturated aqueous solution of ammonium chloride (10 mL) and extracted with chloroform (3×10 mL). The combined organic layers were dried over sodium sulphate, filtered, and evaporated under reduced pressure. The yellow residue was purified by flash chromatography using CH$_2$Cl$_2$:MeOH (2%) as eluent. The yellow residue was washed with diethyl ether to afford 79 (12 mg, 46%) as a yellow solid.

$^1$H NMR (300 MHz, CDCl$_3$) δ 8.72 (dd, J=8.0, 1.6 Hz, 1H), 8.56 (d, J=5.8 Hz, 1H), 8.39 (dd, J=4.4, 1.6 Hz, 1H), 7.61-7.45 (m, 5H), 7.32 (d, J=5.4 Hz, 1H), 6.92 (d, J=7.2 Hz, 2H), 5.42 (br s, 2H), 3.82 (s, 3H).

MS (ESI) m/z: 399 (M+1)$^+$.

EXAMPLE 74

Compound 80

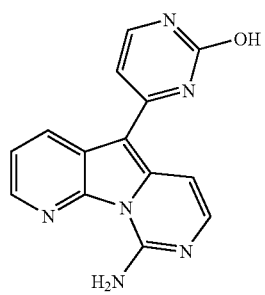

Compound 79 (10 mg, 0.025 mmol) was dissolved in neat triflic acid (0.5 mL) and stirred at 23° C. for 3 h. The flask was cooled to 0° C. and MeOH (1 mL) was added dropwise. Addition of aqueous NH$_4$OH (1 mL, 32%) produced a bright yellow precipitate wich was filtered and washed with ether to afford 80 (6 mg, 78%).

$^1$H NMR (300 MHz, DMSO-d$_6$) δ 8.85 (dd, J=8.5, 1.4 Hz), 8.45 (dd, J=4.6, 1.5 Hz), 7.85 (d, J=6.8 Hz, 1H), 7.76 (d, J=6.6 Hz, 1H), 7.66 (d, J=6.6 Hz, 1H), 7.60 (dd, J=8.1, 4.6 Hz), 6.88 (d, J=6.8 Hz, 1H).

$^{13}$C NMR (75 MHz, DMSO-d$_6$) δ 156.3, 153.1, 149.8, 145.7, 145.1, 143.1, 140.3, 140.1, 129.1, 121.6, 121.0, 101.3, 101.2, 99.0.

MS (ESI) m/z: 279 (M+1)$^+$.

EXAMPLE 75

Compound 84

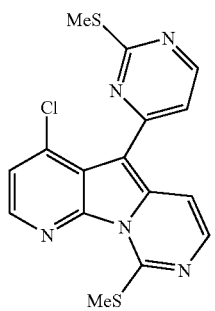

A solution of 52 (250 mg, 0.56 mmol) in POCl$_3$ (2 mL) was stirred at 100° C. in a sealed tube for 48 h. The reaction mixture was poured on ice and treated with a saturated aqueous solution of sodium bicarbonate until pH 7 and extracted with chloroform. The organic layer was dried over sodium sulphate, filtered, and evaporated. The residue was chromatographed (hexane:ethyl acetate, 4:1) to give 84 as a yellow solid (154 mg, 74%).

$^1$H NMR (CDCl$_3$, 300 MHz) δ 8.55 (d, J=5.1 Hz, 1H), 8.46 (d, J=5.1 Hz, 1H), 7.75 (d, J=6.6 Hz, 1H), 7.62 (d, J=6.6 Hz, 1H), 7.49 (d, J=5.1 Hz, 1H), 7.24 (d, J=5.1 Hz, 1H), 2.72 (s, 3H), 2.64 (s, 3H).

$^{13}$C NMR (CDCl$_3$, 75 MHz) δ 172.2, 160.1, 156.2, 155.0, 141.5, 139.7, 137.7, 135.1, 122.1, 119.0, 107.4, 102.8, 15.2, 14.4. Two quaternary signals overlaps.

MS (ESI) m/z: 374 (M+1)$^+$.

EXAMPLE 76

Compound 85

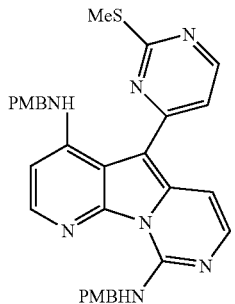

A solution of 84 (20 mg, 0.053 mmol) in p-methoxybenzylamine (0.2 mL) was stirred at 100° C. for 16 h. The reaction mixture was chromatographed (hexane:ethyl acetate, from 4:1 to 1:1) to give 85 as a yellow solid (29 mg, 97%).

$^1$H NMR (CDCl$_3$, 300 MHz) δ 11.02 (t, J=4.8 Hz, 1H), 9.28 (t, J=5.7 Hz, 1H), 8.42 (d, J=5.5 Hz, 1H), 7.86 (d, J=5.7 Hz, 1H), 7.56 (d, J=6.7 Hz, 1H), 7.38 (d, J=8.7 Hz, 2H), 7.31 (d, J=6.6 Hz, 1H), 6.94 (d, J=6.9 Hz, 1H), 6.91-6.85 (m, 4H), 6.35 (d, J=5.7 Hz, 1H), 4.82 (d, J=5.4 Hz, 2H), 4.52 (d, J=5.7 Hz, 2H), 3.80 (s, 3H), 3.78 (s, 3H), 2.50 (s, 3H).

MS (ESI) m/z: 564 (M+1)$^+$.

EXAMPLE 77

Compound 86

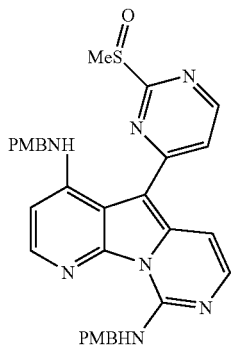

A solution of 85 (40 mg, 0.071 mmol) in CH$_2$Cl$_2$ (5 mL) was treated at −30° C. with a solution of mCPBA (20 mg, 0.09 mmol, 1.25 equiv, 77%) in CH$_2$Cl$_2$ (1 mL), warmed to 0° C. for 30 min and quenched with a saturated aqueous solution of Na$_2$S$_2$O$_3$. The reaction mixture was washed with a saturated aqueous solution of sodium bicarbonate (×4). The organic layer was dried over sodium sulphate, filtered, and evaporated. The residue was chromatographed (CH$_2$Cl$_2$:MeOH, 100:3) to give 86 as a yellow solid (26 mg, 63%).

$^1$H NMR (CDCl$_3$, 300 MHz) δ 11.26 (t, J=5.7 Hz, 1H), 10.18 (t, J=5.5 Hz, 1H), 8.58 (d, J=5.5 Hz, 1H), 7.83 (d, J=5.7 Hz, 1H), 7.67 (d, J=5.9 Hz, 2H), 7.38 (d, J=8.9 Hz, 2H), 7.29 (d, J=8.7 Hz, 2H), 7.02 (d, J=6.7 Hz, 1H), 6.89 (d, J=8.9 Hz, 2H), 6.82 (d, J=8.7 Hz, 2H), 6.35 (d, J=5.9 Hz, 1H), 4.83 (d, J=5.5 Hz, 2H), 4.70-4.63 (m, 2H), 3.80 (s, 3H), 3.76 (s, 3H), 2.90 (s, 3H).

MS (ESI) m/z: 602 (M+23)$^+$, 580 (M+1)$^+$.

EXAMPLE 78

Compound 89

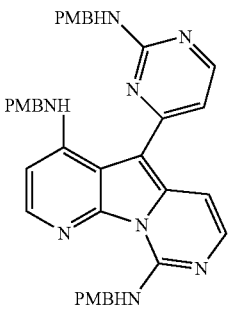

A solution of 84 (14 mg, 0.037 mmol) in dry CH$_2$Cl$_2$ (3 mL) was treated at −30° C. with a solution of mCPBA (18 mg, 0.08 mmol, 2.2 equiv, 77%) in CH$_2$Cl$_2$ (2 mL). The yellow solution was warmed to 0° C. for 30 min and treated with a saturated aqueous solution of Na$_2$S$_2$O$_3$ and washed with a saturated aqueous solution of sodium bicarbonate (3×). The organic layer was dried over sodium sulphate, filtered, and evaporated to give crude bis-sulphoxide which was treated with 4-methoxybenzylamine (0.1 mL, 0.76 mmol) at 100° C. for 15 h. The reaction mixture was chromatographed (CH$_2$Cl$_2$:MeOH, 98:2) to give 89 as a yellow oil (11 mg, 46%).

$^1$H NMR (CDCl$_3$, 300 MHz) δ 10.99 (t, J=5.5 Hz, 1H), 9.38 (br s, 1H), 8.22 (d, J=5.4 Hz, 1H), 7.96 (d, J=5.7 Hz, 1H), 7.51 (d, J=6.7 Hz, 1H), 7.40 (d, J=8.7 Hz, 2H), 7.33 (d, J=8.4 Hz, 2H), 7.08 (d, J=8.7 Hz, 2H), 6.97-6.80 (m, 8H), 6.44 (d, J=5.7 Hz, 1H), 4.84 (d, J=5.5 Hz, 2H), 4.35 (d, J=4.5 Hz, 2H), 4.29 (d, J=5.4 Hz, 2H), 3.81 (s, 3H), 3.78 (s, 3H), 3.70 (s, 3H). One NH signal was not observed.

MS (ESI) m/z: 653 (M+1)$^+$.

EXAMPLE 79

Compound 90

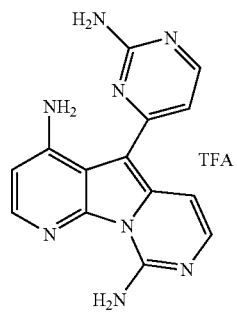

Compound 89 (10 mg, 0.015 mmol) was treated with triflic acid (0.2 mL) at 23° C. for 2 h. The reaction mixture was cooled to 0° C. and treated with MeOH (1 mL) and aqueous NH$_4$OH (1 mL, 32%). The reaction mixture was evaporated, dissolved in MeOH:H$_2$O 1:4 and applied to a reverse phase silica pack preconditioned with MeOH:H$_2$O 1:1. The column was washed with MeOH:H$_2$O 1:4 to remove salts and 90 was eluted with MeOH:H$_2$O 4:1 (1.5 mg, 34%).

Compound 90 is insoluble in MeOH and its trifluoroacetic salt was formed for NMR determination.

$^1$H NMR (CD$_3$OD plus one TFA drop, 300 MHz) δ 8.28 (d, J=6.8 Hz, 1H), 8.10 (d, J=5.7 Hz, 1H), 7.39-7.29 (m, 3H), 6.80 (d, J=5.6 Hz, 1H).

MS (ESI) m/z: 293 (M+1)$^+$.

EXAMPLE 80

Compound 91

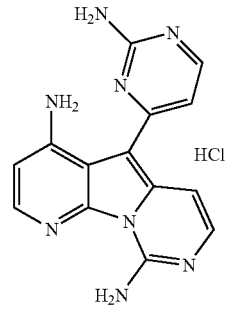

Compound 90 (19 mg, 0.065 mmol) was treated with anhydrous HCl in 1.4-dioxane (3 mL, 3.8 M) at 23° C. for 1 h. The reaction mixture was evaporated and washed with ethyl ether to give 91 as an orange solid (20 mg).

$^1$H NMR (CD$_3$OD, 300 MHz) δ8.31 (d, J=6.8 Hz, 1H), 8.11 (d, J=5.6 Hz, 1H), 7.41-7.32 (m, 3H), 6.82 (d, J=5.6 Hz, 1H).

MS (ESI) m/z: 293 (M)$^+$.

EXAMPLE 81

Compound 92

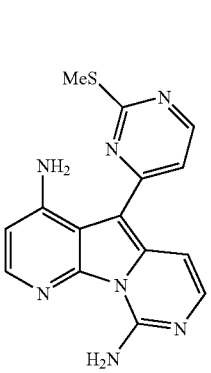

A solution of 85 (29 mg, 0.051 mmol) in triflic acid (0.2 mL) was stirred at 23° C. for 2 h. The reaction mixture was cooled at 0° C. and treated with MeOH (1 mL) and aqueous NH$_4$OH (32%) (1 mL), filtered, and washed with H$_2$O, MeOH and diethyl ether to give 92 as a yellow solid (10 mg, 61%).

$^1$H NMR (CDCl$_3$, 300 MHz) δ 8.63 (d, J=5.6 Hz, 1H), 8.07 (d, J=5.9 Hz, 1H), 7.48 (d, J=5.4 Hz, 1H), 7.18-7.17 (m, 2H), 6.72 (d, J=5.9 Hz, 1H), 2.63 (s, 3H).

MS (ESI) m/z: 324 (M+1)$^+$.

EXAMPLE 82

Compound 93

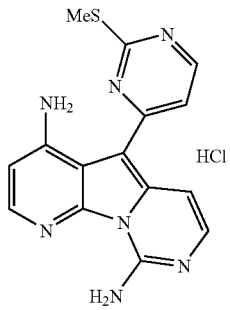

Compound 92 was treated with anhydrous HCl in 1.4-dioxane (1 mL, 3.8 M) for 15 min at 23° C. The reaction mixture was evaporated and washed with diethyl ether to give 93 as an orange solid (10 mg).

$^1$H NMR (CD$_3$OD, 300 MHz) δ 8.66 (d, J=5.1H, 1H), 8.09 (d, J=5.9 Hz, 1H), 7.50 (d, J=5.1 Hz, 1H), 7.21 (s, 2H), 6.74 (d, J=5.6 Hz, 1H), 2.64 (s, 3H).

MS (ESI) m/z: 324 (M)$^+$.

EXAMPLE 83

Compound 87

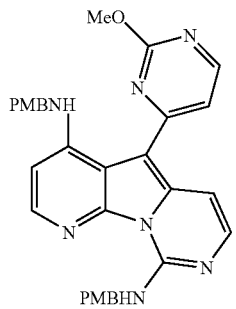

A solution of 86 was treated with a solution of MeONa in MeOH, prepared from Na (30 mg, 1.3 mmol) in MeOH (4 mL) at 23° C. for 16 h. The reaction mixture was evaporated, dissolved in $CH_2Cl_2$ and washed with a saturated aqueous solution of ammonium chloride. The organic layer was dried over sodium sulphate, filtered, and evaporated. The residue was chromatographed ($CH_2Cl_2$:MeOH, 100:3) to give 87 as a yellow solid (24 mg, 97%).

$^1$H NMR (CDCl$_3$, 300 MHz) δ 11.06 (t, J=5.4 Hz, 1H), 9.44 (t, J=5.1 Hz, 1H), 8.40 (d, J=5.4 Hz, 1H), 7.92 (d, J=5.7 Hz, 1H), 7.57 (d, J=6.6 Hz, 1H), 7.39 (d, J=9.0 Hz, 2H), 7.32 (d, J=8.7 Hz, 2H), 7.31 (d, J=5.4 Hz, 1H), 6.96 (d, J=6.9 Hz, 1H), 6.90 (d, J=8.7 Hz, 2H), 6.87 (d, J=8.7 Hz, 2H), 6.40 (d, J=6.0 Hz, 1H), 4.84 (d, J=5.4 Hz, 2H), 4.47 (d, J=5.4 Hz, 2H), 3.83 (s, 3H), 3.81 (s, 3H), 3.80 (s, 3H).

MS (ESI) m/z: 548 (M+1)$^+$.

EXAMPLE 84

Compound 88

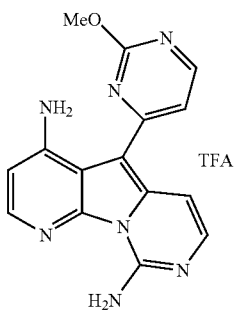

Compound 87 (23 mg, 0.04 mmol) was treated with TfOH (0.2 mL) at 23° C. for 2.5 h. The reaction mixture was cooled to 0° C. and treated with MeOH (1 mL) and aqueous NH$_4$OH (2 mL, 32%). The yellow solid formed was filtered through a Teflon filter and washed with H$_2$O (5 mL), EtOH (5 mL) and diethyl ether (5 mL) to give 88 (15 mg) as an orange solid. This compound is insoluble in chloroform and was characterized as its trifluoroacetic salt.

$^1$H NMR (CDCl$_3$:CD$_3$OD 9:1 plus 2 drops of deuterated TFA, 300 MHz) δ 8.56 (d, J=5.4 Hz, 1H), 8.02 (d, J=5.6 Hz, 1H), 7.31 (d, J=5.4 Hz, 1H), 7.12 (d, J=7.8 Hz, 1H), 6.97 (d, J=7.8 Hz, 1H), 6.62 (d, J=5.6 Hz, 1H), 4.07 (s, 3H).

MS (ESI) m/z: 308 (M+1)$^+$.

EXAMPLE 85

Compound 94

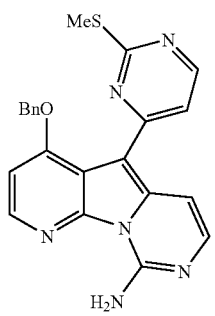

A solution of 52 (100 mg, 0.22 mmol) in 1.4-dioxane (10 mL) was treated with aqueous NH$_4$OH 32% (20 mL) in a sealed tube at 90° C. for 24 h. The reaction mixture was evaporated and chromatographed (CH$_2$Cl$_2$:MeOH, 97:3) to give 94 as a yellow solid (83 mg, 89%).

$^1$H NMR (CDCl$_3$, 300 MHz) δ 8.22 (d, J=5.5 Hz, 1H), 7.95 (d, J=6.8 Hz, 1H), 7.52 (d, J=6.8 Hz, 1H), 7.40 (d, J=6.5 Hz, 1H), 7.38-7.26 (m, 6H), 6.94 (d, J=5.5 Hz, 1H), 5.25 (s, 2H), 2.56 (s, 3H).

MS (ESI) m/z: 415 (M+1)$^+$.

EXAMPLE 86

Compound 95

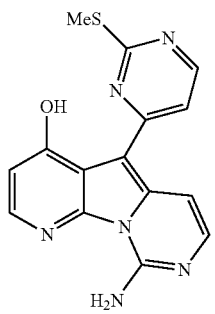

Compound 94 (62 mg, 0.15 mmol) was treated with TfOH (0.3 mL) at 23° C. for 1 h. The reaction mixture was treated with MeOH (1 mL), aqueous NH$_4$OH (2 mL, 32%), filtered and washed with H$_2$O (5 mL), MeOH (5 mL) and diethyl ether (4 mL). The solid obtained was chromatographed (CH$_2$Cl$_2$:MeOH, 95:5) to give 95 as a yellow solid (45 mg, 92%).

¹H NMR (CDCl₃:CD₃OD 9:1, 300 MHz) δ 8.38 (d, J=5.7 Hz, 1H), 8.09 (d, J=5.5 Hz, 1H), 7.53 (d, J=6.7 Hz, 1H), 7.34 (d, J=5.7 Hz, 1H), 7.00 (d, J=6.7 Hz, 1H), 6.82 (d, J=5.5 Hz, 1H), 2.58 (s, 3H).

MS (ESI) m/z: 325 (M+1)⁺.

EXAMPLE 87

Compound 97

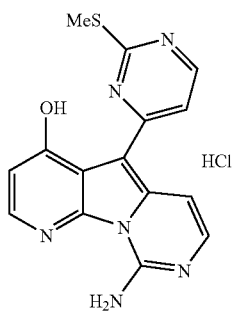

Compound 95 (45 mg, 0.14 mmol) was treated with a solution of HCl in 1.4-dioxane (3 mL, 3.8 M) for 15 min at 23° C. The reaction mixture was evaporated and washed with diethyl ether (2×) to give 97 as a yellow solid (36 mg, 71%).

¹H NMR (CDCl₃:CD₃OD 95:5, 300 MHz) δ 8.71 (d, J=5.9 Hz, 1H), 8.37 (d, J=4.9 Hz, 1H), 7.86 (d, J=6.1 Hz, 1H), 7.59 (d, J=7.3 Hz, 1H), 7.44 (d, J=7.3 Hz, 1H), 7.04 (d, J=5.9 Hz, 1H), 2.72 (s, 3H).

MS (ESI) m/z: 325 (M)⁺.

EXAMPLE 88

Compound 98

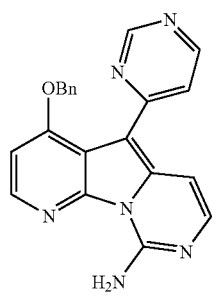

A mixture of 94 (65 mg, 0.157 mmol), Pd/C (6 mg, 10%) and TFA (28 µL, 0.36 mmol) in 1.2-dichloroethane (1 mL) in a Young tube was treated under Ar with Et₃SiH (220 µL, 1.4 mmol) at 100° C. for 72 h. The reaction mixture was treated with a saturated aqueous solution of sodium bicarbonate and extracted with CH₂Cl₂. The organic layer was dried over sodium sulphate, filtered, and evaporated. The residue was chromatographed (CH₂Cl₂:MeOH, 98:2) to give 98 as a pale yellow solid (13 mg, 23%).

¹H NMR (CDCl₃, 300 MHz) δ 9.14 (s, 1H), 8.27 (d, J=5.6 Hz, 1H), 8.22 (d, J=5.6 Hz, 1H), 7.67-7.63 (m, 2H), 7.54 (d, J=6.6 Hz, 1H), 7.38 (s, 5H), 6.97 (d, J=5.6 Hz, 1H), 5.28 (s, 2H).

MS (ESI) m/z: 369 (M+1)⁺.

EXAMPLE 89

Compound 100

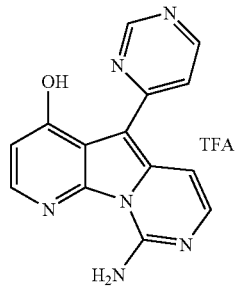

Compound 98 (11 mg, 0.030 mmol) was treated with TfOH (0.3 mL) at 23° C. for 1 h. The reaction mixture was cooled to 0° C. and treated with MeOH (2 mL) and aqueous NH₄OH 32% (2 mL). An orange solid was formed, filtered off, washed with H₂O, EtOH and diethyl ether, and treated with TFA to give 100 (9.0 mg, 76%).

¹H NMR (CD₃OD, 300 MHz) δ 9.30 (s, 1H), 8.88 (d, J=6.3 Hz, 1H), 8.40 (d, J=6.1 Hz, 1H), 8.34 (d, J=5.6 Hz, 1H), 7.72 (d, J=7.8 Hz, 1H), 7.49 (d, J=7.8 Hz, 1H), 7.04 (d, J=5.6 Hz, 1H).

MS (ESI) m/z: 279 (M)⁺.

EXAMPLE 90

Compound 101

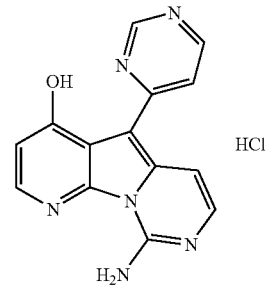

Compound 100 (35 mg, 0.13 mmol) was treated with HCl in 1.4-dioxane (4 mL, 3.8 M) at 0° C. for 10 min. The reaction mixture was evaporated, disolved in MeOH and evaporated to give 101 as a yellow solid (36 mg, 88%).

¹H NMR (300 MHz, CD₃OD) δ 9.35 (s, 1H), 8.92 (d, J=6.4 Hz, 1H), 8.44 (d, J=6.3 Hz, 1H), 8.38 (d, J=5.9 Hz, 1H), 7.79 (d, J=7.8 Hz, 1H), 7.54 (d, J=7.8 Hz, 1H), 7.08 (d, J=5.6 Hz, 1H).

MS (ESI) m/z: 279 (M)⁺.

EXAMPLE 91

Compound 99

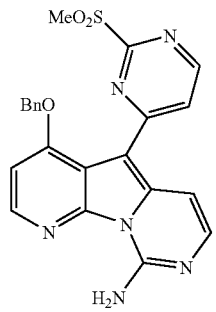

A solution of 94 (83 mg, 0.20 mmol) in CH$_2$Cl$_2$ (10 mL) was treated at 0° C. with a solution of mCPBA (112 mg, 0.5 mmol, 2.5 equiv, 77%) and warmed up to 23° C. for 3 h. The reaction mixture was quenched with a saturated aqueous solution of Na$_2$S$_2$O$_3$ and washed with a saturated aqueous solution of sodium bicarbonate (3×). The organic layer was dried over sodium sulphate, filtered, and evaporated. The residue was chromatographed (CH$_2$Cl$_2$:MeOH, 95:5) to give 99 as a yellow solid (25 mg, 28%).

$^1$H NMR (CDCl$_3$:CD$_3$OD 95:5, 300 MHz) δ 8.21 (d, J=5.6 Hz, 1H), 8.03 (d, J=5.4 Hz, 1H), 7.81 (d, J=5.6 Hz, 1H), 7.74 (d, J=6.6 Hz, 1H), 7.48 (d, J=6.8 Hz, 1H), 7.31 (s, 5H), 6.98 (d, J=5.6 Hz, 1H), 5.21 (s, 2H), 3.24 (s, 3H).

MS (ESI) m/z: 447 (M+1)$^+$.

EXAMPLE 92

Compound 102

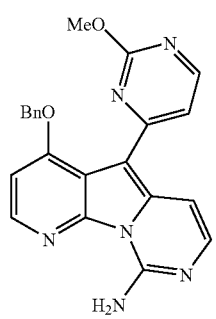

A suspension of 99 (10 mg, 0.022 mmol) was treated at 0° C. with a solution of MeONa in MeOH, previously prepared with Na (15 mg, 0.66 mmol) in 1 mL de MeOH. The reaction mixture was stirred at 23° C. for 5 h. Then was partitioned between CH$_2$Cl$_2$ and saturated aqueous solution of ammonium chloride. The organic layer was dried over sodium sulphate, filtered, and evaporated to give 102 as a yellow solid (5.6 mg, 64%).

$^1$H NMR (CDCl$_3$:CD$_3$OD 95:5, 300 MHz) δ 8.26 (d, J=5.6 Hz, 1H), 8.06 (d, J=5.4 Hz, 1H), 7.69 (d, J=6.6 Hz, 1H), 7.53 (d, J=6.6 Hz, 1H), 7.42-7.34 (m, 6H), 6.97 (d, J=5.6 Hz, 1H), 5.29 (s, 2H), 4.06 (s, 3H).

MS (ESI) m/z: 399 (M+1)$^+$.

EXAMPLE 93

Compound 103

A suspension of 99 (10 mg, 0.022 mmol) was treated at 0° C. with a solution of EtONa in EtOH, previously prepared with Na (15 mg, 0.66 mmol) in EtOH (1 mL), for 6 h. The reaction mixture was partitioned between chloroform and saturated aqueous solution of ammonium chloride. The organic layer was dried over sodium sulphate, filtered, and evaporated. The residue was chromatographed (CH$_2$Cl$_2$:MeOH, 95:5) to give 103 as a yellow solid (8 mg, 88%).

$^1$H NMR (CDCl$_3$:CD$_3$OD 95:5, 300 MHz) δ 8.19 (d, J=5.6 Hz, 1H), 7.90 (d, J=5.4 Hz, 1H), 7.48 (d, J=6.6 Hz, 1H), 7.34 (d, J=6.6 Hz, 1H), 7.27-7.24 (m, 6H), 6.92 (d, J=6.8 Hz, 1H), 5.20 (s, 2H), 4.36 (q, J=6.8 Hz, 2H), 1.35 (t, J=6.8 Hz, 3H).

MS (ESI) m/z: 413 (M+1)$^+$.

EXAMPLE 94

Compound 104

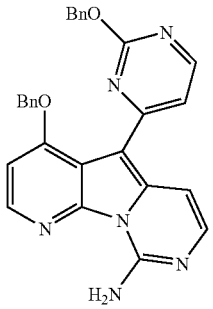

A suspension of NaH (18 mg, 0.44 mmol, 60%) in tetrahydrofuran (2 mL) was treated with benzyl alcohol (45 μL, 0.44 mmol). A solution of 99 (10 mg, 0.022 mmol) in dry tetrahydrofuran (3 mL) was added dropwise and stirred at 23° C. for 6 h. The reaction mixture was partitioned between chloroform and saturated aqueous solution of ammonium chloride. The organic layer was dried over sodium sulphate, filtered, and evaporated. The residue was chromatographed (from CH$_2$Cl$_2$ to CH$_2$Cl$_2$:MeOH 95:5) to give 104 as a yellow solid (9.0 mg, 86%).

$^1$H NMR (CDCl$_3$:CD$_3$OD 95:5, 300 MHz) δ 8.18 (d, J=5.6 Hz, 1H), 7.93 (d, J=5.4 Hz, 1H), 7.36 (d, J=7.8 Hz, 1H), 7.36-7.19 (m, 12H), 6.92 (d, J=5.9 Hz, 1H), 5.40 (s, 2H), 5.20 (s, 2H).

MS (ESI) m/z: 475 (M+1)$^+$.

EXAMPLE 95

Compound 105

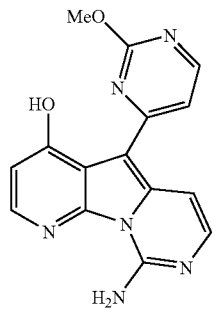

A solution of 102 (4.0 mg, 0.01 mmol) in triflic acid (0.2 mL) was stirred at 23° C. for 1 h. The reaction mixture was cooled at 0° C. and treated dropwise with MeOH (1 mL) and aqueous NH$_4$OH (32%) (1 mL). The reaction mixture was filtered, washed with H$_2$O, MeOH and diethyl ether and chromatographed (CH$_2$Cl$_2$:MeOH, 95:5) to give 105 as a yellow solid (1.8 mg, 58%).

$^1$H NMR (CDCl$_3$:CD$_3$OD 95:5, 300 MHz) δ 8.26 (d, J=5.6 Hz, 1H), 7.99 (d, J=5.4 Hz, 1H), 7.43 (d, J=6.8 Hz, 1H), 7.25 (d, J=5.6 Hz, 1H), 6.94 (d, J=6.8 Hz, 1H), 6.70 (d, J=5.4 Hz, 1H), 3.91 (s, 3H).

MS (ESI) m/z: 309 (M+1)$^+$.

EXAMPLE 96

Compound 106

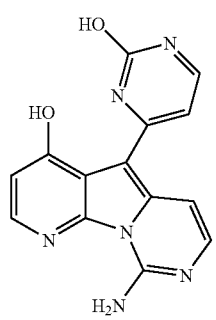

A solution of 104 (7 mg, 0.017 mmol) in triflic acid (0.2 mL) was stirred at 23° C. for 1.5 h. The reaction mixture was treated at 0° C. with MeOH (1 mL) and aqueous NH$_4$OH (32%) (1 mL), filtered and washed with H$_2$O, EtOH and diethyl ether to give 106 as an orange solid (6.6 mg, 95%).

$^1$H NMR (CD$_3$OD:CF$_3$CO$_2$D 95:5, 300 MHz) δ 8.35 (d, J=5.9 Hz, 1H), 8.20 (d, J=6.6 Hz, 1H), 7.60 (d, J=7.6 Hz, 1H), 7.43 (d, J=7.6 Hz, 1H), 7.18 (d, J=6.8 Hz, 1H), 7.03 (d, J=5.4 Hz, 1H).

MS (ESI) m/z: 295 (M+1)$^+$.

EXAMPLE 97

Compound 96

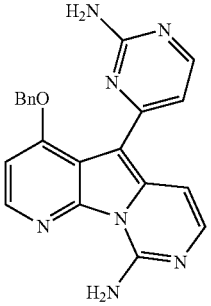

A solution of 52 (24 mg, 0.05 mmol) in CH$_2$Cl$_2$ (3 mL) was treated at −30° C. with a solution of mCPBA (30 mg, 0.14 mmol, 77%) in CH$_2$Cl$_2$. The reaction mixture was warmed up to 0° C. and stirred for 30 min. The reaction mixture was washed with a saturated aqueous solution of Na$_2$S$_2$O$_3$ and saturated aqueous solution of sodium bicarbonate. The organic layer was dried over sodium sulphate, filtered, and evaporated. The crude was dissolved in 1.4-dioxane (6 mL), treated with aqueous NH$_4$OH (32%) (10 mL) in a sealed tube and stirred at 100° C. for 16 h. The reaction mixture was evaporated and chromatographed (CH$_2$Cl$_2$:MeOH, from 98:2 to 95:5) to give 96 as a yellow solid (6 mg, 29%).

$^1$H NMR (CDCl$_3$:CD$_3$OD 9:1, 300 MHz) δ 8.18 (d, J=5.4 Hz, 1H), 7.78 (d, J=5.4 Hz, 1H), 7.30-7.25 (m, 7H), 6.90 (d, J=5.4 Hz, 2H), 5.19 (s, 2H).

MS (APCI) m/z: 384 (M+1)$^+$.

Rf: 0.64 (CH$_2$Cl$_2$:MeOH, 6:1).

EXAMPLE 98

Compound 107

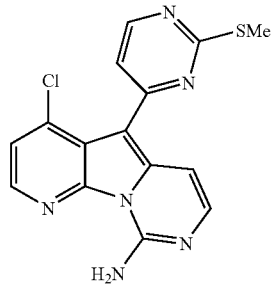

A solution of 84 (50 mg, 0.135 mmol) in a mixture of 1.4-dioxane:H$_2$O, (50:50, 8 mL) was stirred in a sealed tube at 100° C. for 16 h. The reaction mixture was evaporated and chromatographed (CH$_2$Cl$_2$:MeOH, 98:2) to give 107 as a yellow solid (40 mg, 86%).

$^1$H NMR (CDCl$_3$, 300 MHz) δ 8.54 (d, J=5.4 Hz, 1H), 8.27 (d, J=5.4 Hz, 1H), 7.59 (d, J=6.6 Hz, 1H), 7.46 (d, J=5.1 Hz, 1H), 7.26 (d, J=6.3 Hz, 1H), 7.23 (d, J=5.4 Hz, 1H), 2.64 (s, 3H).

$^{13}$C NMR (CDCl$_3$, 75 MHz) δ 172.0, 160.3, 156.1, 149.5, 144.0, 143.1, 139.9, 139.0, 135.0, 122.0, 119.9, 118.6, 101.4, 101.1, 14.3.

MS (ESI) m/z: 343 (M+1)$^+$.

EXAMPLE 99

Compound 108

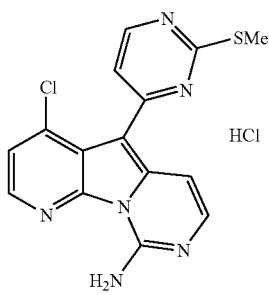

Compound 107 (25 mg, 0.073 mmol) was treated with anhydrous HCl (0.5 mL, 3.8 N in 1.4-dioxane) for 10 min at 23° C. The reaction mixture was evaporated, disolved in MeOH and evaporated to give 108 as a yellow solid (28 mg, 100%).

$^1$H NMR (CD$_3$OD, 300 MHz) δ 8.75 (d, J=5.6 Hz, 1H), 8.59 (d, J=5.4 Hz, 1H), 7.79 (d, J=5.1 Hz, 1H), 7.65 (d, J=5.6 Hz, 1H), 7.46 (d, J=7.8 Hz, 1H), 7.33 (d, J=7.8 Hz, 1H), 2.71 (s, 3H).

MS (ESI) m/z: 343 (M)$^+$.

EXAMPLE 100

Compound 109

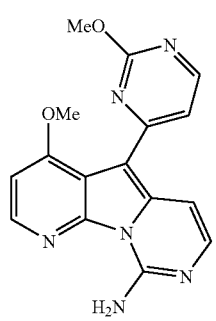

Compound 107 (10 mg, 0.029 mmol) was treated with MeONa in MeOH, freshly prepared from Na (30 mg, 1.3 mmol) and MeOH (4 mL), at 80° C. for 22 h. The reaction mixture was evaporated and partitioned between CH$_2$Cl$_2$ and saturated aqueous solution of ammonium chloride. The organic layer was dried over sodium sulphate, filtered, and evaporated. The residue was chromatographed (CH$_2$Cl$_2$: MeOH, 95:5) to give 109 (15 mg, 53%) as a yellow solid.

$^1$H NMR (CDCl$_3$, 300 MHz) δ 8.45 (d, J=5.4 Hz, 1H), 8.28 (d, J=5.4 Hz, 1H), 7.7 (d, J=6.6 Hz, 1H), 7.54 (d, J=6.6 Hz, 1H), 7.4 (d, J=5.4 Hz, 1H), 6.91 (d, J=5.7 Hz, 1H), 4.10 (s, 3H), 4.04 (s, 3H).

MS (ESI) m/z: 323 (M+1)$^+$.

EXAMPLE 101

Compounds 110 and 111

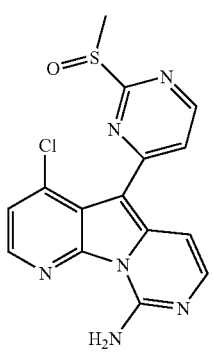

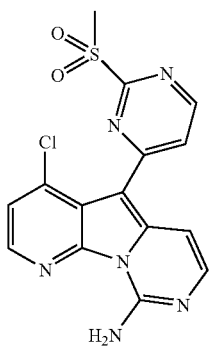

A solution of 107 (50 mg, 0.146 mmol) in CH$_2$Cl$_2$ (10 mL) was treated at −30° C. with a solution of mCPBA (82 mg, 77%, 0.37 mmol) in CH$_2$Cl$_2$ (1 mL). The reaction mixture was stirred at 23° C. for 2 h, treated with a saturated aqueous solution of Na$_2$S$_2$O$_3$ and partitioned between saturated aqueous solution of sodium bicarbonate and CH$_2$Cl$_2$. The organic layer was dried over sodium sulphate, filtered, and evaporated. The residue was chromatographed (CH$_2$Cl$_2$:MeOH, 95:5) to give 110 (23 mg, 44%) and 111 (29 mg, 53%) as yellow solids.

110:

$^1$H NMR (CDCl$_3$, 300 MHz) δ 8.84 (d, J=5.1 Hz, 1H), 8.30 (d, J=5.4 Hz, 1H), 7.68 (d, J=6.6 Hz, 1H), 7.63 (d, J=5.4 Hz, 1H), 7.50 (d, J=5.1 Hz, 1H), 7.46 (d, J=6.6 Hz, 1H), 3.04 (s, 3H).

MS (ESI) m/z: 381 (M+23)$^+$, 359 (M+1)$^+$.

111:

$^1$H NMR (CDCl$_3$, 300 MHz) δ 8.84 (d, J=5.4 Hz, 1H), 8.32 (d, J=5.1 Hz, 1H), 7.75 (d, J=5.4 Hz, 1H), 7.72 (d, J=6.6 Hz, 1H), 7.53 (d, J=6.6 Hz, 1H), 7.52 (d, J=5.4 Hz, 1H), 3.43 (s, 3H).

MS (ESI) m/z: 397 (M+23)$^+$, 375 (M+1)$^+$.

EXAMPLE 102

Compound 112

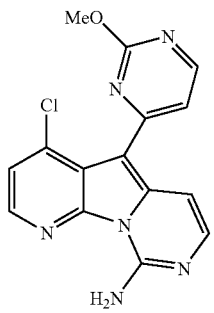

Compound 111 (29 mg, 0.077 mmol) was treated with methanolic MeONa in MeOH, freshly prepared from Na (30 mg, 1.3 mmol) and MeOH (4 mL), for 6 h at 23° C. The reaction mixture was evaporated and partitioned between $CH_2Cl_2$ and saturated aqueous solution of ammonium chloride. The organic layer was dried over sodium sulphate, filtered, and evaporated. The residue was chromatographed ($CH_2Cl_2$:MeOH, 95:5) to give 112 (17 mg, 68%) as a yellow solid.

$^1$H NMR (CDCl$_3$, 300 MHz) δ 8.54 (d, J=5.1 Hz, 1H), 8.27 (d, J=5.1 Hz, 1H), 7.58 (d, J=6.9 Hz, 1H), 7.47 (d, J=5.1 Hz, 1H), 7.29 (d, J=6.6 Hz, 1H), 7.21 (d, J=5.1 Hz, 1H), 4.10 (s, 3H).

MS (ESI) m/z: 327 (M+1)$^+$.

EXAMPLE 103

Compound 113

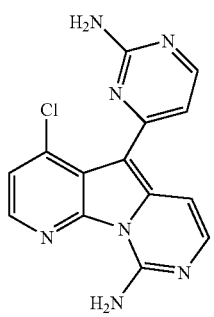

A solution of 84 (50 mg, 0.14 mmol) in $CH_2Cl_2$ (10 mL) was treated at −30° C. with a solution of mCPBA (76 mg, 0.34 mmol, 77%) in $CH_2Cl_2$ (2 mL). The reaction mixture was warmed up to 0° C. and stirred for 30 min. The reaction mixture was treated with a saturated aqueous solution of $Na_2S_2O_3$ and saturated aqueous solution of sodium bicarbonate. The organic layer was dried over sodium sulphate, filtered, and evaporated. The reaction crude was dissolved in 1.4-dioxane (4 mL) and treated with aqueous $NH_4OH$ (32%) (4 mL). The reaction mixture was poured in a sealed tube and stirred at 85° C. for 16 h. The reaction mixture was evaporated and chromatographed ($CH_2Cl_2$:MeOH, 95:5) to give 113 as a yellow solid (17 mg, 40%).

$^1$H NMR (CDCl$_3$:CD$_3$OD 9:1, 300 MHz) δ 8.17 (d, J=5.4 Hz, 2H), 7.36-7.34 (m, 2H), 6.98 (d, J=6.8 Hz, 1H), 6.78 (d, J=5.1 Hz, 1H).

$^{13}$C NMR (CDCl$_3$:CD$_3$OD 9:1, 75 MHz) δ 162.5, 161.6, 156.9, 149.6, 143.9, 141.8, 140.1, 138.1, 135.0, 121.9, 119.8, 114.0, 101.7, 100.7.

MS (ESI) m/z: 312 (M+1)$^+$.

EXAMPLE 104

Compound 83

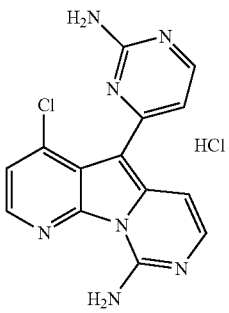

Compound 113 (12 mg, 0.038 mmol) was treated with anhydrous HCl in 1.4-dioxane (0.5 mL, 3.8 N) for 10 min at 23° C. The reaction mixture was evaporated, disolved in MeOH (1 mL) and evaporated to give 83 as a yellow solid (13.9 mg, 95%).

$^1$H NMR (CD$_3$OD, 300 MHz) δ 8.61 (d, J=5.1 Hz, 1H), 8.37 (d, J=6.6 Hz, 1H), 7.82 (d, J=5.1 Hz, 1H), 7.55 (s, 2H), 7.36 (d, J=6.6 Hz, 1H).

MS (ESI) m/z: 312 (M)$^+$.

EXAMPLE 105

Compound 115

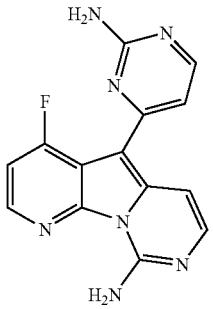

A mixture of 113 (5.0 mg, 0.016 mmol), 18-crown-6 (10 mg, 0.038 mmol) and dry KF (60 mg, 1.2 mmol) in DMSO (0.5 mL) was heated in a sealed tube for 16 h at 140° C. The reaction mixture was evaporated and chromatographed ($CH_2Cl_2$:MeOH 95:5) to give 115 as a yellow solid (3.5 mg, 74%).

$^1$H NMR (CDCl$_3$:CD$_3$OD 9:1, 300 MHz) δ 8.26 (dd, J=7.1, 5.4 Hz, 1H), 8.13 (d, J=5.4 Hz, 1H), 7.48 (d, J=6.6 Hz, 1H), 7.41 (d, J=6.6 Hz, 1H), 7.13 (d, J=11.0, 5.4 Hz, 1H), 6.94 (dd, J=5.4, 3.2 Hz, 1H). MS (ESI) m/z: 296 (M+1)$^+$.

EXAMPLE 106

Compound 114

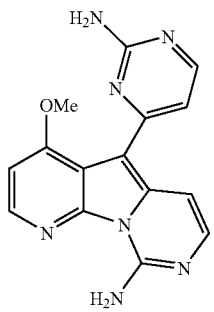

Compound 113 (10 mg, 0.032 mmol) was treated at 90° C. for 40 h with a solution of MeONa in MeOH:tetrahydrofuran 2:1 (6 mL) prepared by addition of Na (30 mg, 1.3 mmol) to MeOH. The reaction mixture was evaporated, disolved in CH$_2$Cl$_2$ and washed with a saturated aqueous solution of ammonium chloride. The organic layer was dried over sodium sulphate, filtered, and evaporated. The residue was chromatographed (CH$_2$Cl$_2$:MeOH 95:5) to give 114 as a yellow solid (4.0 mg, 41%).

$^1$H NMR (CDCl$_3$:CD$_3$OD 9:1, 300 MHz) δ 8.21 (d, J=5.4 Hz, 1H), 8.12 (d, J=5.6 Hz, 1H), 7.32 (s, 2H), 6.96 (d, J=5.9 Hz, 1H), 6.84 (d, J=5.6 Hz, 1H), 3.95 (s, 3H).

MS (ESI) m/z: 308 (M+1)$^+$.

EXAMPLE 107

Compound 116

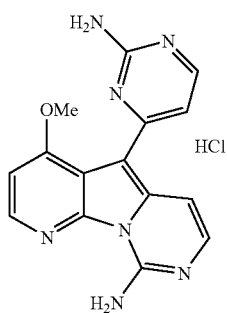

Compound 114 (1-7 mg, 0.006 mmol) was treated at 23° C. with HCl in 1.4-dioxane (0.5 mL, 5 N) for 20 min. The reaction mixture was evaporated, suspended in diethyl ether and evaporated to give 116 as a yellow solid (1.2 mg, 57%).

$^1$H NMR (300 MHz, CD$_3$OD) δ 8.57 (d, J=5.8 Hz, 1H), 8.26 (d, J=6.8 Hz, 1H), 7.94-7.90 (m, 2H), 7.68 (d, J=6.8 Hz, 1H), 7.49 (d, J=7.8 Hz, 1H), 7.36 (d, J=5.8 Hz, 1H), 4.16 (s, 3H).

Bioassays for Antitumor Screening

The finality of these assays is to interrupt the growth of a "in vitro" tumor cell culture by means a continued exhibition of the cells to the sample to be testing.

Cell Lines

| Name | N° ATCC | Species Tissue | Characteristics |
|---|---|---|---|
| P-388 | CCL-46 | mouse ascites fluid | lymphoid neoplasm |
| K-562 | CCL-243 | human leukemia | erythroleukemia (pleural effusion) |
| A-549 | CCL-185 | human lung | lung carcinoma "NSCL" |
| SK-MEL-28 | HTB-72 | human melanoma | malignant melanoma |
| HT-29 | HTB-38 | human colon | colon adenocarcinoma |
| LoVo | CCL-229 | human colon | colon adenocarcinoma |
| LoVo-Dox | | human colon | colon adenocarcinoma (MDR) |
| SW620 | CCL-228 | human colon | colon adenocarcinoma (lymph node metastasis) |
| DU-145 | HTB-81 | human prostate | prostate carcinoma, not androgen receptors |
| LNCaP | CRL-1740 | human prostate | prostate adenocarcinoma, with androgen receptors |
| SK-BR-3 | HTB-30 | human breast | breast adenocarcinoma, Her2/neu+, (pleural effusion) |
| MCF-7 | HTB-22 | human breast | breast adenocarcinoma, (pleural effusion) |
| MDA-MB-231 | HTB-26 | human breast | breast adenocarcinoma, Her2/neu+, (pleural effusion) |
| IGROV-1 | | human ovary | ovary adenocarcinoma |
| IGROV-ET | | human ovary | ovary adenocarcinoma, characterized as ET-743 resistant cells |
| SK-OV-3 | HTB-77 | human ovary | ovary adenocarcinoma (malignant ascites) |
| OVCAR-3 | HTB-161 | human ovary | ovary adenocarcinoma |
| HeLa | CCL-2 | human cervix | cervix epitheloid carcinoma |
| HeLa-APL | CCL-3 | human cervix | cervix epitheloid carcinoma, characterized as aplidine resistant cells |
| A-498 | HTB-44 | human kidney | kidney carcinoma |
| PANC-1 | CRL-1469 | human pancreas | pancreatic epitheloid carcinoma |
| HMEC1 | | human endothelium | |

1°.—Inhibition of Cell Growth by Counting Cells.

This form of the assay employs 24 well multidishes of 16 mm diameter (Bergeron, 1984; Schroeder, 1981). The tumor cell lines employed are: P-388 (ATCC CCL 46), suspension culture of a lymphoid neoplasm from a DBA/2 mouse; A-549 (ATCC CCL 185), monolayer culture of a human lung carcinoma; HT-29 (ATCC HTB-38), monolayer culture of a human colon carcinoma; MEL-28 (ATCC HTB-72), monolayer culture of a human melanoma and DU-145 (ATCC HTB-81), monolayer culture of a human prostate carcinoma.

Cells were maintained, in logarithmic phase of growth in Eagle's Minimum Essential Medium, with Earle's Balanced Salts, with non-essential amino acids, with 2.0 mM L-Glutamine, without sodium bicarbonate (EMEM/neaa), supplemented with 10% Fetal Calf Serum (FCS), 10$^{-2}$ M. sodium bicarbonate and 0.1 U/l penicillin G+0.1 g/l streptomycin sulphate. For the experiments, cells are harvested from subconfluent cultures using trypsin and resuspended in fresh medium before plating.

P-388 cells were seeded into 16 mm diameter wells at 1×10$^4$ cells per well in 1 ml aliquots of EMEM 5% FCS containing different concentrations of the sample to be tested. A separate set of cultures without drug was seeded as control of growth, to ensure that cells remained in exponential phase of growth. All determinations are carrying out in duplicate.

After three days of incubation at 37° C., 5% $CO_2$ in a 98% humid atmosphere, an approximately IC50 was determined by comparing the growth in wells with drug to the growth in wells control.

A-549, HT-29, MEL-28 and DU-145 cells were seeded into 16 mm diameter wells at $1 \times 10^4$ cells per well in 1 ml aliquots of EMEM 5% FCS containing different concentrations of the sample to be tested. A separate set of cultures without drug was seeded as control of growth, to ensure that cells remained in exponential phase of growth. All determinations are carrying out in duplicate. After three days of incubation at 37° C., 5% $CO_2$ in a 98% humid atmosphere cells were stained with 0.1% crystal violet. An approximately IC50 was determined by comparing the growth in wells with drug to the growth in wells control.

For quantifying the activity, after the incubation time, cells are trypsinized and counted in a Coulter Counter ZM. All counts (net cells per well), represent the average of duplicate wells. % G, percent of growth relative to cultures without drug. The results of these assays are used to generate dose-response curves from which more precise IC50 values are determined (sample concentration which produces 50% cell growth inhibition).

Obtained results may predict the usefulness of a certain drug as a potential cancer treatment. For this technique, compounds which show IC50 values smaller than 1 µg/ml are selected to continue with further studies. IC50's data allow to predict that not only could a drug be cystostatic, but also it could have a potential in terms of tumor reduction.

2°.—Inhibition of Cells Growth by Calorimetric Assay.

A calorimetric type of assay, using sulphorhodamine B (SRB) reaction has been adapted for a quantitative measurement of cell growth and viability [following the technique described by Philip Skehan, et al. (1990), New calorimetric cytotoxicity assay for anticancer drug screening, *J. Natl. Cancer Inst.*, 82:1107-1112]

This form of the assay employs 96 well cell culture microplates of 9 mm diameter (Faircloth, 1988; Mosmann, 1983). Most of the cell lines are obtained from American Type Culture Collection (ATCC) derived from different human cancer types.

Cells are maintained in RPMI 1640 10% FBS, supplemented with 0.1 g/l penicillin and 0.1 g/l streptomycin sulphate and then incubated at 37° C., 5% $CO_2$ and 98% humidity. For the experiments, cells were harvested from subconfluent cultures using trypsin and resuspended in fresh medium before plating.

Cells are seeded in 96 well microtiter plates, at $5 \times 10^3$ cells per well in aliquots of 195 µl medium, and they are allowed to attach to the plate surface by growing in drug free medium for 18 hours. Afterward, samples are added in aliquots of 5 µl in a ranging from 10 to $10^{-8}$ µg/ml, dissolved in DMSO/EtOH/PBS (0.5:0.5:99). After 48 hours exposure, the antitumor effect are measured by the SRB methodology: cells are fixed by adding 50 µl of cold 50% (wt/vol) trichloroacetic acid (TCA) and incubating for 60 minutes at 4° C. Plates are washed with deionized water and dried. One hundred µl of SRB solution (0.4% wt/vol in 1% acetic acid) is added to each microtiter well and incubated for 10 minutes at room temperature. Unbound SRB is removed by washing with 1% acetic acid. Plates are air dried and bound stain is solubilized with Tris buffer. Optical densities are read on a automated spectrophotometric plate reader at a single wavelength of 490 nm.

The values for mean±SD of data from triplicate wells are calculated. Some parameters for cellular responses can be calculated: GI=growth inhibition, TGI=total growth inhibition (cytostatic effect) and LC=cell killing (cytotoxic effect).

Obtained results may predict the usefulness of a certain drug as a potential cancer treatment. For this technique, compounds which show GI50 values smaller than 10 µg/ml are selected to continue with further studies. GI50's data allow to predict that not only could a drug be cystostatic, but also it could have a potential in terms of tumor reduction.

|  |  | 44 | 81 | 51 | 82 |
|---|---|---|---|---|---|
| DU-145 | GI50 | 4.75E−07 | 9.28E−07 | 6.54E−08 | 7.15E−07 |
|  | TGI | 1.51E−06 | 2.40E−06 | 1.48E−07 | 1.51E−06 |
|  | LC50 | 2.75E−05 | 3.04E−07 | 2.70E−06 | 2.92E−06 |
| LN-caP | GI50 | 3.51E−07 | 1.58E−07 | 7.37E−08 | 8.87E−07 |
|  | TGI | 7.85E−07 | 2.61E−07 | 1.27E−07 | 1.57E−06 |
|  | LC50 | 1.76E−06 | 2.77E−06 | 2.86E−07 | 2.28E−07 |
| SKOV-3 | GI50 | 2.75E−05 | 7.97E−07 | 1.46E−07 | 9.92E−07 |
|  | TGI | 2.75E−05 | 8.52E−06 | 2.15E−06 | 2.91E−06 |
|  | LC50 | 2.75E−05 | 3.45E−05 | 2.86E−05 | 2.92E−05 |
| IGROV | GI50 | 1.08E−06 | 2.10E−07 | 8.51E−08 | 9.71E−07 |
|  | TGI | 6.34E−06 | 2.70E−06 | 3.28E−07 | 1.76E−06 |
|  | LC50 | 2.46E−05 | 2.05E−05 | 2.12E−06 | 2.92E−05 |
| IGROV-ET | GI50 | 5.68E−07 | 8.55E−08 | 7.48E−08 | 8.90E−08 |
|  | TGI | 1.87E−06 | 2.28E−07 | 2.25E−07 | 2.32E−07 |
|  | LC50 | 1.72E−05 | 3.04E−05 | 1.86E−05 | 2.92E−05 |
| SK-BR-3 | GI50 | 6.12E−07 | 8.55E−08 | 5.91E−08 | 5.60E−07 |
|  | TGI | 1.61E−06 | 2.26E−06 | 1.42E−07 | 1.12E−06 |
|  | LC50 | 6.31E−06 | 9.49E−06 | 5.54E−07 | 2.26E−06 |
| MEL-28 | GI50 | 6.01E−07 | 3.13E−07 | 9.25E−08 | 3.65E−07 |
|  | TGI | 2.11E−06 | 7.36E−07 | 2.69E−07 | 7.93E−07 |
|  | LC50 | 8.95E−06 | 1.74E−06 | 1.37E−06 | 1.73E−06 |
| H-MEC-1 | GI50 | 1.58E−07 | 1.71E−07 | 1.64E−08 | 3.41E−07 |
|  | TGI | 3.07E−07 | 2.62E−07 | 1.54E−08 | 7.29E−07 |
|  | LC50 | 1.31E−06 | 8.58E−07 | 1.43E−07 | 1.55E−06 |
| A-549 | GI50 | 9.17E−06 | 3.04E−05 | 9.99E−08 | 2.92E−05 |
|  | TGI | 2.75E−05 | 3.04E−05 | 3.68E−07 | 2.92E−05 |
|  | LC50 | 2.75E−05 | 3.04E−05 | 4.57E−06 | 2.92E−05 |

-continued

| | | | | | |
|---|---|---|---|---|---|
| K-562 | GI50 | 4.17E−06 | 7.91E−08 | 3.11E−06 | 5.31E−07 |
| | TGI | 2.75E−05 | 3.29E−07 | 4.03E−07 | 7.32E−07 |
| | LC50 | 2.75E−05 | 5.23E−07 | 5.17E−06 | 1.01E−06 |
| PANC-1 | GI50 | 1.71E−06 | 1.00E−06 | 1.61E−07 | 1.03E−06 |
| | TGI | 9.94E−06 | 2.86E−06 | 2.73E−06 | 6.77E−06 |
| | LC50 | 2.75E−05 | 3.04E−05 | 2.86E−05 | 2.92E−05 |
| HT-29 | GI50 | 1.09E−06 | 1.30E−06 | 1.01E−07 | 7.12E−07 |
| | TGI | 1.09E−05 | 3.04E−05 | 2.86E−07 | 2.92E−06 |
| | LC50 | 2.75E−05 | 3.04E−05 | 2.86E−05 | 2.92E−05 |
| LOVO | GI50 | 4.56E−07 | 2.24E−07 | 7.74E−08 | 6.65E−07 |
| | TGI | 1.13E−06 | 1.77E−06 | 1.84E−07 | 2.15E−06 |
| | LC50 | 2.75E−05 | 3.04E−05 | 1.60E−05 | 2.92E−05 |
| LOVO-DOX | GI50 | 7.77E−07 | 7.06E−07 | 7.80E−08 | 7.00E−07 |
| | TGI | 3.27E−06 | 3.04E−06 | 2.86E−07 | 2.72E−06 |
| | LC50 | 2.35E−05 | 3.04E−05 | 1.79E−05 | 1.21E−05 |
| HELA | GI50 | — | — | — | — |
| | TGI | — | — | — | — |
| | LC50 | — | — | — | — |
| HELA-APL | GI50 | — | — | — | — |
| | TGI | — | — | — | — |
| | LC50 | — | — | — | — |

| | | 64 | 80 | 71 | 113 |
|---|---|---|---|---|---|
| DU-145 | GI50 | 3.10E−05 | 1.81E−06 | 7.50E−07 | 1.51E−06 |
| | TGI | 3.28E−05 | 8.70E−06 | 2.31E−06 | 6.26E−06 |
| | LC50 | 3.28E−05 | 3.59E−05 | 3.35E−05 | 3.21E−05 |
| LN-caP | GI50 | 2.84E−06 | 9.70E−07 | 5.02E−08 | 1.57E−06 |
| | TGI | 7.89E−06 | 1.65E−06 | 2.15E−07 | 2.39E−06 |
| | LC50 | 1.99E−05 | 2.79E−06 | 1.82E−06 | 1.56E−05 |
| SKOV-3 | GI50 | 2.23E−05 | 1.25E−05 | 1.06E−06 | 1.37E−06 |
| | TGI | 3.28E−05 | 3.45E−05 | 3.00E−06 | 5.39E−06 |
| | LC50 | 3.28E−05 | 3.59E−05 | 3.35E−05 | 3.21E−05 |
| IGROV | GI50 | 1.44E−05 | 1.55E−06 | 7.97E−07 | 2.94E−06 |
| | TGI | 3.28E−05 | 3.26E−06 | 1.65E−06 | 8.53E−06 |
| | LC50 | 3.28E−05 | 2.48E−05 | 4.15E−06 | 2.41E−05 |
| IGROV-ET | GI50 | 1.89E−05 | 2.48E−06 | 1.04E−06 | 1.30E−06 |
| | TGI | 3.28E−05 | 9.45E−06 | 2.75E−06 | 6.00E−06 |
| | LC50 | 3.28E−05 | 3.59E−05 | 3.19E−05 | 3.21E−05 |
| SK-BR-3 | GI50 | — | — | — | — |
| | TGI | — | — | — | — |
| | LC50 | — | — | — | — |
| MEL-28 | GI50 | 2.17E−05 | 2.42E−06 | 5.56E−07 | 2.12E−06 |
| | TGI | 3.28E−05 | 7.08E−06 | 1.18E−06 | 6.29E−06 |
| | LC50 | 3.28E−05 | 1.97E−05 | 2.50E−06 | 1.76E−05 |
| H-MEC-1 | GI50 | — | — | — | — |
| | TGI | — | — | — | — |
| | LC50 | — | — | — | — |
| A-549 | GI50 | 3.16E−05 | 7.73E−06 | 1.10E−06 | 4.30E−06 |
| | TGI | 3.28E−05 | 1.59E−05 | 2.70E−06 | 9.59E−06 |
| | LC50 | 3.28E−05 | 3.27E−05 | 1.12E−05 | 2.14E−05 |
| K-562 | GI50 | 9.24E−06 | 9.88E−06 | 1.70E−06 | 6.16E−06 |
| | TGI | 2.47E−05 | 3.59E−05 | 1.30E−05 | 2.00E−05 |
| | LC50 | 3.28E−05 | 3.59E−05 | 3.35E−05 | 3.21E−05 |
| PANC-1 | GI50 | 2.09E−05 | 8.41E−06 | 1.07E−06 | 1.11E−06 |
| | TGI | 3.28E−05 | 2.42E−05 | 3.78E−06 | 2.76E−05 |
| | LC50 | 3.28E−05 | 3.59E−05 | 3.35E−05 | 3.21E−05 |
| HT-29 | GI50 | 3.28E−05 | 2.45E−06 | 1.10E−06 | 4.72E−06 |
| | TGI | 3.28E−05 | 3.59E−05 | 3.35E−06 | 3.21E−05 |
| | LC50 | 3.28E−05 | 3.59E−05 | 3.35E−05 | 3.21E−05 |
| LOVO | GI50 | 2.33E−05 | 4.06E−06 | 3.18E−07 | 1.26E−06 |
| | TGI | 3.28E−05 | 1.48E−05 | 1.84E−06 | 7.83E−06 |
| | LC50 | 3.28E−05 | 3.59E−05 | 3.35E−05 | 3.21E−05 |
| LOVO-DOX | GI50 | 2.27E−05 | 4.20E−06 | 4.65E−07 | 2.35E−06 |
| | TGI | 3.28E−05 | 2.01E−05 | 1.79E−06 | 1.18E−05 |
| | LC50 | 3.28E−05 | 3.59E−05 | 3.35E−05 | 3.21E−05 |
| HELA | GI50 | — | — | — | — |
| | TGI | — | — | — | — |
| | LC50 | — | — | — | — |
| HELA-APL | GI50 | — | — | — | — |
| | TGI | — | — | — | — |
| | LC50 | — | — | — | — |

| | | 107 | 106 | 98 |
|---|---|---|---|---|
| DU-145 | GI50 | 6.53E−07 | 1.62E−05 | 5.94E−06 |
| | TGI | 1.44E−05 | 2.45E−05 | 1.41E−05 |
| | LC50 | 2.92E−05 | 2.45E−05 | 2.71E−05 |

-continued

|  |  |  |  |  |
|---|---|---|---|---|
| LN-caP | GI50 | 3.38E−06 | 6.42E−06 | 1.85E−06 |
|  | TGI | 9.25E−06 | 1.64E−05 | 6.49E−06 |
|  | LC50 | 2.53E−05 | 2.45E−05 | 2.39E−05 |
| SKOV-3 | GI50 | 1.95E−07 | 5.73E−06 | 1.06E−05 |
|  | TGI | 3.35E−06 | 1.51E−05 | 2.19E−05 |
|  | LC50 | 2.92E−05 | 2.45E−05 | 2.71E−05 |
| IGROV | GI50 | 2.95E−06 | 6.69E−06 | 8.96E−06 |
|  | TGI | 8.34E−06 | 1.27E−05 | 1.55E−05 |
|  | LC50 | 2.37E−05 | 2.41E−05 | 2.68E−05 |
| IGROV-ET | GI50 | 1.57E−06 | 4.97E−06 | 7.22E−06 |
|  | TGI | 1.44E−05 | 1.10E−05 | 1.21E−05 |
|  | LC50 | 2.92E−05 | 2.44E−05 | 2.01E−05 |
| SK-BR-3 | GI50 | — | — | — |
|  | TGI | — | — | — |
|  | LC50 | — | — | — |
| MEL-28 | GI50 | 2.48E−08 | 8.87E−06 | 7.52E−06 |
|  | TGI | 5.19E−06 | 2.45E−05 | 1.26E−05 |
|  | LC50 | 2.92E−05 | 2.45E−05 | 2.12E−05 |
| H-MEC-1 | GI50 | — | — | — |
|  | TGI | — | — | — |
|  | LC50 | — | — | — |
| A-549 | GI50 | 4.52E−06 | 1.82E−05 | 1.53E−05 |
|  | TGI | 2.70E−05 | 2.45E−05 | 2.71E−05 |
|  | LC50 | 2.92E−05 | 2.45E−05 | 2.71E−05 |
| K-562 | GI50 | 2.18E−06 | 1.06E−05 | 7.82E−06 |
|  | TGI | 9.19E−06 | 2.45E−05 | 1.42E−05 |
|  | LC50 | 2.92E−05 | 2.45E−05 | 2.58E−05 |
| PANC-1 | GI50 | 4.99E−06 | 6.44E−06 | 5.62E−06 |
|  | TGI | 2.92E−05 | 1.71E−05 | 1.03E−05 |
|  | LC50 | 2.92E−05 | 2.45E−05 | 1.90E−05 |
| HT-29 | GI50 | 1.11E−06 | 2.45E−05 | 1.56E−05 |
|  | TGI | 2.92E−05 | 2.45E−05 | 2.71E−05 |
|  | LC50 | 2.92E−05 | 2.45E−05 | 2.71E−05 |
| LOVO | GI50 | 1.73E−07 | 2.45E−05 | 5.02E−06 |
|  | TGI | 3.79E−06 | 2.45E−05 | 1.51E−05 |
|  | LC50 | 2.92E−05 | 2.45E−05 | 2.71E−05 |
| LOVO-DOX | GI50 | 1.27E−07 | 8.18E−06 | 5.92E−06 |
|  | TGI | 5.98E−07 | 2.45E−05 | 1.42E−05 |
|  | LC50 | 2.30E−05 | 2.45E−05 | 2.71E−05 |
| HELA | GI50 | — | — | — |
|  | TGI | — | — | — |
|  | LC50 | — | — | — |
| HELA-APL | GI50 | — | — | — |
|  | TGI | — | — | — |
|  | LC50 | — | — | — |

|  |  | 66 | 61 | 100 | 55 | 105 |
|---|---|---|---|---|---|---|
| DU-145 | GI50 | 1.00E−05 | 1.49E−05 | 7.39E−07 | 1.14E−05 | 1.42E−05 |
|  | TGI | 2.59E−05 | 3.89E−05 | 5.25E−06 | 3.38E−05 | 3.24E−05 |
|  | LC50 | 4.42E−05 | 3.89E−05 | 2.55E−05 | 3.42E−05 | 3.24E−05 |
| LN-caP | GI50 | 1.25E−05 | 8.70E−06 | 1.05E−06 | 6.84E−06 | 5.48E−06 |
|  | TGI | 2.55E−05 | 1.80E−05 | 3.29E−06 | 1.55E−05 | 1.75E−05 |
|  | LC50 | 4.42E−05 | 3.71E−05 | 1.09E−05 | 3.42E−05 | 3.24E−05 |
| SKOV-3 | GI50 | 1.57E−05 | 1.24E−05 | 1.74E−06 | 7.73E−06 | 8.14E−06 |
|  | TGI | 3.04E−05 | 2.96E−05 | 9.84E−06 | 2.09E−05 | 2.91E−05 |
|  | LC50 | 4.42E−05 | 3.89E−05 | 2.55E−05 | 3.42E−05 | 3.24E−05 |
| IGROV | GI50 | 9.99E−06 | 1.57E−05 | 1.40E−06 | 7.42E−06 | 6.26E−06 |
|  | TGI | 1.74E−05 | 3.49E−05 | 4.69E−06 | 1.53E−05 | 1.31E−05 |
|  | LC50 | 3.04E−05 | 3.89E−05 | 1.32E−05 | 3.42E−05 | 2.75E−05 |
| IGROV-ET | GI50 | 9.81E−06 | 7.34E−06 | 6.83E−07 | 8.79E−06 | 8.17E−06 |
|  | TGI | 1.98E−05 | 2.27E−05 | 2.33E−06 | 2.00E−05 | 2.23E−05 |
|  | LC50 | 3.98E−05 | 3.89E−05 | 2.29E−05 | 3.42E−05 | 3.24E−05 |
| SK-BR-3 | GI50 | — | — | 4.64E−07 | 8.82E−06 | 2.42E−06 |
|  | TGI | — | — | 1.52E−06 | 2.32E−05 | 1.26E−05 |
|  | LC50 | — | — | 1.06E−05 | 3.42E−05 | 3.24E−05 |
| MEL-28 | GI50 | 8.84E−06 | 2.02E−05 | 1.32E−06 | 1.16E−05 | 1.38E−05 |
|  | TGI | 1.87E−05 | 3.89E−05 | 8.08E−06 | 3.20E−05 | 3.24E−05 |
|  | LC50 | 3.96E−05 | 3.89E−05 | 2.55E−05 | 3.42E−05 | 3.24E−05 |
| H-MEC-1 | GI50 | — | — | — | — | — |
|  | TGI | — | — | — | — | — |
|  | LC50 | — | — | — | — | — |
| A-549 | GI50 | 1.61E−05 | 2.46E−05 | 6.78E−07 | 7.29E−06 | 7.49E−06 |
|  | TGI | 4.42E−05 | 3.89E−05 | 2.63E−06 | 1.90E−05 | 3.24E−05 |
|  | LC50 | 4.42E−05 | 3.89E−05 | 2.55E−05 | 3.42E−05 | 3.24E−05 |
| K-562 | GI50 | 2.16E−05 | 9.79E−06 | 6.78E−06 | 9.71E−06 | 1.28E−05 |
|  | TGI | 4.42E−05 | 2.44E−05 | 1.49E−05 | 1.83E−05 | 2.93E−05 |
|  | LC50 | 4.42E−05 | 3.89E−05 | 2.55E−05 | 3.42E−05 | 3.24E−05 |

-continued

|  |  |  |  |  |  |  |
|---|---|---|---|---|---|---|
| PANC-1 | GI50 | 8.00E−06 | 1.15E−05 | 4.92E−06 | 8.79E−06 | 1.18E−05 |
|  | TGI | 2.16E−05 | 3.83E−05 | 2.55E−05 | 2.91E−05 | 3.24E−05 |
|  | LC50 | 4.42E−05 | 3.89E−05 | 2.55E−05 | 3.42E−05 | 3.24E−05 |
| HT-29 | GI50 | 1.79E−05 | 2.89E−05 | 1.49E−05 | 1.32E−05 | 3.24E−05 |
|  | TGI | 4.42E−05 | 3.89E−05 | 2.55E−05 | 3.42E−05 | 3.24E−05 |
|  | LC50 | 4.42E−05 | 3.89E−05 | 2.55E−05 | 3.42E−05 | 3.24E−05 |
| LOVO | GI50 | 1.71E−05 | 2.30E−05 | 8.77E−07 | 9.92E−06 | 1.43E−05 |
|  | TGI | 4.42E−05 | 3.89E−05 | 5.12E−06 | 3.42E−05 | 3.24E−05 |
|  | LC50 | 4.42E−05 | 3.89E−05 | 2.55E−05 | 3.42E−05 | 3.24E−05 |
| LOVO-DOX | GI50 | 2.22E−06 | 1.37E−05 | 1.18E−06 | 3.93E−06 | 2.19E−05 |
|  | TGI | 4.42E−05 | 3.89E−05 | 1.30E−05 | 1.02E−05 | 3.24E−05 |
|  | LC50 | 4.42E−05 | 3.89E−05 | 2.55E−05 | 2.64E−05 | 3.24E−05 |
| HELA | GI50 | — | — | — | — | — |
|  | TGI | — | — | — | — | — |
|  | LC50 | — | — | — | — | — |
| HELA-APL | GI50 | — | — | — | — | — |
|  | TGI | — | — | — | — | — |
|  | LC50 | — | — | — | — | — |

|  |  | 19b | 49 | 50 | 110 | 111 |
|---|---|---|---|---|---|---|
| DU-145 | GI50 | 5.79E−06 | 5.33E−06 | 1.65E−05 | 2.03E−06 | 1.94E−06 |
|  | TGI | 2.39E−05 | 1.38E−05 | 3.03E−05 | 8.97E−06 | 6.40E−06 |
|  | LC50 | 2.80E−05 | 3.21E−05 | 3.03E−05 | 2.79E−05 | 1.68E−05 |
| LN-caP | GI50 | 2.36E−06 | 1.26E−06 | 8.86E−07 | 1.45E−06 | 4.30E−06 |
|  | TGI | 8.59E−06 | 4.30E−06 | 1.88E−06 | 4.71E−06 | 9.26E−06 |
|  | LC50 | 2.76E−05 | 1.95E−05 | 3.03E−05 | 1.67E−05 | 1.99E−05 |
| SKOV-3 | GI50 | 8.28E−06 | 5.42E−06 | 1.58E−05 | 1.19E−05 | 2.05E−06 |
|  | TGI | 1.89E−05 | 1.50E−05 | 3.03E−05 | 2.79E−05 | 6.88E−06 |
|  | LC50 | 2.80E−05 | 3.21E−05 | 3.03E−05 | 2.79E−05 | 2.18E−05 |
| IGROV | GI50 | 4.11E−06 | 4.68E−06 | 2.03E−05 | 1.43E−05 | 3.55E−06 |
|  | TGI | 8.93E−06 | 1.17E−05 | 3.03E−05 | 2.79E−05 | 9.60E−06 |
|  | LC50 | 1.94E−05 | 2.93E−05 | 3.03E−05 | 2.79E−05 | 2.59E−05 |
| IGROV-ET | GI50 | 3.27E−06 | 4.23E−06 | 1.29E−05 | 1.09E−05 | 3.87E−06 |
|  | TGI | 8.17E−06 | 1.20E−05 | 3.03E−05 | 2.79E−05 | 1.10E−05 |
|  | LC50 | 2.04E−05 | 3.21E−05 | 3.03E−05 | 2.79E−05 | 2.67E−05 |
| SK-BR-3 | GI50 | 1.89E−06 | 7.19E−06 | 1.16E−05 | 9.20E−07 | 4.35E−06 |
|  | TGI | 8.23E−06 | 1.86E−05 | 3.03E−05 | 1.98E−06 | 9.69E−06 |
|  | LC50 | 2.80E−05 | 3.21E−05 | 3.03E−05 | 1.16E−05 | 2.13E−05 |
| MEL-28 | GI50 | 4.92E−06 | 6.35E−06 | 3.03E−05 | 5.55E−06 | 1.25E−06 |
|  | TGI | 1.65E−05 | 1.43E−05 | 3.03E−05 | 2.79E−05 | 5.15E−06 |
|  | LC50 | 2.80E−05 | 3.21E−05 | 3.03E−05 | 2.79E−05 | 1.57E−05 |
| H-MEC-1 | GI50 | — | 4.56E−07 | 8.01E−06 | 1.70E−06 | 1.08E−09 |
|  | TGI | — | 4.59E−06 | 2.44E−05 | 1.08E−05 | 1.53E−08 |
|  | LC50 | — | 8.73E−06 | 3.03E−05 | 2.79E−05 | 6.03E−07 |
| A-549 | GI50 | 4.53E−07 | 2.11E−06 | 5.25E−06 | 1.10E−05 | 4.35E−06 |
|  | TGI | 2.80E−05 | 9.21E−06 | 3.03E−05 | 2.79E−05 | 1.30E−05 |
|  | LC50 | 2.80E−05 | 3.21E−05 | 3.03E−05 | 2.79E−05 | 2.67E−05 |
| K-562 | GI50 | 8.48E−06 | 1.39E−05 | 3.03E−05 | 9.92E−06 | 7.26E−06 |
|  | TGI | 1.59E−05 | 2.77E−05 | 3.03E−05 | 2.79E−05 | 1.59E−05 |
|  | LC50 | 2.80E−05 | 3.21E−05 | 3.03E−05 | 2.79E−05 | 2.67E−05 |
| PANC-1 | GI50 | 8.87E−06 | 1.07E−05 | 3.03E−05 | 1.45E−05 | 3.07E−06 |
|  | TGI | 2.80E−05 | 3.21E−05 | 3.03E−05 | 2.79E−05 | 8.70E−06 |
|  | LC50 | 2.80E−05 | 3.21E−05 | 3.03E−05 | 2.79E−05 | 2.46E−05 |
| HT-29 | GI50 | 1.52E−05 | 1.20E−05 | 3.03E−05 | 4.15E−06 | 5.34E−06 |
|  | TGI | 2.80E−05 | 3.21E−05 | 3.03E−05 | 2.79E−05 | 1.66E−05 |
|  | LC50 | 2.80E−05 | 3.21E−05 | 3.03E−05 | 2.79E−05 | 2.67E−05 |
| LOVO | GI50 | 3.25E−06 | 2.37E−06 | 1.20E−05 | 1.38E−06 | 1.54E−06 |
|  | TGI | 1.97E−05 | 1.16E−05 | 3.03E−05 | 6.21E−06 | 6.99E−06 |
|  | LC50 | 2.80E−05 | 3.21E−05 | 3.03E−05 | 2.79E−05 | 2.67E−05 |
| LOVO-DOX | GI50 | 7.42E−06 | 2.11E−06 | 1.26E−05 | 2.04E−06 | 1.51E−06 |
|  | TGI | 2.10E−05 | 7.86E−06 | 3.03E−05 | 1.21E−05 | 7.07E−06 |
|  | LC50 | 2.80E−05 | 2.76E−05 | 3.03E−05 | 2.79E−05 | 2.67E−05 |
| HELA | GI50 | — | — | — | — | — |
|  | TGI | — | — | — | — | — |
|  | LC50 | — | — | — | — | — |
| HELA-APL | GI50 | — | — | — | — | — |
|  | TGI | — | — | — | — | — |
|  | LC50 | — | — | — | — | — |

|  |  | 1 | 109 | 112 | 86 | 87 |
|---|---|---|---|---|---|---|
| DU-145 | GI50 | 8.93E−07 | 1.63E−06 | 7.16E−07 | 1.73E−05 | 1.83E−05 |
|  | TGI | 2.10E−06 | 3.10E−05 | 1.72E−06 | 1.73E−05 | 1.73E−05 |
|  | LC50 | 1.99E−05 | 3.10E−05 | 3.06E−06 | 1.73E−05 | 1.73E−05 |
| LN-caP | GI50 | 5.39E−08 | 1.40E−06 | 8.72E−07 | 1.73E−05 | 1.73E−05 |
|  | TGI | 2.10E−06 | 4.81E−06 | 1.51E−06 | 1.73E−05 | 1.73E−05 |
|  | LC50 | 1.41E−06 | 3.10E−05 | 2.62E−06 | 1.73E−05 | 1.73E−05 |

-continued

|  |  |  |  |  |  |  |
|---|---|---|---|---|---|---|
| SKOV-3 | GI50 | 1.21E−06 | — | 9.89E−07 | 1.73E−05 | 1.73E−05 |
|  | TGI | 3.32E−06 | — | 2.30E−06 | 1.73E−05 | 1.73E−05 |
|  | LC50 | 3.41E−05 | — | 3.06E−05 | 1.73E−05 | 1.73E−05 |
| IGROV | GI50 | 1.14E−06 | 3.07E−06 | 1.65E−06 | 1.73E−05 | 1.73E−05 |
|  | TGI | 2.90E−06 | 1.46E−05 | 7.59E−06 | 1.73E−05 | 1.73E−05 |
|  | LC50 | 3.41E−05 | 3.10E−05 | 3.06E−05 | 1.73E−05 | 1.73E−05 |
| IGROV-ET | GI50 | 1.28E−06 | 7.17E−06 | 7.65E−06 | 1.73E−05 | 1.73E−05 |
|  | TGI | 2.82E−06 | 2.21E−05 | 1.91E−05 | 1.73E−05 | 1.73E−05 |
|  | LC50 | 3.41E−05 | 3.10E−05 | 3.06E−05 | 1.73E−05 | 1.73E−05 |
| SK-BR-3 | GI50 | 8.48E−07 | 1.47E−06 | 2.01E−06 | 1.73E−05 | 1.73E−05 |
|  | TGI | 2.31E−06 | 5.40E−06 | 7.13E−06 | 1.73E−05 | 1.73E−05 |
|  | LC50 | 2.77E−05 | 3.10E−05 | 2.78E−05 | 1.73E−05 | 1.73E−05 |
| MEL-28 | GI50 | 1.20E−06 | 1.26E−06 | 3.21E−07 | 1.73E−05 | 1.73E−05 |
|  | TGI | 2.13E−06 | 6.64E−06 | 5.29E−06 | 1.73E−05 | 1.73E−05 |
|  | LC50 | 2.80E−06 | 2.24E−05 | 1.66E−05 | 1.73E−05 | 1.73E−05 |
| H-MEC-1 | GI50 | 2.73E−07 | 2.04E−06 | 1.27E−06 | 7.99E−06 | 7.30E−06 |
|  | TGI | 7.50E−07 | 2.17E−05 | 4.71E−06 | 1.73E−05 | 1.73E−05 |
|  | LC50 | 6.07E−06 | 3.10E−05 | 1.19E−05 | 1.73E−05 | 1.73E−05 |
| A-549 | GI50 | 9.85E−07 | 5.49E−06 | 1.38E−06 | 1.73E−05 | 1.73E−05 |
|  | TGI | 2.21E−06 | 2.33E−05 | 4.35E−06 | 1.73E−05 | 1.73E−05 |
|  | LC50 | 3.41E−05 | 3.10E−05 | 3.06E−05 | 1.73E−05 | 1.73E−05 |
| K-562 | GI50 | 1.55E−06 | 7.60E−06 | 1.40E−06 | 1.73E−05 | 1.73E−05 |
|  | TGI | 3.92E−06 | 2.41E−05 | 8.66E−06 | 1.73E−05 | 1.73E−05 |
|  | LC50 | 3.41E−05 | 3.10E−05 | 3.06E−05 | 1.73E−05 | 1.73E−05 |
| PANC-1 | GI50 | 1.68E−06 | 9.40E−06 | 6.34E−06 | 1.73E−05 | 1.73E−05 |
|  | TGI | 1.51E−05 | 3.10E−05 | 3.06E−05 | 1.73E−05 | 1.73E−05 |
|  | LC50 | 3.41E−05 | 3.10E−05 | 3.06E−05 | 1.73E−05 | 1.73E−05 |
| HT-29 | GI50 | 2.85E−06 | 1.16E−06 | 1.16E−06 | 1.73E−05 | 1.73E−05 |
|  | TGI | 3.41E−05 | 3.10E−05 | 3.06E−05 | 1.73E−05 | 1.73E−05 |
|  | LC50 | 3.41E−05 | 3.10E−05 | 3.06E−05 | 1.73E−05 | 1.73E−05 |
| LOVO | GI50 | 8.01E−07 | 1.27E−06 | 7.65E−07 | 1.73E−05 | 1.73E−05 |
|  | TGI | 1.69E−06 | 7.04E−06 | 1.96E−06 | 1.73E−05 | 1.73E−05 |
|  | LC50 | 3.41E−05 | 3.10E−05 | 3.06E−05 | 1.73E−05 | 1.73E−05 |
| LOVO-DOX | GI50 | 1.02E−06 | 2.59E−06 | 6.00E−07 | 1.73E−05 | 1.73E−05 |
|  | TGI | 2.23E−06 | 1.74E−05 | 1.48E−06 | 1.73E−05 | 1.73E−05 |
|  | LC50 | 3.41E−05 | 3.10E−05 | 3.06E−06 | 1.73E−05 | 1.73E−05 |
| HELA | GI50 | — | — | — | — | — |
|  | TGI | — | — | — | — | — |
|  | LC50 | — | — | — | — | — |
| HELA-APL | GI50 | — | — | — | — | — |
|  | TGI | — | — | — | — | — |
|  | LC50 | — | — | — | — | — |

|  |  | 88 | 114 | 115 | 56 | 42 |
|---|---|---|---|---|---|---|
| DU-145 | GI50 | 9.02E−07 | 7.32E−07 | 7.59E−07 | 2.12E−06 | 1.48E−06 |
|  | TGI | 1.87E−05 | 1.75E−06 | 1.79E−06 | 8.88E−06 | 6.10E−06 |
|  | LC50 | 1.87E−05 | 6.22E−06 | 1.07E−05 | 2.56E−05 | 2.11E−05 |
| LN-caP | GI50 | 4.15E−07 | 6.25E−07 | 7.21E−07 | 5.93E−06 | 4.32E−07 |
|  | TGI | 8.13E−07 | 1.21E−06 | 1.30E−06 | 1.11E−05 | 1.25E−06 |
|  | LC50 | 1.59E−06 | 2.35E−06 | 2.34E−06 | 2.06E−05 | 5.97E−06 |
| SKOV-3 | GI50 | — | — | — | 7.12E−06 | 1.08E−06 |
|  | TGI | — | — | — | 1.59E−05 | 5.32E−06 |
|  | LC50 | — | — | — | 3.55E−05 | 2.15E−05 |
| IGROV | GI50 | 3.23E−06 | 8.43E−07 | 1.23E−06 | 8.69E−06 | 1.56E−06 |
|  | TGI | 9.58E−06 | 1.81E−06 | 5.22E−06 | 1.91E−05 | 5.15E−06 |
|  | LC50 | 1.87E−05 | 1.58E−05 | 3.39E−05 | 3.83E−05 | 1.30E−05 |
| IGROV-ET | GI50 | 1.40E−06 | 1.51E−06 | 1.47E−06 | 1.15E−06 | 1.70E−06 |
|  | TGI | 6.74E−06 | 3.29E−06 | 6.84E−06 | 2.35E−05 | 5.45E−06 |
|  | LC50 | 1.87E−05 | 2.54E−05 | 3.39E−05 | 3.83E−05 | 1.54E−05 |
| SK-BR-3 | GI50 | 5.62E−07 | — | 7.52E−07 | 5.32E−06 | 6.77E−08 |
|  | TGI | 1.36E−06 | — | 1.69E−06 | 1.88E−05 | 3.22E−07 |
|  | LC50 | 1.87E−05 | — | 6.23E−06 | 3.83E−05 | 1.67E−06 |
| MEL-28 | GI50 | 1.43E−06 | 6.05E−07 | 1.12E−06 | 7.73E−06 | 2.56E−06 |
|  | TGI | 4.17E−06 | 1.20E−06 | 4.13E−06 | 1.73E−05 | 2.50E−05 |
|  | LC50 | 1.12E−05 | 2.40E−06 | 1.21E−05 | 3.83E−05 | 2.50E−05 |
| H-MEC-1 | GI50 | 9.90E−07 | 6.70E−07 | 5.99E−07 | 3.90E−06 | 1.14E−07 |
|  | TGI | 9.71E−06 | 1.33E−06 | 1.56E−06 | 9.34E−06 | 5.32E−07 |
|  | LC50 | 1.87E−05 | 2.65E−06 | 5.96E−06 | 2.23E−05 | 1.86E−06 |
| A-549 | GI50 | 1.03E−06 | 5.53E−07 | 7.48E−07 | 6.28E−06 | 1.35E−07 |
|  | TGI | 6.95E−06 | 1.72E−06 | 1.97E−06 | 1.48E−05 | 2.26E−06 |
|  | LC50 | 1.87E−05 | 8.23E−06 | 3.39E−05 | 3.49E−05 | 1.43E−05 |
| K-562 | GI50 | 6.09E−06 | 1.70E−06 | 4.47E−06 | 8.23E−06 | 4.07E−06 |
|  | TGI | 1.87E−05 | 2.98E−06 | 1.13E−05 | 1.83E−05 | 7.69E−06 |
|  | LC50 | 1.87E−05 | 1.62E−05 | 2.89E−05 | 3.83E−05 | 1.46E−05 |
| PANC-1 | GI50 | 5.85E−06 | 1.35E−06 | 2.05E−06 | 8.96E−06 | 8.87E−06 |
|  | TGI | 1.87E−05 | 6.18E−06 | 9.35E−06 | 1.94E−05 | 2.50E−05 |
|  | LC50 | 1.87E−05 | 3.25E−05 | 3.39E−05 | 3.83E−05 | 2.50E−05 |

-continued

| | | | | | | |
|---|---|---|---|---|---|---|
| HT-29 | GI50 | 1.03E−06 | 1.04E−06 | 2.15E−06 | 1.25E−05 | 1.99E−06 |
| | TGI | 1.87E−05 | 3.25E−06 | 1.31E−05 | 3.46E−05 | 2.50E−05 |
| | LC50 | 1.87E−05 | 3.25E−05 | 3.39E−05 | 3.83E−05 | 2.50E−05 |
| LOVO | GI50 | 1.34E−06 | 5.40E−07 | 8.94E−07 | 6.74E−06 | 8.84E−07 |
| | TGI | 4.37E−06 | 1.98E−06 | 1.91E−06 | 1.63E−05 | 5.42E−06 |
| | LC50 | 1.29E−05 | 1.03E−05 | 3.39E−05 | 3.83E−05 | 2.50E−05 |
| LOVO-DOX | GI50 | 1.06E−06 | 8.27E−07 | 1.39E−06 | 5.93E−06 | 9.54E−07 |
| | TGI | 3.87E−06 | 2.41E−06 | 5.76E−06 | 1.66E−05 | 3.62E−06 |
| | LC50 | 1.51E−05 | 3.25E−05 | 3.39E−05 | 3.83E−05 | 1.55E−05 |
| HELA | GI50 | — | — | — | — | — |
| | TGI | — | — | — | — | — |
| | LC50 | — | — | — | — | — |
| HELA-APL | GI50 | — | — | — | — | — |
| | TGI | — | — | — | — | — |
| | LC50 | — | — | — | — | — |

| | | 60 | 65 | 101 |
|---|---|---|---|---|
| DU-145 | GI50 | 3.36E−05 | 3.75E−05 | 1.18E−07 |
| | TGI | 3.36E−05 | 3.75E−05 | 1.80E−06 |
| | LC50 | 3.36E−05 | 3.75E−05 | 3.03E−05 |
| LN-caP | GI50 | 3.36E−05 | 1.71E−05 | 2.24E−08 |
| | TGI | 3.36E−05 | 3.75E−05 | 1.32E−07 |
| | LC50 | 3.36E−05 | 3.75E−05 | 4.74E−06 |
| SKOV-3 | GI50 | 3.36E−05 | 3.75E−05 | 4.44E−06 |
| | TGI | 3.36E−05 | 3.75E−05 | 1.41E−05 |
| | LC50 | 3.36E−05 | 3.75E−05 | 3.39E−05 |
| IGROV | GI50 | 1.08E−05 | 3.75E−05 | 3.79E−06 |
| | TGI | 3.36E−05 | 3.75E−05 | 1.06E−05 |
| | LC50 | 3.36E−05 | 3.75E−05 | 2.96E−05 |
| IGROV-ET | GI50 | 3.36E−05 | 3.75E−05 | 6.60E−06 |
| | TGI | 3.36E−05 | 3.75E−05 | 2.08E−05 |
| | LC50 | 3.36E−05 | 3.75E−05 | 3.39E−05 |
| SK-BR-3 | GI50 | 2.40E−07 | 1.46E−06 | 1.28E−07 |
| | TGI | 9.95E−07 | 3.75E−05 | 8.77E−07 |
| | LC50 | 3.36E−06 | 3.75E−05 | 1.02E−05 |
| MEL-28 | GI50 | 3.36E−05 | 3.75E−05 | 5.22E−06 |
| | TGI | 3.36E−05 | 3.75E−05 | 1.07E−05 |
| | LC50 | 3.36E−05 | 3.75E−05 | 2.19E−05 |
| H-MEC-1 | GI50 | 2.26E−05 | 1.18E−05 | 6.77E−09 |
| | TGI | 3.36E−05 | 3.75E−05 | 1.57E−08 |
| | LC50 | 3.36E−05 | 3.75E−05 | 4.44E−08 |
| A-549 | GI50 | 2.26E−05 | 2.64E−05 | 2.39E−06 |
| | TGI | 3.36E−05 | 3.75E−05 | 1.09E−05 |
| | LC50 | 3.36E−05 | 3.75E−05 | 3.39E−05 |
| K-562 | GI50 | 3.36E−05 | 3.75E−05 | 5.55E−06 |
| | TGI | 3.36E−05 | 3.75E−05 | 1.79E−05 |
| | LC50 | 3.36E−05 | 3.75E−05 | 3.39E−05 |
| PANC-1 | GI50 | 3.36E−05 | 3.75E−05 | 1.49E−07 |
| | TGI | 3.36E−05 | 3.75E−05 | 4.88E−06 |
| | LC50 | 3.36E−05 | 3.75E−05 | 3.39E−05 |
| HT-29 | GI50 | 3.36E−05 | 3.75E−05 | 8.87E−06 |
| | TGI | 3.36E−05 | 3.75E−05 | 2.35E−05 |
| | LC50 | 3.36E−05 | 3.75E−05 | 3.39E−05 |
| LOVO | GI50 | 3.36E−05 | 3.75E−05 | 3.52E−06 |
| | TGI | 3.36E−05 | 3.75E−05 | 1.41E−05 |
| | LC50 | 3.36E−05 | 3.75E−05 | 3.39E−05 |
| LOVO-DOX | GI50 | 3.36E−05 | 3.75E−05 | 2.35E−06 |
| | TGI | 3.36E−05 | 3.75E−05 | 1.59E−05 |
| | LC50 | 3.36E−05 | 3.75E−05 | 3.39E−05 |
| HELA | GI50 | — | — | — |
| | TGI | — | — | — |
| | LC50 | — | — | — |
| HELA-APL | GI50 | — | — | — |
| | TGI | — | — | — |
| | LC50 | — | — | — |

| | | 78 | 19a | 77 | 90 | 91 |
|---|---|---|---|---|---|---|
| DU-145 | GI50 | 7.70E−07 | 3.05E−09 | 6.30E−07 | 3.55E−07 | 3.36E−07 |
| | TGI | 1.87E−06 | 7.94E−07 | 1.68E−06 | 1.03E−06 | 1.34E−06 |
| | LC50 | 2.82E−05 | 3.79E−06 | 2.78E−05 | 1.07E−05 | 2.49E−05 |
| LN-caP | GI50 | — | 7.36E−07 | 6.17E−07 | — | — |
| | TGI | — | 2.18E−06 | 1.35E−06 | — | — |
| | LC50 | — | 2.25E−05 | 2.96E−06 | — | — |
| SKOV-3 | GI50 | 7.84E−07 | 1.14E−06 | 1.30E−06 | 4.65E−07 | 7.00E−07 |
| | TGI | 1.87E−06 | 4.67E−06 | 3.26E−06 | 1.15E−06 | 2.12E−06 |
| | LC50 | 2.82E−05 | 2.18E−05 | 3.26E−06 | 1.39E−05 | 2.49E−05 |

-continued

| | | | | | | |
|---|---|---|---|---|---|---|
| IGROV | GI50 | 6.21E−07 | 1.85E−06 | 1.30E−06 | 3.39E−07 | 2.41E−07 |
| | TGI | 1.41E−06 | 9.56E−06 | 2.74E−06 | 6.92E−07 | 9.73E−07 |
| | LC50 | 4.74E−06 | 3.05E−05 | 3.26E−05 | 1.41E−06 | 6.02E−06 |
| IGROV-ET | GI50 | 1.08E−06 | 1.41E−06 | 5.55E−07 | 1.92E−06 | 1.16E−06 |
| | TGI | 2.47E−06 | 4.98E−06 | 1.61E−06 | 6.95E−06 | 1.98E−06 |
| | LC50 | 1.43E−06 | 1.45E−05 | 3.26E−05 | 1.58E−05 | 2.49E−05 |
| SK-BR-3 | GI50 | 5.28E−07 | 4.77E−07 | 6.43E−07 | 3.11E−07 | 2.51E−07 |
| | TGI | 1.15E−06 | 1.68E−06 | 1.34E−06 | 6.64E−07 | 6.45E−07 |
| | LC50 | 2.49E−06 | 8.58E−06 | 2.79E−06 | 1.42E−06 | 1.65E−06 |
| MEL-28 | GI50 | 7.17E−07 | 1.46E−06 | 3.98E−07 | 3.97E−07 | 1.80E−07 |
| | TGI | 1.78E−06 | 5.16E−06 | 9.24E−07 | 9.68E−07 | 5.10E−07 |
| | LC50 | 7.05E−06 | 1.31E−05 | 2.16E−06 | 3.45E−06 | 1.25E−06 |
| H-MEC-1 | GI50 | — | 1.23E−07 | 2.06E−07 | — | — |
| | TGI | — | 6.72E−07 | 3.21E−07 | — | — |
| | LC50 | — | 3.82E−06 | 1.26E−06 | — | — |
| A-549 | GI50 | 7.37E−07 | 3.24E−06 | 3.26E−05 | 8.87E−07 | 1.09E−06 |
| | TGI | 1.68E−06 | 7.64E−06 | 3.26E−05 | 2.05E−06 | 2.09E−06 |
| | LC50 | 8.01E−06 | 1.80E−05 | 3.26E−06 | 7.05E−06 | 8.29E−06 |
| K-562 | GI50 | 5.50E−06 | 1.78E−06 | 1.21E−06 | 1.23E−06 | 1.32E−06 |
| | TGI | 2.30E−05 | 6.42E−06 | 3.26E−05 | 5.28E−06 | 3.78E−06 |
| | LC50 | 2.82E−05 | 2.50E−05 | 3.26E−05 | 1.58E−05 | 2.49E−05 |
| PANC-1 | GI50 | 1.34E−06 | 3.45E−06 | 1.16E−06 | 1.18E−06 | 8.96E−07 |
| | TGI | 1.08E−05 | 1.41E−05 | 7.80E−06 | 4.98E−06 | 2.44E−06 |
| | LC50 | 2.82E−05 | 3.05E−05 | 3.26E−05 | 1.58E−05 | 1.62E−05 |
| HT-29 | GI50 | 1.34E−06 | 1.94E−06 | 8.29E−07 | 1.27E−06 | 1.34E−06 |
| | TGI | 2.82E−05 | 3.05E−05 | 3.26E−06 | 1.44E−05 | 2.49E−06 |
| | LC50 | 1.43E−06 | 3.05E−05 | 3.26E−06 | 1.58E−05 | 2.49E−05 |
| LOVO | GI50 | 5.53E−07 | 4.67E−07 | 6.29E−07 | 2.76E−07 | 2.01E−07 |
| | TGI | 1.44E−06 | 2.74E−06 | 2.02E−06 | 6.54E−07 | 8.49E−07 |
| | LC50 | 5.05E−06 | 1.11E−05 | 3.26E−05 | 1.56E−06 | 6.82E−06 |
| LOVO-DOX | GI50 | 1.51E−07 | 1.03E−06 | 7.02E−07 | 5.97E−07 | 7.74E−07 |
| | TGI | 1.86E−06 | 7.51E−06 | 2.79E−06 | 1.27E−06 | 1.86E−06 |
| | LC50 | 1.82E−05 | 3.05E−05 | 1.51E−05 | 8.07E−06 | 7.47E−06 |
| HELA | GI50 | — | — | — | — | — |
| | TGI | — | — | — | — | — |
| | LC50 | — | — | — | — | — |
| HELA-APL | GI50 | — | — | — | — | — |
| | TGI | — | — | — | — | — |
| | LC50 | — | — | — | — | — |

| | | 76 | 18b | 24 | 26 | 116 |
|---|---|---|---|---|---|---|
| DU-145 | GI50 | 5.42E−07 | 2.57E−05 | 8.31E−07 | 5.81E−07 | 1.13E−06 |
| | TGI | 1.42E−06 | 2.57E−05 | 1.91E−06 | 2.10E−06 | 2.54E−06 |
| | LC50 | 3.42E−06 | 2.57E−05 | 1.56E−05 | 1.49E−05 | 2.63E−05 |
| LN-caP | GI50 | 7.29E−08 | 1.66E−05 | 1.74E−07 | 7.03E−07 | 6.02E−07 |
| | TGI | 4.55E−07 | 2.57E−05 | 7.24E−07 | 1.27E−06 | 1.21E−06 |
| | LC50 | 3.08E−06 | 2.57E−05 | 3.43E−05 | 2.28E−06 | 2.43E−06 |
| SKOV-3 | GI50 | 1.22E−06 | 2.57E−05 | 1.39E−06 | 2.80E−07 | — |
| | TGI | 3.42E−06 | 2.57E−05 | 1.00E−05 | 1.13E−06 | — |
| | LC50 | 3.43E−05 | 2.57E−05 | 3.43E−05 | 9.35E−06 | — |
| IGROV | GI50 | 7.25E−07 | 2.08E−05 | 9.95E−07 | 2.20E−07 | 9.34E−07 |
| | TGI | 1.77E−06 | 2.57E−05 | 6.38E−06 | 2.73E−06 | 1.66E−06 |
| | LC50 | 3.42E−06 | 2.57E−05 | 2.30E−05 | 9.17E−06 | 2.63E−05 |
| IGROV-ET | GI50 | 6.49E−07 | 2.57E−05 | 1.01E−06 | 1.70E−06 | 1.37E−06 |
| | TGI | 2.04E−06 | 2.57E−05 | 7.11E−06 | 7.50E−06 | 2.50E−06 |
| | LC50 | 3.42E−05 | 2.57E−05 | 3.43E−05 | 2.55E−05 | 2.63E−05 |
| SK-BR-3 | GI50 | 5.41E−07 | 2.57E−05 | 1.04E−06 | 2.78E−07 | 8.92E−07 |
| | TGI | 1.21E−06 | 2.57E−05 | 4.77E−06 | 8.38E−07 | 1.55E−06 |
| | LC50 | 2.71E−06 | 2.57E−05 | 1.04E−05 | 2.53E−06 | 3.50E−06 |
| MEL-28 | GI50 | 3.59E−07 | 2.57E−05 | 7.21E−07 | 2.73E−07 | 1.10E−06 |
| | TGI | 8.01E−07 | 2.57E−05 | 3.43E−06 | 2.88E−06 | 2.11E−06 |
| | LC50 | 1.79E−06 | 2.57E−05 | 1.26E−05 | 1.01E−05 | 1.04E−05 |
| H-MEC-1 | GI50 | 7.77E−08 | 1.22E−05 | 2.47E−07 | 4.46E−07 | — |
| | TGI | 2.27E−07 | 1.69E−05 | 7.86E−07 | 1.22E−06 | — |
| | LC50 | 1.56E−06 | 2.33E−05 | 2.67E−06 | 8.28E−06 | — |
| A-549 | GI50 | 4.07E−07 | 2.57E−05 | 1.38E−06 | 7.06E−07 | 1.15E−06 |
| | TGI | 1.49E−06 | 2.57E−05 | 6.87E−06 | 2.93E−06 | 7.68E−06 |
| | LC50 | 7.70E−06 | 2.57E−05 | 1.75E−05 | 1.65E−05 | 2.63E−05 |
| K-562 | GI50 | 1.02E−06 | 2.57E−05 | 1.62E−06 | 2.80E−06 | 2.87E−06 |
| | TGI | 2.28E−06 | 2.57E−05 | 7.35E−06 | 8.10E−06 | 2.12E−05 |
| | LC50 | 5.92E−06 | 2.57E−05 | 2.22E−05 | 2.34E−05 | 2.63E−05 |
| PANC-1 | GI50 | 6.50E−07 | 1.03E−05 | 3.88E−06 | 9.33E−07 | 1.79E−06 |
| | TGI | 2.15E−06 | 2.57E−05 | 2.06E−05 | 4.05E−06 | 1.29E−05 |
| | LC50 | 3.42E−07 | 2.57E−05 | 3.43E−05 | 2.13E−05 | 2.63E−05 |
| HT-29 | GI50 | 7.70E−07 | 2.57E−05 | 1.64E−05 | 9.35E−07 | 6.18E−06 |
| | TGI | 3.42E−06 | 2.57E−05 | 3.43E−05 | 3.36E−06 | 1.88E−05 |
| | LC50 | 3.42E−05 | 2.57E−05 | 3.43E−05 | 2.55E−05 | 2.63E−05 |

-continued

| | | | | | | |
|---|---|---|---|---|---|---|
| LOVO | GI50 | 1.63E−07 | 2.57E−05 | 3.25E−05 | 4.15E−07 | 5.50E−07 |
| | TGI | 6.81E−07 | 2.57E−05 | 1.22E−06 | 1.87E−06 | 1.22E−06 |
| | LC50 | 3.42E−05 | 2.57E−05 | 3.43E−07 | 1.34E−05 | 2.63E−05 |
| LOVO-DOX | GI50 | 7.73E−07 | 2.57E−05 | 6.42E−07 | 1.79E−06 | 1.07E−06 |
| | TGI | 3.42E−07 | 2.57E−05 | 3.43E−06 | 1.10E−05 | 2.59E−06 |
| | LC50 | 3.42E−05 | 2.57E−05 | 3.43E−05 | 2.55E−05 | 2.63E−05 |
| HELA | GI50 | — | — | — | — | 1.51E−07 |
| | TGI | — | — | — | — | 5.26E−07 |
| | LC50 | — | — | — | — | 2.63E−05 |
| HELA-APL | GI50 | — | — | — | — | 9.89E−08 |
| | TGI | — | — | — | — | 2.17E−07 |
| | LC50 | — | — | — | — | 2.30E−06 |

| | | 53 | 85 | 104 | 17b | 99 |
|---|---|---|---|---|---|---|
| H-MEC-1 | GI50 | — | 6.19E−06 | — | — | 8.20E−06 |
| | TGI | — | 1.77E−05 | — | — | 2.24E−05 |
| | LC50 | — | 1.77E−05 | — | — | 2.24E−05 |
| A-549 | GI50 | 1.60E−05 | 6.58E−06 | 2.11E−05 | 7.16E−06 | 2.24E−05 |
| | TGI | 1.60E−05 | 1.77E−05 | 2.11E−05 | 1.19E−05 | 2.24E−05 |
| | LC50 | 1.60E−05 | 1.77E−05 | 2.11E−05 | 1.91E−05 | 2.24E−05 |
| HT-29 | GI50 | 1.60E−05 | 1.22E−05 | 2.11E−05 | 7.16E−06 | 2.24E−05 |
| | TGI | 1.60E−05 | 1.77E−05 | 2.11E−05 | 1.19E−05 | 2.24E−05 |
| | LC50 | 1.60E−05 | 1.77E−05 | 2.11E−05 | 1.91E−05 | 2.24E−05 |

| | | 52 | 94 | 103 | 102 | 74 |
|---|---|---|---|---|---|---|
| H-MEC-1 | GI50 | — | 9.19E−06 | — | 6.00E−06 | — |
| | TGI | — | 1.97E−05 | — | 1.09E−05 | — |
| | LC50 | — | 2.41E−05 | — | 1.97E−05 | — |
| A-549 | GI50 | 5.81E−06 | 2.41E−05 | 1.15E−05 | 2.51E−05 | 5.35E−06 |
| | TGI | 9.56E−06 | 2.41E−05 | 2.42E−05 | 2.51E−05 | 1.07E−05 |
| | LC50 | 1.57E−05 | 2.41E−05 | 2.42E−05 | 2.51E−05 | 2.13E−05 |
| HT-29 | GI50 | 5.36E−06 | 2.41E−05 | 1.19E−05 | 2.51E−05 | 1.22E−06 |
| | TGI | 9.20E−06 | 2.41E−05 | 2.42E−05 | 2.51E−05 | 2.55E−05 |
| | LC50 | 1.57E−05 | 2.41E−05 | 2.42E−05 | 2.51E−05 | 2.55E−05 |

| | | 48 | 17a | 23 | 25 | 28 |
|---|---|---|---|---|---|---|
| H-MEC-1 | GI50 | 2.55E−05 | — | — | — | — |
| | TGI | 2.55E−05 | — | — | — | — |
| | LC50 | 2.55E−05 | — | — | — | — |
| A-549 | GI50 | 2.55E−05 | 2.57E−05 | 5.19E−06 | 6.49E−07 | 1.09E−04 |
| | TGI | 2.55E−05 | 7.71E−05 | 1.04E−05 | 3.25E−07 | 1.09E−04 |
| | LC50 | 2.55E−05 | 1.29E−04 | 2.60E−05 | 1.62E−04 | 1.09E−04 |
| HT-29 | GI50 | 2.55E−05 | 2.57E−05 | 5.19E−06 | 9.74E−07 | 1.09E−04 |
| | TGI | 2.55E−05 | 7.71E−05 | 1.30E−05 | 9.74E−07 | 1.09E−04 |
| | LC50 | 2.55E−05 | 1.29E−04 | 2.60E−05 | 1.62E−04 | 1.09E−04 |

| | | 96 | 47 | 84 | 22 | 69 |
|---|---|---|---|---|---|---|
| H-MEC-1 | GI50 | — | 2.67E−05 | 2.67E−05 | — | — |
| | TGI | — | 2.67E−05 | 2.67E−05 | — | — |
| | LC50 | — | 2.67E−05 | 2.67E−05 | — | — |
| A-549 | GI50 | 1.23E−05 | 1.72E−05 | 2.67E−05 | 8.50E−07 | 5.71E−06 |
| | TGI | 2.61E−05 | 2.67E−05 | 2.67E−05 | 2.27E−06 | 2.29E−05 |
| | LC50 | 2.61E−05 | 2.67E−05 | 2.67E−05 | 2.27E−05 | 2.86E−05 |
| HT-29 | GI50 | 1.62E−05 | 2.04E−05 | 2.67E−05 | 2.83E−06 | 1.43E−05 |
| | TGI | 2.61E−05 | 2.67E−05 | 2.67E−05 | 8.50E−06 | 2.86E−05 |
| | LC50 | 2.61E−05 | 2.67E−05 | 2.67E−05 | 1.98E−05 | 2.86E−05 |

| | | 73 | 95 | 9 | 72 | 92 |
|---|---|---|---|---|---|---|
| H-MEC-1 | GI50 | — | 3.08E−05 | — | — | 7.82E−07 |
| | TGI | — | 3.08E−05 | — | — | 3.09E−06 |
| | LC50 | — | 3.08E−05 | — | — | 3.09E−05 |
| A-549 | GI50 | 4.41E−06 | 3.08E−05 | 5.90E−06 | 1.23E−06 | 1.76E−06 |
| | TGI | 1.47E−04 | 3.08E−05 | 1.18E−05 | 6.17E−06 | 6.03E−06 |
| | LC50 | 1.47E−04 | 3.08E−05 | 2.95E−05 | 9.26E−05 | 2.44E−05 |
| HT-29 | GI50 | 2.94E−05 | 3.08E−05 | 9.16E−06 | 9.26E−07 | 2.04E−06 |
| | TGI | 1.47E−04 | 3.08E−05 | 2.57E−05 | 1.54E−05 | 3.09E−05 |
| | LC50 | 1.47E−04 | 3.08E−05 | 2.57E−05 | 1.54E−04 | 3.09E−05 |

| | | 43 | 57 | 58 | 67 | 62 |
|---|---|---|---|---|---|---|
| H-MEC-1 | GI50 | — | 3.11E−05 | 3.43E−05 | 3.06E−05 | 3.44E−05 |
| | TGI | — | 3.11E−05 | 3.43E−05 | 3.06E−05 | 3.44E−05 |
| | LC50 | — | 3.11E−05 | 3.43E−05 | 3.06E−05 | 3.44E−05 |

-continued

| | | | | | | |
|---|---|---|---|---|---|---|
| A-549 | GI50 | 2.17E−06 | 2.25E−05 | 3.43E−05 | 3.06E−05 | 3.44E−05 |
| | TGI | 6.21E−06 | 3.11E−05 | 3.43E−05 | 3.06E−05 | 3.44E−05 |
| | LC50 | 3.11E−05 | 3.11E−05 | 3.43E−05 | 3.06E−05 | 3.44E−05 |
| HT-29 | GI50 | 9.32E−07 | 3.11E−05 | 3.43E−05 | 3.06E−05 | 3.44E−05 |
| | TGI | 6.21E−06 | 3.11E−05 | 3.43E−05 | 3.06E−05 | 3.44E−05 |
| | LC50 | 3.11E−05 | 3.11E−05 | 3.43E−05 | 3.06E−05 | 3.44E−05 |

| | | 75 | 70 | 63 | 79 | 59 |
|---|---|---|---|---|---|---|
| H-MEC-1 | GI50 | 1.43E−05 | 1.19E−07 | 3.84E−05 | — | 2.97E−05 |
| | TGI | 8.00E−06 | 3.93E−07 | 3.84E−05 | — | 2.97E−05 |
| | LC50 | 3.62E−05 | 4.00E−06 | 3.84E−05 | — | 2.97E−05 |
| A-549 | GI50 | 4.20E−06 | 1.82E−07 | 3.84E−05 | 2.51E−05 | 2.97E−05 |
| | TGI | 9.45E−06 | 5.60E−07 | 3.84E−05 | 2.51E−05 | 2.97E−05 |
| | LC50 | 2.13E−05 | 3.35E−06 | 3.84E−05 | 2.51E−05 | 2.97E−05 |
| HT-29 | GI50 | 5.79E−06 | 3.81E−08 | 3.84E−05 | 2.51E−05 | 2.97E−05 |
| | TGI | 3.62E−06 | 3.81E−06 | 3.84E−05 | 2.51E−05 | 2.97E−05 |
| | LC50 | 3.62E−05 | 3.81E−05 | 3.84E−05 | 2.51E−05 | 2.97E−05 |

| | | 4 | 68 | 93 | 97 | 83 |
|---|---|---|---|---|---|---|
| DU-145 | GI50 | 9.52E−08 | 3.65E−07 | 6.46E−08 | 2.57E−07 | 6.21E−07 |
| | TGI | 2.46E−07 | 1.03E−06 | 4.16E−07 | 3.19E−06 | 1.49E−06 |
| | LC50 | 5.30E−06 | 2.90E−06 | 2.33E−06 | 1.28E−05 | 8.32E−06 |
| LN-caP | GI50 | 6.42E−08 | 3.10E−07 | 1.27E−07 | 1.09E−06 | 4.24E−07 |
| | TGI | 1.32E−07 | 1.05E−06 | 3.68E−07 | 2.88E−07 | 8.03E−07 |
| | LC50 | 2.72E−07 | 4.41E−06 | 1.67E−06 | 5.82E−06 | 1.52E−06 |
| SKOV-3 | GI50 | — | — | — | — | — |
| | TGI | — | — | — | — | — |
| | LC50 | — | — | — | — | — |
| IGROV | GI50 | 8.08E−08 | 1.72E−06 | 1.44E−07 | 9.31E−08 | 9.98E−07 |
| | TGI | 8.10E−08 | 1.27E−05 | 8.76E−07 | 3.10E−06 | 3.17E−06 |
| | LC50 | 1.32E−06 | 2.90E−05 | 2.52E−05 | 2.70E−05 | 2.60E−05 |
| IGROV-ET | GI50 | 1.29E−07 | 2.82E−06 | 8.60E−07 | 1.52E−06 | 1.08E−05 |
| | TGI | 3.42E−07 | 1.44E−05 | 2.09E−06 | 8.12E−06 | 2.29E−06 |
| | LC50 | 2.29E−05 | 2.90E−05 | 2.52E−06 | 2.77E−05 | 2.60E−05 |
| SK-BR-3 | GI50 | 7.36E−08 | 6.41E−07 | 3.26E−07 | 1.92E−06 | 5.75E−07 |
| | TGI | 1.59E−07 | 3.42E−06 | 1.59E−06 | 7.37E−06 | 1.05E−06 |
| | LC50 | 3.45E−07 | 1.61E−05 | 1.56E−05 | 2.36E−05 | 1.92E−06 |
| MEL-28 | GI50 | 6.92E−08 | 1.08E−06 | 7.67E−07 | 3.08E−06 | 1.32E−06 |
| | TGI | 1.49E−07 | 4.49E−06 | 3.71E−06 | 7.43E−06 | 3.64E−06 |
| | LC50 | 3.21E−07 | 1.44E−05 | 1.07E−05 | 1.80E−05 | 1.18E−05 |
| H-MEC-1 | GI50 | — | — | — | — | — |
| | TGI | — | — | — | — | — |
| | LC50 | — | — | — | — | — |
| A-549 | GI50 | 6.38E−08 | 1.29E−06 | 2.49E−07 | 7.07E−07 | 7.57E−07 |
| | TGI | 2.62E−07 | 5.10E−06 | 9.34E−07 | 4.55E−06 | 1.57E−06 |
| | LC50 | 1.22E−05 | 2.90E−05 | 5.98E−06 | 2.23E−05 | 8.66E−06 |
| K-562 | GI50 | 7.27E−07 | 2.51E−06 | 8.98E−07 | 2.85E−06 | 2.60E−06 |
| | TGI | 2.20E−06 | 1.84E−05 | 1.57E−06 | 8.34E−06 | 1.73E−05 |
| | LC50 | 2.46E−05 | 2.90E−05 | 2.52E−05 | 2.44E−05 | 2.60E−05 |
| PANC-1 | GI50 | 1.62E−07 | 5.88E−07 | 2.20E−07 | 4.05E−06 | 1.95E−06 |
| | TGI | 1.76E−06 | 1.15E−05 | 2.78E−06 | 9.98E−06 | 1.07E−05 |
| | LC50 | 1.54E−05 | 2.90E−05 | 2.52E−05 | 2.46E−05 | 2.60E−05 |
| HT-29 | GI50 | 1.17E−07 | 1.14E−06 | 1.76E−07 | 4.57E−07 | 1.37E−06 |
| | TGI | 4.98E−07 | 6.93E−06 | 1.32E−06 | 4.85E−06 | 3.90E−06 |
| | LC50 | 1.13E−05 | 2.90E−05 | 2.52E−05 | 1.87E−05 | 2.60E−05 |
| LOVO | GI50 | 1.02E−07 | 5.39E−07 | 9.84E−07 | 5.07E−06 | 4.71E−07 |
| | TGI | 2.54E−07 | 1.18E−06 | 3.84E−06 | 1.27E−05 | 9.90E−07 |
| | LC50 | 2.21E−05 | 2.59E−06 | 1.74E−05 | 2.77E−05 | 2.09E−06 |
| LOVO-DOX | GI50 | 1.01E−07 | 1.15E−06 | 6.99E−07 | 7.51E−06 | 8.03E−07 |
| | TGI | 2.96E−07 | 2.43E−06 | 1.68E−06 | 1.93E−06 | 1.72E−06 |
| | LC50 | 3.61E−05 | 2.90E−05 | 2.52E−05 | 2.77E−05 | 1.78E−05 |
| HELA | GI50 | 8.11E−08 | 1.00E−08 | 2.52E−09 | 5.76E−08 | 4.78E−08 |
| | TGI | 1.60E−07 | 3.19E−08 | 5.10E−09 | 1.28E−07 | 1.38E−07 |
| | LC50 | 3.14E−07 | 4.58E−07 | 1.55E−08 | 3.58E−07 | 9.85E−07 |
| HELA-APL | GI50 | 6.60E−08 | 1.03E−08 | 4.67E−09 | 7.87E−08 | 4.78E−08 |
| | TGI | 1.45E−07 | 5.68E−08 | 6.03E−09 | 1.77E−07 | 1.11E−07 |
| | LC50 | 3.18E−07 | 6.55E−07 | 2.90E−08 | 1.85E−07 | 2.57E−07 |

| | | 108 | 26 | 73 | 18a | 69 |
|---|---|---|---|---|---|---|
| DU-145 | GI50 | 1.50E−06 | 4.48E−06 | 2.94E−05 | 4.27E−06 | 9.85E−07 |
| | TGI | 2.64E−05 | 8.99E−06 | 2.94E−05 | 9.99E−06 | 4.59E−06 |
| | LC50 | 2.64E−05 | 1.80E−05 | 2.94E−05 | 2.33E−05 | 2.37E−05 |
| LN-caP | GI50 | — | 4.51E−06 | 4.76E−06 | 3.49E−06 | 1.08E−06 |
| | TGI | — | 8.89E−06 | 1.51E−05 | 7.31E−06 | 4.77E−06 |
| | LC50 | — | 1.75E−05 | 2.94E−05 | 1.53E−05 | 2.85E−05 |

-continued

| | | | | | | |
|---|---|---|---|---|---|---|
| SKOV-3 | GI50 | — | — | — | — | — |
| | TGI | — | — | — | — | — |
| | LC50 | — | — | — | — | — |
| IGROV | GI50 | 2.33E−06 | 7.21E−07 | 5.41E−06 | 5.47E−06 | 2.13E−06 |
| | TGI | 2.64E−05 | 1.58E−07 | 2.94E−05 | 1.33E−05 | 8.53E−06 |
| | LC50 | 2.64E−05 | 9.25E−06 | 2.94E−05 | 2.79E−05 | 2.85E−05 |
| IGROV-ET | GI50 | 1.13E−05 | 9.17E−07 | 2.05E−05 | 7.06E−06 | 7.31E−06 |
| | TGI | 2.64E−05 | 1.83E−06 | 2.94E−05 | 1.53E−05 | 2.18E−05 |
| | LC50 | 2.64E−05 | 1.14E−05 | 2.94E−05 | 2.79E−05 | 2.85E−05 |
| SK-BR-3 | GI50 | 5.62E−06 | 4.18E−06 | 2.08E−06 | 1.34E−06 | 1.23E−06 |
| | TGI | 1.60E−05 | 9.30E−06 | 9.37E−06 | 4.94E−06 | 6.25E−06 |
| | LC50 | 2.64E−05 | 2.07E−05 | 2.94E−05 | 2.79E−05 | 2.48E−05 |
| MEL-28 | GI50 | 9.25E−07 | 2.02E−07 | 5.46E−06 | 4.97E−06 | 2.19E−06 |
| | TGI | 2.64E−05 | 5.38E−07 | 2.94E−05 | 1.20E−05 | 6.51E−06 |
| | LC50 | 2.64E−05 | 1.29E−06 | 2.94E−05 | 2.79E−05 | 1.64E−05 |
| H-MEC-1 | GI50 | — | — | — | — | — |
| | TGI | — | — | — | — | — |
| | LC50 | — | — | — | — | — |
| A-549 | GI50 | 2.02E−06 | 6.88E−06 | 1.13E−05 | 7.31E−06 | 5.17E−07 |
| | TGI | 2.16E−05 | 1.22E−05 | 2.94E−05 | 1.66E−05 | 1.19E−06 |
| | LC50 | 2.64E−05 | 2.15E−05 | 2.94E−05 | 2.79E−05 | 2.75E−06 |
| K-562 | GI50 | — | 6.29E−06 | 1.37E−05 | 4.72E−06 | 1.28E−05 |
| | TGI | — | 1.07E−05 | 2.94E−05 | 1.66E−05 | 2.85E−05 |
| | LC50 | — | 1.81E−05 | 2.94E−05 | 2.79E−05 | 2.85E−05 |
| PANC-1 | GI50 | 3.37E−06 | 4.38E−06 | 1.23E−05 | 6.53E−06 | 4.99E−06 |
| | TGI | 2.64E−05 | 8.79E−06 | 2.94E−05 | 1.46E−05 | 1.91E−05 |
| | LC50 | 2.64E−05 | 1.76E−05 | 2.94E−05 | 2.79E−05 | 2.85E−05 |
| HT-29 | GI50 | 7.01E−07 | 1.05E−06 | 1.46E−05 | 4.41E−06 | 8.87E−07 |
| | TGI | 2.64E−05 | 3.47E−06 | 2.94E−05 | 1.67E−05 | 6.51E−06 |
| | LC50 | 2.64E−05 | 2.46E−05 | 2.94E−05 | 2.79E−05 | 2.85E−05 |
| LOVO | GI50 | 2.08E−07 | 5.25E−07 | 1.44E−05 | 5.11E−06 | 1.22E−06 |
| | TGI | 7.57E−07 | 1.03E−06 | 2.94E−05 | 9.32E−06 | 7.28E−06 |
| | LC50 | 4.85E−06 | 2.03E−06 | 2.94E−05 | 1.70E−05 | 2.85E−05 |
| LOVO-DOX | GI50 | 6.80E−07 | 6.09E−06 | 1.01E−05 | 3.10E−06 | 2.04E−06 |
| | TGI | 1.61E−06 | 1.08E−06 | 2.94E−05 | 9.74E−06 | 9.79E−06 |
| | LC50 | 2.64E−05 | 1.90E−05 | 2.94E−05 | 2.79E−05 | 2.85E−05 |
| HELA | GI50 | 7.51E−09 | 1.97E−09 | 8.96E−09 | 4.49E−08 | 7.16E−09 |
| | TGI | 1.15E−07 | 6.91E−09 | 3.58E−08 | 3.68E−06 | 3.60E−08 |
| | LC50 | 2.64E−05 | 2.31E−08 | 2.09E−07 | 1.41E−05 | 5.34E−06 |
| HELA-APL | GI50 | 9.54E−09 | 1.77E−09 | 1.30E−08 | 5.69E−08 | 5.94E−09 |
| | TGI | 2.04E−07 | 8.64E−09 | 7.23E−08 | 8.31E−07 | 2.45E−08 |
| | LC50 | 2.64E−05 | 2.27E−07 | 7.23E−06 | 6.56E−06 | 3.80E−07 |

| | | 95 | 72 | 54 | 43 |
|---|---|---|---|---|---|
| DU-145 | GI50 | 1.02E−05 | 2.35E−06 | 3.60E−07 | 1.68E−06 |
| | TGI | 3.08E−05 | 7.43E−06 | 1.32E−06 | 6.79E−06 |
| | LC50 | 3.08E−05 | 2.10E−05 | 2.73E−05 | 2.45E−05 |
| LN-caP | GI50 | 4.10E−06 | 3.48E−05 | 2.87E−07 | 1.36E−06 |
| | TGI | 3.08E−05 | 8.87E−06 | 7.24E−07 | 3.94E−06 |
| | LC50 | 3.08E−05 | 2.71E−05 | 1.82E−06 | 1.25E−05 |
| SKOV-3 | GI50 | — | — | — | — |
| | TGI | — | — | — | — |
| | LC50 | — | — | — | — |
| IGROV | GI50 | 3.08E−05 | 8.48E−06 | 4.40E−07 | 6.64E−06 |
| | TGI | 3.08E−05 | 2.03E−05 | 1.37E−06 | 1.60E−05 |
| | LC50 | 3.08E−05 | 3.08E−05 | 2.73E−05 | 3.10E−05 |
| IGROV-ET | GI50 | 3.95E−06 | 8.48E−06 | 4.21E−07 | 3.69E−06 |
| | TGI | 3.08E−05 | 2.03E−05 | 1.48E−06 | 1.87E−05 |
| | LC50 | 3.08E−05 | 3.08E−05 | 2.73E−05 | 3.10E−05 |
| SK-BR-3 | GI50 | 1.52E−06 | 2.12E−06 | 5.30E−07 | 1.24E−06 |
| | TGI | 3.08E−05 | 7.06E−06 | 1.19E−06 | 5.27E−06 |
| | LC50 | 3.08E−05 | 1.96E−05 | 2.67E−06 | 3.10E−05 |
| MEL-28 | GI50 | 3.08E−05 | 1.84E−06 | 9.45E−07 | 8.50E−07 |
| | TGI | 3.08E−05 | 5.21E−06 | 3.22E−06 | 3.72E−06 |
| | LC50 | 3.08E−05 | 1.31E−05 | 1.14E−05 | 1.53E−05 |
| H-MEC-1 | GI50 | — | — | — | — |
| | TGI | — | — | — | — |
| | LC50 | — | — | — | — |
| A-549 | GI50 | 8.63E−06 | 3.20E−06 | 3.39E−07 | 9.37E−07 |
| | TGI | 3.08E−05 | 2.01E−05 | 1.10E−06 | 4.53E−06 |
| | LC50 | 3.08E−05 | 3.08E−05 | 2.73E−05 | 1.73E−05 |
| K-562 | GI50 | 3.08E−05 | 5.06E−06 | 1.67E−06 | 5.27E−06 |
| | TGI | 3.08E−05 | 1.28E−05 | 1.44E−05 | 1.06E−05 |
| | LC50 | 3.08E−05 | 2.34E−05 | 2.73E−05 | 2.12E−03 |
| PANC-1 | GI50 | 2.42E−05 | 4.84E−06 | 8.71E−07 | 5.71E−06 |
| | TGI | 3.08E−05 | 1.49E−05 | 3.28E−06 | 1.65E−05 |
| | LC50 | 3.08E−05 | 3.08E−05 | 2.73E−05 | 3.10E−05 |

| | | -continued | | | |
|---|---|---|---|---|---|
| HT-29 | GI50 | 3.08E−05 | 4.10E−06 | 1.69E−06 | 1.13E−06 |
| | TGI | 3.08E−05 | 1.19E−05 | 8.71E−06 | 6.33E−05 |
| | LC50 | 3.08E−05 | 3.08E−05 | 2.73E−05 | 3.10E−05 |
| LOVO | GI50 | 1.13E−05 | 2.08E−07 | 2.66E−07 | 7.17E−06 |
| | TGI | 3.08E−05 | 1.15E−05 | 1.04E−06 | 2.37E−06 |
| | LC50 | 3.08E−05 | 3.08E−05 | 2.73E−05 | 3.10E−05 |
| LOVO-DOX | GI50 | 3.08E−05 | 3.11E−06 | 1.55E−07 | 1.22E−06 |
| | TGI | 3.08E−05 | 1.65E−05 | 7.32E−07 | 5.24E−06 |
| | LC50 | 3.08E−05 | 3.08E−05 | 2.73E−05 | 3.10E−05 |
| HELA | GI50 | 9.16E−09 | 5.27E−10 | 5.73E−08 | 2.33E−08 |
| | TGI | 2.57E−08 | 1.25E−09 | 1.17E−07 | 2.03E−07 |
| | LC50 | 3.08E−05 | 2.49E−09 | 2.40E−07 | 1.66E−06 |
| HELA-APL | GI50 | 5.46E−09 | 5.18E−10 | 6.12E−08 | 1.82E−08 |
| | TGI | 1.31E−08 | 1.22E−09 | 1.28E−07 | 1.75E−07 |
| | LC50 | 3.82E−08 | 2.99E−09 | 2.70E−07 | 7.88E−06 |

REFERENCES

Bergeron, R. J.; Cavanaugh, P. F. Jr.; Kline, S. J.; Hughes, R. G. Jr.; Elliott, G. T. and Porter C. W. (1984). Antineoplastic and antiherpetic activity of spermidine catecholamide irons chelators. *Biochemical and Biophisical Research Communications*, 121(3): 848-854.

Faircloth, G. T.; Stewart, D. and Clement, J. J. (1988). A simple screening procedure for the quantitative measurement of cytotoxicity assay. *Journal of Tissue and Culture Methods*, 11(4): 201-205.

Monks, A.; Scudiero, D.; Skehan, Ph.; Shoemaker, R.; Paull, K.; Vistica, D., Hose, C.; Langley, J.; Cronise, P.; Vaigro-Wolf, A.; Gray-Goodrich, M.; Campbell, H.; Mayo, J.; Boyd, M. (1991). Feasibility of a high-flux anticancer drug screen using a diverse panel of cultured human tumor cell lines. *Articles*, 83 (11): 757-766.

Mosmann, T. (1983). Rapid colorimetric assay for cellular growth and survival: application to proliferation and cytotoxicity assays. *Journal of Immunological Methods*, 65: 55-63.

Skehan, P. A. et al. (1990), New colorimetric cytotoxicity assay for anticancer drug screening, J. Natl. Cancer Inst., 82:1107-1112.

Schroeder, A. C.; Hughes R. C. Jr and Bloch, A. (1981). Synthesis and Biological Effects of Acyclic Pyrimidine Nucleoside Analoges. *J. Med. Chem.*, 24: 1078-1083.

The invention claimed is:

1. A compound of general formula (5a):

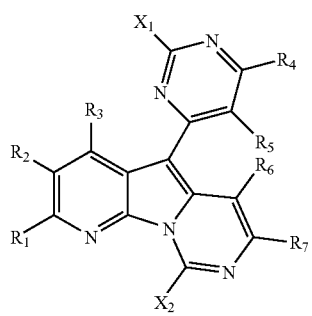

(5a)

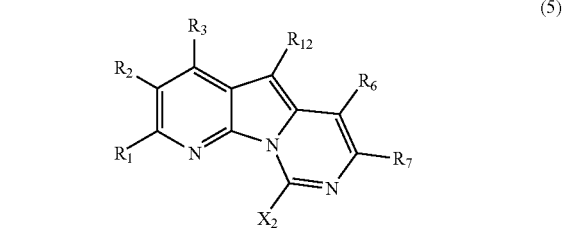

(5)

wherein $R_1$ is selected from the group consisting of OH, OR', SH, SR', SOR', $SO_2R'$, $NO_2$, $NH_2$, NHR', $N(R')_2$, NHCOR', $NHSO_2R'$, CN, halogen, C(=O)H, C(=O)R', $CO_2H$, $CO_2R'$, carboxyalkyl, $C_1$-$C_{12}$ alkyl, $C_2$-$C_{12}$ alkenyl, $C_2$-$C_{12}$ alkynyl, substituted or unsubstituted aryl, substituted or unsubstituted aralkyl and substituted or unsubstituted heteroaromatic;

wherein $X_1$, $X_2$, $R_2$, $R_3$, $R_4$, $R_5$, $R_6$, and $R_7$ are each independently selected from the group consisting of H, OH, OR', SH, SR', SOR', $SO_2R'$, $NO_2$, $NH_2$, NHR', $N(R')_2$, NHCOR', $NHSO_2R'$, CN, halogen, C(=O)H, C(=O)R', $CO_2H$, $CO_2R'$, carboxyalkyl, $C_1$-$C_{12}$ alkyl, $C_2$-$C_{12}$ alkenyl, $C_2$-$C_{12}$ alkynyl, substituted or unsubstituted aryl, substituted or unsubstituted aralkyl and substituted or unsubstituted heteroaromatic;

wherein each of the R' groups is independently selected from the group consisting of H, OH, SH, $NO_2$, $NH_2$, CN, halogen, C(=O)H, C(=O)$CH_3$, $CO_2H$, $CO_2CH_3$, $C_1$-$C_{12}$ alkyl, $C_2$-$C_{12}$ alkenyl, $C_2$-$C_{12}$ alkynyl, aryl, aralkyl and heteroaromatic;

wherein the pairs of groups $R_1$ and $R_2$ may be joined into a fused benzene ring system; or a pharmaceutically acceptable salt thereof.

2. A compound according to claim 1, wherein $R_1$ is $C_1$-$C_6$ alkyl or halogen.

3. A compound according to claim 2, wherein $R_1$ is methyl or chloro.

4. A compound according to claim 1, wherein $R_1$ with $R_2$ form a fused benzene ring.

5. A compound according to claim 4, wherein the fused ring has substituents chosen from OR'.

6. A compound according to claim 5, wherein the substituents of the fused ring comprise one or more of hydroxy or $C_1$-$C_4$ alkoxy.

7. A compound according to claim 6, wherein the substituents of the fused ring comprise one or more of hydroxy or methoxy.

8. A compound according to claim 1, wherein $R_2$ is hydrogen or halogen.

9. A compound according to claim 8, wherein $R_2$ is hydrogen, fluoro or chloro.

10. A compound according to claim 1, wherein $R_3$ is hydrogen, OR', NR'$_2$ or halogen.

11. A compound according to claim 10, wherein $R_3$ is hydrogen, hydroxy, $C_1$-$C_6$ alkoxy, protected hydroxy, amino, protected amino or halogen.

12. A compound according to claim 11, wherein $R_3$ is hydrogen, hydroxy, methoxy, benzyloxy, amino, methoxybenzylamino or chloro.

13. A compound according to claim 12, wherein $R_3$ is hydrogen.

14. A compound according to claim 1, wherein $R_6$ is hydrogen.

15. A compound according to claim 1, wherein $R_7$ is hydrogen.

16. A compound according to claim 1, wherein $R_4$ is hydrogen.

17. A compound according to claim 1, wherein $R_5$ is hydrogen.

18. A compound according to claim 1, wherein $X_1$ is hydrogen, alkyl, OR', NR'$_2$, SR', SOR', SO$_2$R', carboxyalkyl or aralkyl.

19. A compound according to claim 18, wherein $X_1$ is hydrogen, alkyl, hydroxy, alkoxy, aryloxy, amino, protected amino, alkylthio, alkylsulphinyl, alkylsulphonyl, or dicarboxyalkyl.

20. A compound according to claim 19, wherein $X_1$ is hydrogen, methyl, hydroxy, methoxy, ethoxy, benzyloxy, phenoxy, amino, methoxybenzylamino, methylthio, methylsulphinyl, methylsulphonyl or dimethylcarboxyethyl.

21. A compound according to claim 1, wherein $X_2$ is NR'$_2$ or SR'.

22. A compound according to claim 21, wherein $X_2$ is NH$_2$ or alkythio.

23. A compound according to claim 22, wherein $X_2$ is NH$_2$ or thiomethyl.

24. A compound according to claim 1, which is a compound of formula (11):

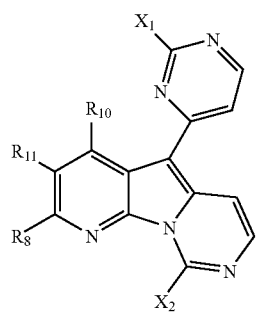

(10)

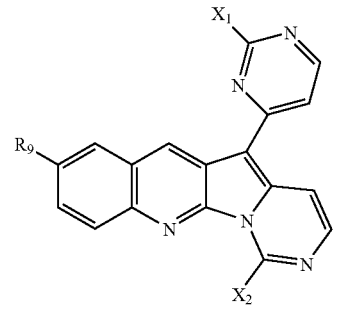

(11)

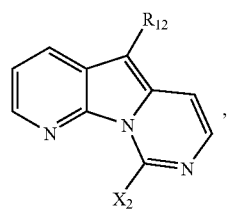

(29)

wherein the substituent groups defined by $X_1$, $X_2$, and $R_9$ are each independently selected from the group consisting of H, OH, OR', SH, SR', SOR', SO$_2$R', NO$_2$, NH$_2$, NHR', N(R')$_2$, NHCOR', NHSO$_2$R', CN, halogen, C(=O)H, C(=O)R', CO$_2$H, CO$_2$R', carboxyalkyl, $C_1$-$C_{12}$ alkyl, $C_2$-$C_{12}$ alkenyl, $C_2$-$C_{12}$ alkynyl, substituted or unsubstituted aryl, substituted or unsubstituted aralkyl and substituted or unsubstituted heteroaromatic; and wherein each of the R' groups is independently selected from the group consisting of H, OH, SH, NO$_2$, NH$_2$, CN, halogen, C(=O)H, C(=O)CH$_3$, CO$_2$H, CO$_2$CH$_3$, $C_1$-$C_{12}$ alkyl, $C_2$-$C_{12}$ alkenyl, $C_2$-$C_{12}$ alkynyl, aryl, aralkyl and heteroaromatic.

25. A compound according to claim 1, wherein one or more of the subsitutents are as follows:

$X_1$ is hydrogen, alkyl, hydroxy, alkoxy, aryloxy, amino, protected amino, alkylthio, alkylsulphinyl, alkylsulphonyl, or dicarboxyalkyl;

$X_2$ is NH$_2$ or alkylthio;

$R_1$ is alkyl or halogen;

$R_3$ is hydrogen, hydroxy, alkoxy, protected hydroxy, amino, protected amino or halogen;

$R_2$ is hydrogen or halogen.

26. A compound according to claim 24, which is a compound of formula (11) wherein one or more of the subsitutents are as follows:

$X_1$ is hydrogen, alkyl, hydroxy, alkoxy, aryloxy, amino, protected amino, alkylthio, alkylsulphinyl, alkylsuiphonyl, or dicarboxyalkyl;

$X_2$ is NH$_2$ or alkylthio;

$R_9$ is hydrogen or alkoxy.

27. A compound according to claim 1 which is a numbered compound given in this specification.

28. A method of treating a mammal affected by cancer which comprises administering to the affected individual a therapeutically effective amount of a compound according to any preceding claim, or a pharmaceutical composition thereof.

29. A pharmaceutical composition which contains as an active ingredient a compound acording to claim 1.

30. A process for preparing a variolin intermediate of formula (8z):

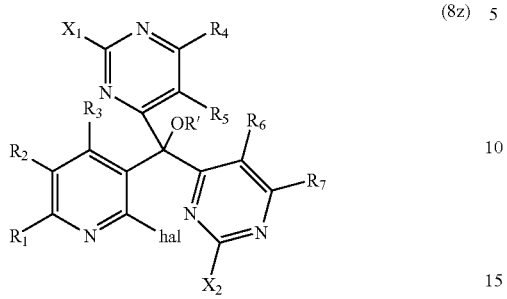

(8z)

where hal is a halogen;

$R_1$ is selected from the group consisting of H, OH, OR', SH, SR', SOR', $SO_2R'$, $NO_2$, $NH_2$, NHR', $N(R')_2$, NHCOR', $NHSO_2R'$, CN, halogen, C(=O)H, C(=O)R', $CO_2H$, $CO_2R'$, carboxyalkyl, $C_1$-$C_{12}$ alkyl, $C_2$-$C_{12}$ alkenyl, $C_2$-$C_{12}$ alkynyl, substituted or unsubstituted aryl, substituted or unsubstituted aralkyl and substituted or unsubstituted heteroaromatic;

wherein $X_1$, $X_2$, $R_2$, $R_3$, $R_4$, $R_5$, $R_6$, and $R_7$ are each independently selected from the group consisting of H, OH, OR', SH, SR', SOR', $SO_2R'$, $NO_2$, $NH_2$, NHR', $N(R')_2$, NHCOR', $NHSO_2R'$, CN, halogen, C(=O)H, C(=O)R', $CO_2H$, $CO_2R'$, carboxyalkyl, $C_1$-$C_{12}$ alkyl, $C_2$-$C_{12}$ alkenyl, $C_2$-$C_{12}$ alkynyl, substituted or unsubstituted aryl, substituted or unsubstituted aralkyl and substituted or unsubstituted heteroaromatic;

wherein each of the R' groups is independently selected from the group consisting of H, OH, SH, $NO_2$, $NH_2$, CN, halogen, C(=O)H, C(=O)$CH_3$, $CO_2H$, $CO_2CH_3$, $C_1$-$C_{12}$ alkyl, $C_2$-$C_{12}$ alkenyl, $C_2$-$C_{12}$alkynyl, aryl, aralkyl and heteroaromatic;

wherein the pairs of groups $R_1$ and $R_2$ may be joined into a fused benzene ring system;

which comprises reacting a compound of formula (31z):

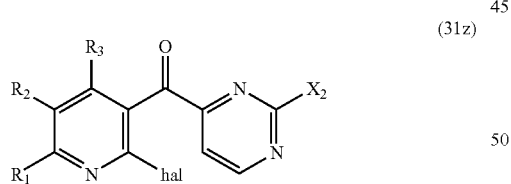

(31z)

where $X_2$, $R_1$, $R_3$, $R_6$, $R_7$, and hal are as defined in this claim, with a compound of formula (13z):

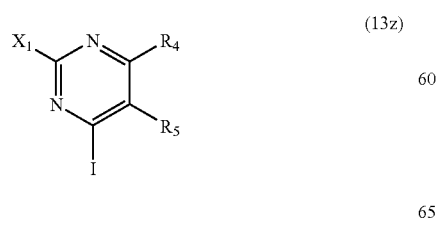

(13z)

where the substituents $X_1$, $R_4$ and $R_5$ are as defined in this claim.

31. A process according to claim 30, wherein the compound of formula (31z) is made by reacting a compound of formula (30z):

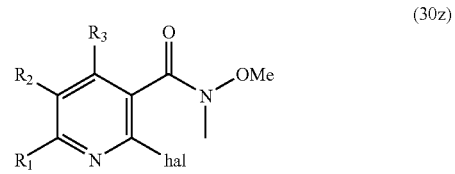

(30z)

where hal, $R_1$, $R_2$ and $R_3$ are as defined in claim 30, with a compound of the formula (13y):

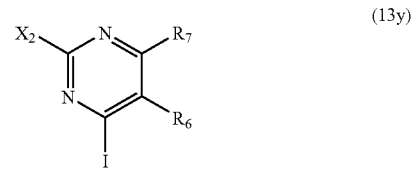

(13y)

where the substituents $X_2$, $R_6$ and $R_7$ are as defined in claim 30.

32. A compound according to claim 24, of the formula:

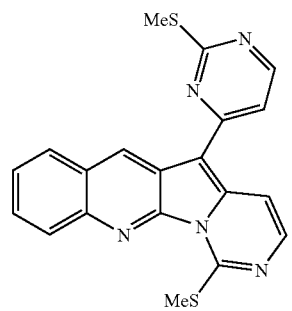

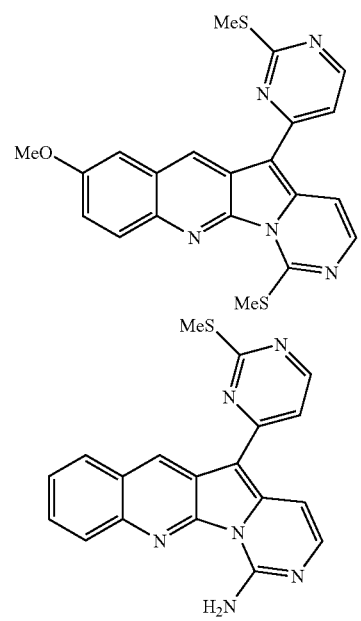

-continued
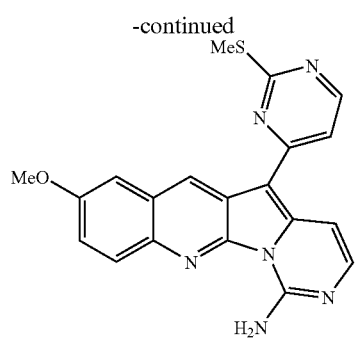
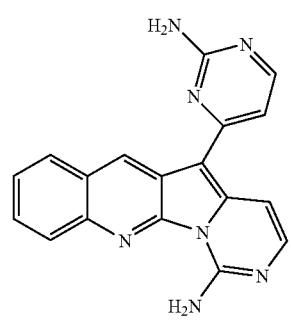
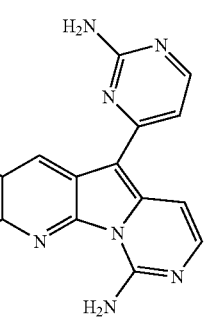
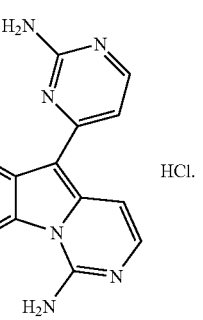
HCl.
33. A compound according to claim 1, of the formula:
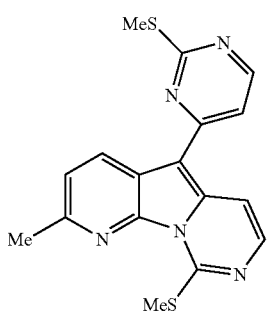
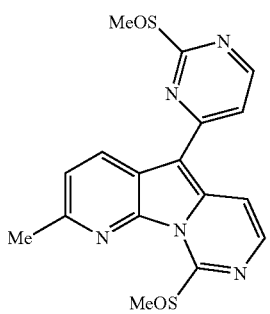
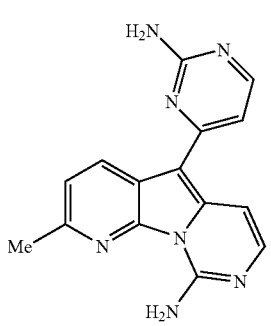
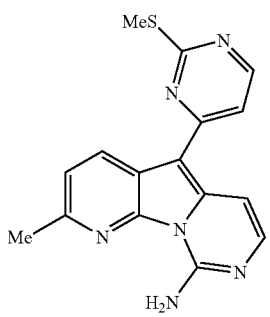

-continued

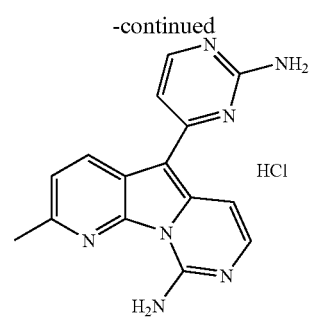

HCl

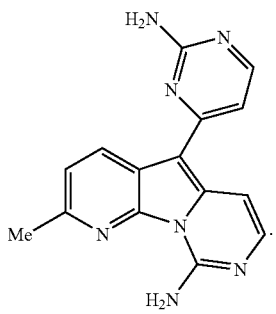

34. A compound according to claim 1 of formula:

35. A compound of formula:

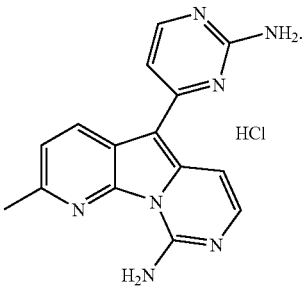

HCl

36. The compound of claim 1, wherein $R_1$ is selected from the group consisting of OH, OR', SH, SR', SOR', SO$_2$R', NO$_2$, NH$_2$, NHR', N(R')$_2$, NHCOR', NHSO$_2$R', CN, halogen, C(=O)H, C(=O)R', CO$_2$H, CO$_2$R', carboxyalkyl, $C_2$-$C_{12}$ alkenyl, $C_2$-$C_{12}$ alkynyl, substituted or unsubstituted aryl, substituted or unsubstituted aralkyl and substituted or unsubstituted heteroaromatic.

* * * * *

UNITED STATES PATENT AND TRADEMARK OFFICE
CERTIFICATE OF CORRECTION

| | | |
|---|---|---|
| PATENT NO. | : 7,495,000 B2 | Page 1 of 1 |
| APPLICATION NO. | : 10/483525 | |
| DATED | : February 24, 2009 | |
| INVENTOR(S) | : Remuinan et al. | |

It is certified that error appears in the above-identified patent and that said Letters Patent is hereby corrected as shown below:

On the title page,

[*] Notice:   Subject to any disclaimer, the term of this patent is extended or adjusted under 35 USC 154(b) by 606 days.

Delete the phrase "by 606 days" and insert -- by 685 days --

Signed and Sealed this

Twenty-sixth Day of January, 2010

David J. Kappos
*Director of the United States Patent and Trademark Office*

UNITED STATES PATENT AND TRADEMARK OFFICE
CERTIFICATE OF CORRECTION

PATENT NO. : 7,495,000 B2
APPLICATION NO. : 10/483525
DATED : February 24, 2009
INVENTOR(S) : Modesto Remuinan et al.

It is certified that error appears in the above-identified patent and that said Letters Patent is hereby corrected as shown below:

Column 8, line 15: "pyidinyl" should read -- pyridinyl --.

Column 8, line 18: "defintions" should read -- definitions --.

Column 16, lines 5-11: the formula reading:

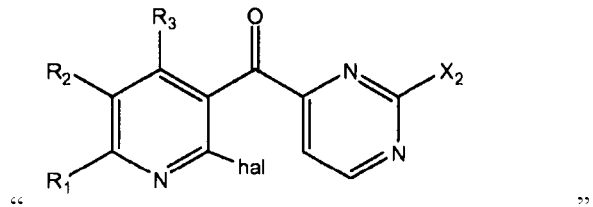

"                                                                   "

should read:

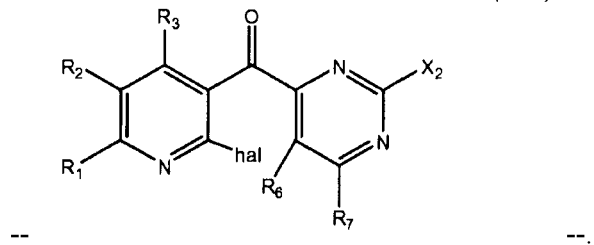

--                                                                  --.

Claim 1, Column 108, lines 20-29: cancel the text and formula

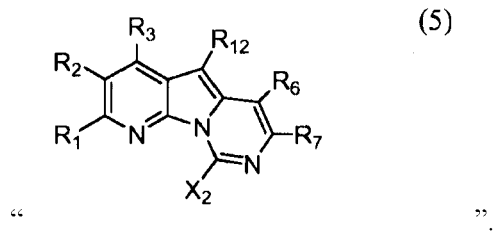

"                                                                   ".

Claim 24, Column 109, lines 54-67: cancel the text and formula
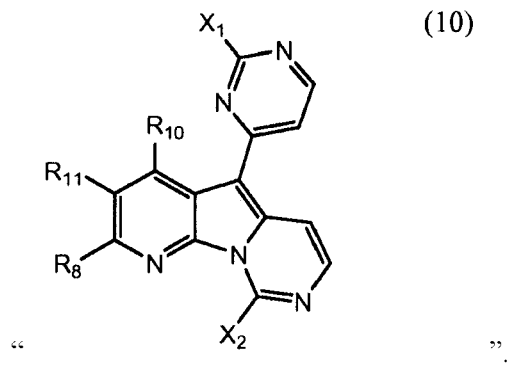
" ".
Claim 24, Column 110, lines 15-24: cancel the text and formula
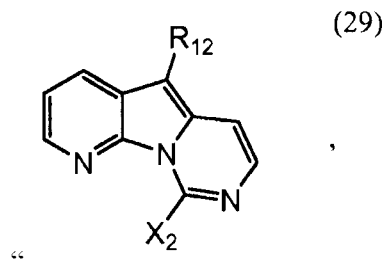
" ".
Claim 26, Column 110, lines 54-55: "alkylsuipho-nyl" should read -- alkylsulphonyl --.
Claim 30, Column 111, lines 45-53: the formula reading:
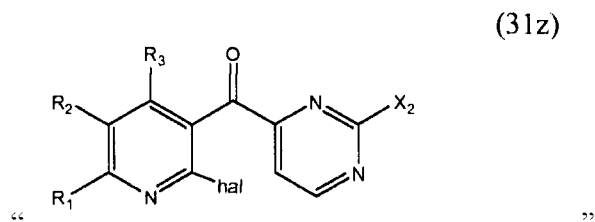
" "
should read:
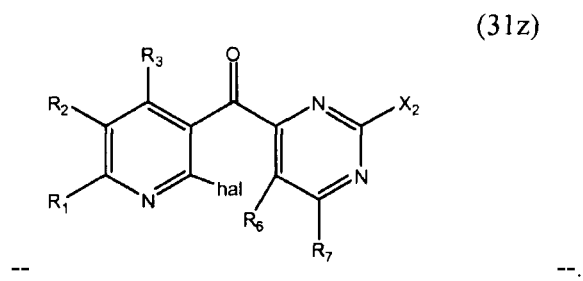
-- --.

Claim 30, Column 111, line 54:
"$X_2$, $R_1$, $R_3$, $R_6$, $R_7$" should read -- $X_2$, $R_1$, $R_2$, $R_3$, $R_6$, $R_7$ --.

Signed and Sealed this

Sixteenth Day of March, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,495,000 B2 | Page 1 of 1 |
| APPLICATION NO. | : 10/483525 | |
| DATED | : February 24, 2009 | |
| INVENTOR(S) | : Modesto Remuiñan et al. | |

It is certified that error appears in the above-identified patent and that said Letters Patent is hereby corrected as shown below:

On the Title page should read,

[*] Notice:   Subject to any disclaimer, the term of this patent is extended or adjusted under 35 U.S.C. 154(b) by 935 days.

Signed and Sealed this

Thirteenth Day of July, 2010

David J. Kappos
*Director of the United States Patent and Trademark Office*